(12) United States Patent
Blanchard et al.

(10) Patent No.: US 7,943,363 B2
(45) Date of Patent: May 17, 2011

(54) METHODS AND COMPOSITIONS FOR IMPROVING THE PRODUCTION OF PRODUCTS IN MICROORGANISMS

(75) Inventors: Jeffrey Blanchard, Leverett, MA (US); Susan Leschine, Leverett, MA (US); Elsa Petit, Northampton, MA (US); John Fabel, Amherst, MA (US); Matthias Schmalisch, Somerville, MA (US)

(73) Assignees: University of Massachusetts, Boston, MA (US); Qteros, Inc., Marlborough, MA (US)

( * ) Notice: Subject to any disclaimer, the term of this patent is extended or adjusted under 35 U.S.C. 154(b) by 0 days.

(21) Appl. No.: 12/510,994

(22) Filed: Jul. 28, 2009

(65) Prior Publication Data

US 2010/0035320 A1 Feb. 11, 2010

Related U.S. Application Data

(60) Provisional application No. 61/084,233, filed on Jul. 28, 2008, provisional application No. 61/225,184, filed on Jul. 13, 2009, provisional application No. 61/228,922, filed on Jul. 27, 2009.

(51) Int. Cl.
*C12N 1/21* (2006.01)
*C12N 15/63* (2006.01)
*C12N 15/55* (2006.01)
*C12N 15/56* (2006.01)
*C12N 15/31* (2006.01)

(52) U.S. Cl. ............... 435/252.3; 435/320.1; 435/252.7; 435/842; 435/195; 435/209; 536/23.2; 536/23.7

(58) Field of Classification Search ........................ None
See application file for complete search history.

(56) References Cited

U.S. PATENT DOCUMENTS

| | | | |
|---|---|---|---|
| 4,094,742 A | 6/1978 | Bellamy | |
| 5,138,007 A | 8/1992 | Meister | |
| 5,496,725 A | 3/1996 | Yu | |
| 5,837,506 A | 11/1998 | Lynd et al. | |
| 5,865,898 A | 2/1999 | Holtzapple et al. | |
| 6,660,506 B2 | 12/2003 | Nguyen et al. | |
| 7,271,244 B2 | 9/2007 | Dotson et al. | |
| 7,682,811 B2 | 3/2010 | Leschine | |
| 2004/0171136 A1 | 9/2004 | Holtzapple et al. | |
| 2004/0231060 A1 | 11/2004 | Burdette et al. | |
| 2006/0105442 A1 | 5/2006 | Wu et al. | |
| 2006/0188980 A1 | 8/2006 | Holtzapple et al. | |
| 2006/0246563 A1 | 11/2006 | Eroma et al. | |
| 2007/0141660 A1 | 6/2007 | Chotani et al. | |
| 2007/0151683 A1 | 7/2007 | Pere et al. | |
| 2007/0178569 A1 | 8/2007 | Leschine et al. | |
| 2007/0193874 A1 | 8/2007 | Adiga et al. | |
| 2007/0207108 A1 | 9/2007 | Yamasaki et al. | |
| 2007/0215300 A1 | 9/2007 | Upfal et al. | |
| 2007/0218530 A1 | 9/2007 | Duck et al. | |
| 2007/0240837 A1 | 10/2007 | Shin et al. | |
| 2007/0249030 A1 | 10/2007 | Fahrenthold et al. | |
| 2008/0003653 A1 | 1/2008 | Wenzel et al. | |
| 2008/0006536 A1 | 1/2008 | Cuomo et al. | |
| 2008/0008783 A1 | 1/2008 | Dale | |
| 2008/0011597 A1 | 1/2008 | Spani | |
| 2008/0029233 A1 | 2/2008 | Wingerson et al. | |
| 2008/0032344 A1 | 2/2008 | Fallavollita | |
| 2008/0044877 A1 | 2/2008 | Penttila et al. | |
| 2008/0045762 A1 | 2/2008 | Foody et al. | |
| 2008/0057555 A1 | 3/2008 | Nguyen | |
| 2008/0102502 A1 | 5/2008 | Foody et al. | |
| 2008/0102503 A1 | 5/2008 | Rush | |
| 2008/0121359 A1 | 5/2008 | Holtzapple et al. | |
| 2008/0190013 A1 | 8/2008 | Argyropoulos | |
| 2008/0199908 A1 | 8/2008 | Smith et al. | |
| 2008/0207959 A1 | 8/2008 | Plante et al. | |
| 2008/0227162 A1 | 9/2008 | Varanasi et al. | |
| 2008/0227166 A1 | 9/2008 | Allain et al. | |
| 2008/0249339 A1 | 10/2008 | Stokes et al. | |
| 2008/0274523 A1 | 11/2008 | Renninger et al. | |
| 2008/0293109 A1 | 11/2008 | Berka et al. | |
| 2008/0299628 A1 | 12/2008 | Hallberg et al. | |
| 2009/0011480 A1 | 1/2009 | Trimbur et al. | |
| 2009/0017503 A1 | 1/2009 | Zhang et al. | |
| 2009/0042259 A1 | 2/2009 | Dale et al. | |
| 2009/0068714 A1 | 3/2009 | Leschine et al. | |
| 2009/0286294 A1 | 11/2009 | Blanchard et al. | |
| 2010/0028966 A1 | 2/2010 | Blanchard et al. | |
| 2010/0086981 A1 | 4/2010 | Latouf et al. | |
| 2010/0105114 A1 | 4/2010 | Blanchard et al. | |

FOREIGN PATENT DOCUMENTS

| | | |
|---|---|---|
| GB | 1552207 | 9/1979 |
| WO | WO 92/16615 | 10/1992 |
| WO | WO 2006/085762 A1 | 8/2006 |
| WO | WO 2007/053600 A2 | 5/2007 |
| WO | WO 2007/130984 A2 | 11/2007 |
| WO | WO 2007/134607 | 11/2007 |
| WO | WO 2008/023060 A1 | 2/2008 |
| WO | WO 2007/130984 A3 | 3/2008 |
| WO | WO 2008/029163 A2 | 3/2008 |
| WO | WO 2007/053600 A3 | 7/2008 |
| WO | WO 2007/130984 A3 | 7/2008 |
| WO | WO 2008/085356 A1 | 7/2008 |
| WO | WO 2008/029163 A3 | 8/2008 |
| WO | WO 2008/095098 A2 | 8/2008 |
| WO | WO 2008/134259 A1 | 11/2008 |
| WO | WO 2008/135783 A1 | 11/2008 |
| WO | WO 2008/141174 | 11/2008 |
| WO | WO 2009/027638 A1 | 3/2009 |
| WO | WO 2010/014631 | 2/2010 |
| WO | WO 2010/014632 | 2/2010 |

OTHER PUBLICATIONS

S. Leschine, "Biomass to Biofuel Technology: A Novel Bacterial Catalyst for Consolidated Bioprocessing of Biomass to Ethanol," The Institute for Massachusetts Biofuels Research (TIMBR), University of Massachusetts Amherst, Jan. 2007.*

(Continued)

*Primary Examiner* — Rebecca Prouty
(74) *Attorney, Agent, or Firm* — Milstein Zhang & Wu LLC

(57) ABSTRACT

Methods and compositions are provided for improving the production of products, such as fuel products like ethanol, in microorganisms. In particular, methods and compositions are described for improving ethanol production utilizing genes identified in *Clostridium phytofermentans*.

25 Claims, 19 Drawing Sheets

OTHER PUBLICATIONS

L.R. Lynd et al. "Consolidated bioprocessing of cellulosic biomass: an update," Curt. Opin. Biotechnol., 16:577-583 (2005).*
GenBank Accesion No. CP000885 *Clostridium phytofermentans* ISDg, complete genome (Nov. 2007).*
S. Leschine. "Cellulose Degradation in Anaerobic Environments", Ann. Review Microbiol. 49:399-426. (1995).*
S. Leschine. "Microbial Physiology and Diversity: Cellulose and Chitin Decomposition, Biofilms on Natural Polymers, Fuels From Biomass.", Department of Microbiology, Univ. Of Mass. (Jan. 2, 2006). Available at http://www.bio.umass.edu/micro/faculty/leschine.html.*
U.S. Appl. No. 12/720,574, filed Mar. 9, 2010, Parekh et al.
U.S. Appl. No. 12/729,037, filed Mar. 22, 2010, Schmalisch et al.
U.S. Appl. No. 12/763,996, filed Apr. 20, 2010, Parekh et al.
Bjerre, " Pretreatment of Wheat Straw using Combined Wet Oxidation and Alkaline Hydrolysis Resulting in Convertible Cellulose and Hemicellulose", Biotechnology and Bioengineering, vol. 49, pp. 568-577, 1996.
Desvaux et al., "Cellulose Catabolism by *Clostridium cellulolyticum* Growing in Batch Culture on Defined Medium", Applied and Environmental Microbiology, vol. 66, No. 6, pp. 2461-2470, 2000.
Greer, "Creating Cellulosic Ethanol—Spinning Straw Into Fuel," BioCycle, 61-65 (2005).
International Search Report and Written Opinion dated Mar. 3, 2010 for PCT Application PCT/US09/047086.
International Search Report dated Mar. 15, 2010 for PCT Application No. PCT/US09/051992.
International Search Report dated Apr. 16, 2010 for PCT Application No. PCT/US10/26730.
International Search Report and Written Opinion dated Jun. 30, 2010 for PCT Application PCT/US10/031796.
International Search Report dated Oct. 1, 2008 for PCT Application No. PCT/US07/02334.
Juhasz, et al. "Production of β-Glucosidase in Mixed Culture of *Aspergillus niger* BKMF 1305 and *Trichoderma reesei* RUT C3O", Food Tech. Biotechnol. 41 (1), pp. 49-53, 2003.
Kim et al., "Effects of Pressing Lignocellulosic Biomass on Sugar Yield in Two-Stage Dilute-Acid Hydrolysis Process", Biotechnol. Prog., 18, pp. 489-494, 2002.
Knauf et al., "Lignocellulosic biomass processing: A perspective," Int. Sugar Journal 106(1263): 147-150 (2004).
Leschine et al., "Ethanol Production from Celluolose by a Coculture of *Zymomonas mobilis* and a Clostridum", Current Microbiology, vol. II, pp. 129-136, 1984.
Leschine, "A novel biocatalyst for Cellulosic Ethanol Production", First Annual TIMBR Conference on Cellulosic Biofuels, University of Massachusetts Amherst, Sep. 19, 2008.
Leschine, "A novel microbial catalyst for advanced biofuel production" Advanced Biofuels Workshop and Trade Show, Minneapolis, Aug. 12, 2008.
Leschine, "*Clostridium phytofermentans*: A novel catalyst for cellulosic ethanol production" Georgia State University Biotechnology Symposium, Atlanta Aug. 14, 2008.
Leschine, "The diversity of soil microbes holds the key to advancing bioenergy production". Geological. Society of America Joint Meeting, Houston, October 8, 2008.
Leschine, "A novel consolidated bioprocessing technology for biomass ethanol production", Biotechnology Industry Organization (Bio), Pacific Rim Conference, Honolulu, Nov. 15, 2007.
Leschine, "A Novel Microbial Catalyst for Cellulosic Ethanol Production", Agriculture and Energy Seminar Series, USDA, Washington, D.C., Jan. 23, 2008.
Leschine, "Biomass to Biofuel Technology: A Novel Bacterial Catalyst for Consolidated Bioprocessing of Biomass to Ethanol". The Institute for Massachusetts Biofuels Research (TIMBR) University of Massachusetts Amherst, Jan. 2007.
Leschine, "Testimony of Susan Leschine", Testimony Before the Select Committee on Energy Independence and Global Warming, Hearing on The Gas is Greener: the Future of Biofuels, Oct. 24. 2007.
Lynd et al. in "Consolidated Bioprocessing of Cellulosic Biomass: An Update," Current Opinion in Biotechnology, 16:577-583, 2005.
Lynd et al., "Microbial cellulose utilization: fundamentals and biotechnology," Microbiol. Mol. Biol. Rev. 66(3):506-77 (2002), table of contents. Review. Erratum in: Microbiol. Mol. Biol. Rev. Dec. 2002; 66(4):739.
Mai et al., "Advances in Development of a Genetic System for Thermoanaerobacerium spp.: Expression of Genes Encoding Hydrolytic Enzymes, Development of a Second Shuttle Vector, and Integration of Genes into the Chromosome", Applied and Environmental Microbiology, pp. 4817-4821, Nov. 2000.
Martin et al., "Ethanol production from enzymatic hydrolysates of sugarcane bagasse using recombinant xylose-utilising *Saccharomyes cerevisiae*", Enzyme and Microbial Technology, 31:274-282, 2002.
Mosier et al., "Features of promising technologies for pretreatment of lignocellulose biomass", Bioresource Technology, 96,673-686, 2005.
Ralph, "Lignin Structure: Recent Developments." (US Dairy Forage Research Center, USDA-Agricultural Research Service), (1999).
Shaw et al., "Metabolic Engineering of the Xylose Utilizing Thermophile Thermoanaerobacerium Saccharolyticum Jw/S1-Ys485 for Ethanol Production", Advances in Metabolic Engineering and Bioinformatics: From Prokaryotes to Eukaryotes The Preliminary Program for 2005 Annual Meeting (Cincinnati, OH) (abstract only).
Sheehan et al., "Enzymes, Energy, and the Environment: A Strategic Perspective on the U.S. Department of Energy's Research and Development Activities for Bioethanol", Biotechnology Progress, 15pp. 817-827, 1999.
Stackebrandt et al., "Taxonomic Note: A Place for DNA-DNA Reassociation and 16S rRNA Sequence Analysis in the Present Species Definition in Bacteriology," Int. J. Sys. Bact. 44(4):846-849 (1994).
Wackett et al., "Microbial-based Motor Fuels: Science and Technology," Microbial Biotechnology (2008) doi: 10.1111/j.1751-7915. 2007.00020.x pp. 1-15.
Warnick et al., "*Clostridium phytofermentans* sp. nov., a cellulolytic mesophile from forest soil," Int. J. Syst. Evol. Microbiol. 52(Pt 4):1155-1160 (2002).
Wolin et al., "Viologen Dye Inhibition of Methane Formation by *Methanobacillus omelianskii*", Journal of Bacteriology, 87:993, pp. 993-998, 1964.
Int'l preliminary Report on Patentability & Written Opinion of the Int'l Searching Authority, PCT/US2009/051992, Date of mailing Feb. 10, 2011.
Int'l preliminary Report on Patentability & Written Opinion of the Int'l Searching Authority, PCT/US2009/051993, Date of mailing Feb. 10, 2011.
PCT/US2009/051993 international search report mailed Apr. 30, 2010.
PCT/US2009/047086 international search report mailed Mar. 3, 2010.
PCT/US2009/039685 international search report mailed Jul. 28, 2009.
PCT/US2009/035597 international search report mailed Jun. 26, 2009.
GB 1001956.0 search and examination report mailed Jun. 2, 2010.
GB 1004631.6 search and examination report mailed Apr. 1, 2010.
Alsaker et al., Transcriptional analysis of spo0A overexpression in *Clostridium acetobutylicum* and its effect on the cell's response to butanol stress, J Bacteriol. Apr. 2004;186(7):1959-71.
Alsaker et al., Transcriptional program of early sporulation and stationary-phase events in *Clostridium acetobutylicum*, J Bacteriol. Oct. 2005;187(20):7103-18.
Alsaker, Design, optimization and validation of genomic DNA microarrays for examining the *Clostridium acetobutylicum* trascriptome, Biotechnol Bioprocess Eng 2005 10:432-443.
Boiangiu et al., Sodium ion pumps and hydrogen production in glutamate fermenting anaerobic bacteria, J Mol Microbiol Biotechnol. 2005 10(2-4):105-19.
Brueggemann, The genome sequence of *Clostridium tetani*, the causative agent of tetanus disease, PNAS 2003 100:1316-1321.

Harris et al., Northern, morphological, and fermentation analysis of spo0A inactivation and overexpression in *Clostridium acetobutylicum* ATCC 824, J Bacteriol. Jul. 2002;184(13):3586-97.

Kato, Effective cellulose degradation by a mixed-culture system composed of a cellulolytic *Clostridium* and aerobic non-cellulolytic bacteria, FEMS Microbiology Ecology 2004 51:133-142.

Li et al., Electron transport in the pathway of acetate conversion to methane in the marine archaeon *Methanosarcina acetivorans*, J Bacteriol. Jan. 2006;188(2):702-10.

Ng et al., Ethanol Production by Thermophilic Bacteria: Fermentation of Cellulosic Substrates by Cocultures of *Clostridium thermocellum* and *Clostridium thermohydrosulfuricum*, Appl Environ Microbiol. Jun. 1981;41(6):1337-43.

Paredes et al., A comparative genomic view of clostridial sporulation and physiology, Nat Rev Microbiol. Dec. 2005;3(12):969-78.

Ren et al., Characterization of the cellulolytic and hydrogen-producing activities of six mesophilic *Clostridium* species, J Appl Microbiol. Dec. 2007;103(6):2258-66.

Sun et al., Hydrolysis of lignocellulosic materials for ethanol production: a review, Bioresource Technology 2002 83:1-11.

Tolonen et al., Targeted gene inactivation in *Clostridium phytofermentans* shows that cellulose degradation requires the family 9 hydrolase Cphy3367, Mol Microbiol. Dec. 2009;74(6):1300-13.

* cited by examiner

Specific examples in Cphy related to cellulose and xylan

| 2272 | 2273 | 2274 | | 2276 |

| 3212 | 3211 | 3210 | 3209 | 3208 | | 3207 |

| 0863 | 0864 | 0862 | 0861 | 0860 |

| 2467 | 2464 | 2465 | 2464 |

| 1876 | | 1877 |

FIG. 2

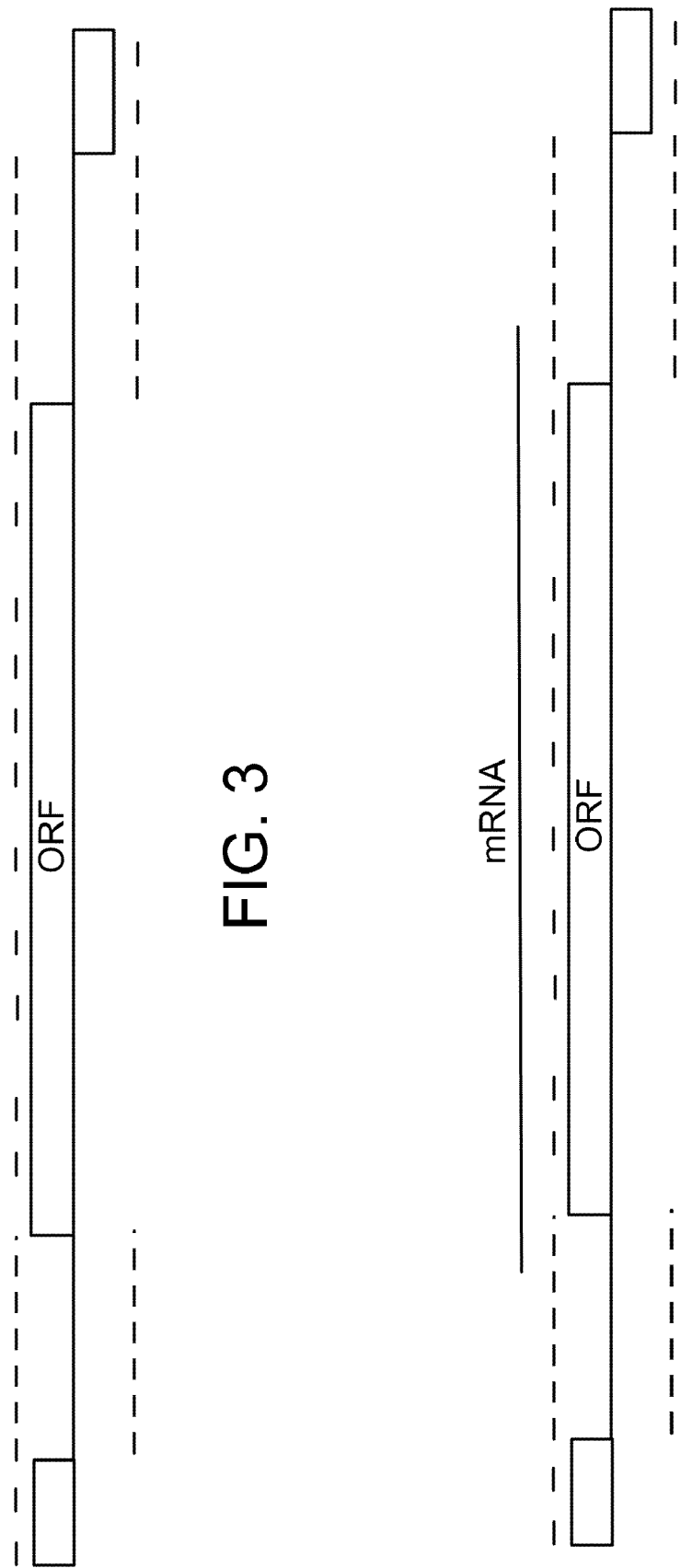

EXTRACELLULAR HYDROLASES

- CPHYDRAFT_0995: CELLULASE
  -CELLULASE(GH5) –

- CPHYDRAFT_1460: CELLULASE
  CELLULASE(GH5) DUF291 CBDII

- CPHYDRAFT_2150: CELLULASE
  CELLULASE(GH5)

- CPHYDRAFT_0560: MANNAN ENDO-1,4- -MANNOSIDASE
  CBM6 GH26 CBM3

- CPHYDRAFT_3622: MANNAN ENDO-1,4- -MANNOSIDASE
  – GH26 –DUF291–DUF291 CBM3 –

- CPHYDRAFT_2095: MANNAN ENDO-1,4- -MANNOSIDASE
  GH26

- CPHYDRAFT_2913: ENDO-1,4- -XYLANASE
  XYNA (GH10) XYNA (GH10)

- CPHYDRAFT_1307: ENDOGLUCANASE
  GH12

- CPHYDRAFT_1110: ENDO-1,3 (1,4)- -GLUCANASE
  GH16 –CBM4_9–CBM4_9–CBM4_9–CBM4_9–CBM4_9– BIG2 –

MEMBRANE-BOUND HYDROLASES

- CPHYDRAFT_1067: ENDO-(EXO)-GLUCANASE     CPHYDRAFT_1068:EXOGLUCANASE
  – GH9 – CBM3 –DUF291–DUF291 CBM3 — ..... GH48 DUF291 CBM3 –

- CPHYDRAFT_2095: MANNAN ENDO-1,4- -MANNOSIDASE
  GH26

- CPHYDRAFT_3365: ENDO- -N-ACETYLGLUCOSAMINIDASE D
  GH85 PKD F5F8

- CPHYDRAFT_0433:        CPHYDRAFT_0434:             CPHYDRAFT_0435:
  XYLANASE              GLYCOSIDE HYDROLASE         ENDO-1,4- -XYLOSIDASE
  –XYNB (GH43)–· · · · ·– GH3 – GH3C –· · · · · · · ·–XYNA (GH10) –

- CPHYDRAFT_1793: ENDO-1,4- -XYLANASE
  XYNA (GH10)

- CPHYDRAFT_3641: ENDO-1,4- -XYLANASE
  XYNA(GH10) CBM4_9

- CPHYDRAFT_3644: ENDO-1,4- -XYLANASE
  GH11

- CPHYDRAFT_1850: PUTATIVE PECTINASE
  GH28

- CPHYDRAFT_0239: PUTATIVE PECTINASE
  – GH28 –

- CPHYDRAFT_1555: GLYCOSIDE HYDROLASE
  – GH3 – GH3C –

▬▬ CARBOHYDRATE BINDING DOMAIN
  ▬▬ IG-LIKE DOMAIN
  ▬▬ CATALYTIC DOMAIN DEGRADING CELLULOSE
  ▬▬ CATALYTIC DOMAIN DEGRADING XYLAN
  ▬▬ CATALYTIC DOMAIN DEGRADING MANNAN
  ▬▬ CATALYTIC DOMAIN DEGRADING PECTIN
  ▬▬ OTHER CATALYTIC DOMAIN DEGRADING PLANT CELL WALL COMPONENTS
  ▬▬ SINGLE PEPTIDE CLEAVAGE (ABOUT 50 DIVERSE AND NUMEROUS SUGAR ABC-TYPE TRANSPORTERS SYSTEMS)

FIG. 12

METHODS AND COMPOSITIONS FOR IMPROVING THE PRODUCTION OF PRODUCTS IN MICROORGANISMS

CLAIM OF PRIORITY

This application claims the benefit of priority from U.S. Provisional Patent Application Ser. No. 61/084,233, filed on Jul. 28, 2008, U.S. Provisional Patent Application Ser. No. 61/225,184 filed on Jul. 13, 2009, and U.S. Provisional Patent Application Ser. No. 61/228,922, filed on Jul. 27, 2009, and the entire contents of all of which are incorporated by reference herein.

FIELD OF THE INVENTION

The present invention relates to the field of microbiology, molecular biology and biotechnology. More specifically, the present invention relates to methods and compositions for improving the production of products, such as ethanol and hydrogen, in microorganisms.

BACKGROUND

There is an interest in developing methods and compositions for producing usable energy from renewable and sustainable biomass resources. Energy in the form of carbohydrates can be found in waste biomass, and in dedicated energy crops, for example, grains, such as corn or wheat, or grasses, such as switchgrass.

A current challenge is to develop viable and economical strategies for the conversion of carbohydrates into usable energy forms. Strategies for deriving useful energy from carbohydrates include the production of ethanol and other alcohols, conversion of carbohydrates into hydrogen, and direct conversion of carbohydrates into electrical energy through fuel cells. Examples of strategies to derive ethanol form biomass are described by DiPardo, *Journal of Outlook for Biomass Ethanol Production and Demand* (EIA Forecasts), 2002; Sheehan, *Biotechnology Progress*, 15:8179, 1999; Martin, *Enzyme Microbes Technology*, 31:274, 2002; Greer, *BioCycle*, 61-65, April 2005; Lynd, *Microbiology and Molecular Biology Reviews*, 66:3, 506-577, 2002; and Lynd et al. in "Consolidated Bioprocessing of Cellulosic Biomass: An Update," *Current Opinion in Biotechnology*, 16:577-583, 2005.

SUMMARY

This application is based, inter alia, on the identification of *Clostridium phytofermentans* genes encoding products predicted to be involved in growth on substrates useful for production of products, such as fuels, e.g., ethanol and hydrogen. The genes identified herein can be expressed heterologously in other microorganisms to provide new or enhanced functions. Also, the genes can be expressed in *C. phytofermentans*, e.g., from an exogenously introduced nucleic acid, to provide enhanced functions.

Some embodiments include polynucleotides containing an isolated nucleic acid encoding at least one hydrolase identified in *C. phytofermentans*. In such embodiments, the isolated nucleic acid can be selected from Table 6. In particular embodiments, the hydrolase is selected from the group consisting of Cphy3367, Cphy3368, Cphy0430, Cphy3854, Cphy0857, Cphy0694, and Cphy1929. The designation Cphy3367 represents the JGI number, which refers to the National Center for Biotechnology Information (NCBI) locus tag on the GenBank record for *C. phytofermentans* In further embodiments, the polynucleotide can contain a regulatory sequence operably linked to the isolated nucleic acid encoding the hydrolase.

Some embodiments include polynucleotides containing an isolated nucleic acid encoding at least one ATP-binding cassette (ABC)-transporter identified in *C. phytofermentans*. In such embodiments, the isolated nucleic acid can be selected from Table 7. In particular embodiments, the ABC-transporter is selected from the group consisting of Cphy3854, Cphy3855, Cphy3857, Cphy3858, Cphy3859, Cphy3860, Cphy3861, and Cphy3862. In further embodiments, the polynucleotide can contain a regulatory sequence operably linked to the isolated nucleic acid encoding the ABC-transporter.

Some embodiments include polynucleotides containing an isolated nucleic acid encoding at least one transcriptional regulator identified in *C. phytofermentans*. In such embodiments, the isolated nucleic acid can be selected from Table 8. In further embodiments, the polynucleotide can contain a regulatory sequence operably linked to the isolated nucleic acid encoding the transcriptional regulator.

Some embodiments include polynucleotide cassettes containing any combination of the nucleic acids encoding hydrolases, ABC-transporters, and transcriptional regulators described herein. In one embodiment, a polynucleotide cassette can contain an isolated nucleic acid encoding at least one hydrolase, and an isolated nucleic acid encoding at least one ABC-transporter. In another embodiment, a polynucleotide cassette can contain an isolated nucleic acid encoding at least one hydrolase, and an isolated nucleic acid encoding at least one transcriptional regulator. In another embodiment, a polynucleotide cassette can contain an isolated nucleic acid encoding at least one ABC-transporter, and an isolated nucleic acid encoding at least one transcriptional regulator. In yet another embodiment, a polynucleotide cassette can contain an isolated nucleic acid encoding at least one hydrolase, and an isolated nucleic acid encoding at least one ABC-transporter, and an isolated nucleic acid encoding at least one transcriptional regulator.

Some embodiments include expression cassettes containing any polynucleotide described herein and a regulatory sequence operably linked to the polynucleotide cassette.

Some embodiments include recombinant microorganisms containing any polynucleotide, polynucleotide cassette, and/or expression cassette described herein. In particular embodiments, the recombinant microorganism can be selected from the group consisting of *Clostridium cellulovorans, Clostridium cellulolyticum, Clostridium thermocellum, Clostridium josui, Clostridium papyrosolvens, Clostridium cellobioparum, Clostridium hungatei, Clostridium cellulosi, Clostridium stercorarium, Clostridium termitidis, Clostridium thermocopriae, Clostridium celerecrescens, Clostridium polysaccharolyticum, Clostridium populeti, Clostridium lentocellum, Clostridium chartatabidum, Clostridium aldrichii, Clostridium herbivorans, Acetivibrio cellulolyticus, Bacteroides cellulosolvens, Caldicellulosiruptor saccharolyticum, Ruminococcus albus, Ruminococcus flavefaciens, Fibrobacter succinogenes, Eubacterium cellulosolvens, Butyrivibrio fibrisolvens, Anaerocellum thermophilum, Halocella cellulolytica, Thermoanaerobacterium thermosaccharolyticum* and *Thermoanaerobacterium saccharolyticum*.

Some embodiments include isolated proteins encoding a hydrolase identified in *C. phytofermentans*. In some embodiments, methods are provided for producing ethanol. Such methods include culturing a microorganism; supplying a substrate; and supplying any isolated protein described herein.

Some embodiments include isolated polynucleotide cassettes that include one or more, two or more, or all three of: a sequence encoding a *Clostridium phytofermentans* hydrolase, a sequence encoding a *C. phytofermentans* ATP-binding cassette (ABC) transporter, and a sequence encoding a *C. phytofermentans* transcriptional regulator. In some embodiments, the hydrolase is selected from the group consisting of Cphy3368, Cphy3367, Cphy1799, Cphy1800, Cphy2105, Cphy1071, Cphy0430, Cphy1163, Cphy3854, Cphy1929, Cphy2108, Cphy3158, Cphy3207, Cphy3009, Cphy3010, Cphy2632, Cphy3586, Cphy0218, Cphy0220, Cphy1720, Cphy3160, Cphy2276, Cphy1714, Cphy0694, Cphy3202, Cphy3862, Cphy0858, Cphy1510, Cphy2128, Cphy1169, Cphy1888, Cphy2919, and Cphy1612. In some embodiments, the ABC transporter is selected from the group consisting of Cphy1529, Cphy1530, Cphy1531, Cphy3858, Cphy3859, Cphy3860, Cphy2569, Cphy2570, Cphy2571, Cphy2654, Cphy2655, Cphy2656, Cphy3588, Cphy3589, Cphy3590, Cphy3210, Cphy3209, Cphy3208, Cphy2274, Cphy2273, Cphy2272, Cphy2268, Cphy2267, Cphy2266, Cphy2265, Cphy2012, Cphy2011, Cphy2010, Cphy2009, Cphy1717, Cphy1716, Cphy1715 Cphy1451, Cphy1450, Cphy1449, Cphy1448, Cphy1134, Cphy1133, and Cphy1132.

Some embodiments include recombinant microorganisms that include a nucleic acid disclosed herein, e.g., one or more, two or more, or all three of: an exogenous nucleic acid encoding a *Clostridium phytofermentans* hydrolase, an exogenous nucleic acid encoding a *C. phytofermentans* ATP-binding cassette (ABC) transporter, and an exogenous nucleic acid encoding a *C. phytofermentans* transcriptional regulator. In some embodiments, the hydrolase is selected from the group consisting of Cphy3368, Cphy3367, Cphy1799, Cphy1800, Cphy2105, Cphy1071, Cphy0430, Cphy1163, Cphy3854, Cphy1929, Cphy2108, Cphy3158, Cphy3207, Cphy3009, Cphy3010, Cphy2632, Cphy3586, Cphy0218, Cphy0220, Cphy1720, Cphy3160, Cphy2276, Cphy1714, Cphy0694, Cphy3202, Cphy3862, Cphy0858, Cphy1510, Cphy2128, Cphy1169, Cphy1888, Cphy2919, and Cphy1612. In some embodiments, the ABC transporter is selected from the group consisting of Cphy1529, Cphy1530, Cphy1531, Cphy3858, Cphy3859, Cphy3860, Cphy2569, Cphy2570, Cphy2571, Cphy2654, Cphy2655, Cphy2656, Cphy3588, Cphy3589, Cphy3590, Cphy3210, Cphy3209, Cphy3208, Cphy2274, Cphy2273, Cphy2272, Cphy2268, Cphy2267, Cphy2266, Cphy2265, Cphy2012, Cphy2011, Cphy2010, Cphy2009, Cphy1717, Cphy1716, Cphy1715 Cphy1451, Cphy1450, Cphy1449, Cphy1448, Cphy1134, Cphy1133, and Cphy1132. In some embodiments, the microorganism is selected from the group consisting of *Clostridium cellulovorans, Clostridium cellulolyticum, Clostridium thermocellum, Clostridium josui, Clostridium papyrosolvens, Clostridium cellobioparum, Clostridium hungatei, Clostridium cellulosi, Clostridium stercorarium, Clostridium termitidis, Clostridium thermocopriae, Clostridium celerecrescens, Clostridium polysaccharolyticum, Clostridium populeti, Clostridium lentocellum, Clostridium chartatabidum, Clostridium aldrichii, Clostridium herbivorans, Acetivibrio cellulolyticus, Bacteroides cellulosolvens, Caldicellulosiruptor saccharolyticum, Ruminococcus albus, Ruminococcus flavefaciens, Fibrobacter succinogenes, Eubacterium cellulosolvens, Butyrivibrio fibrisolvens, Anaerocellum thermophilum, Halocella cellulolytica, Thermoanaerobacterium thermosaccharolyticum* and *Thermoanaerobacterium saccharolyticum.*

Some embodiments include methods for producing ethanol that include culturing at least one recombinant microorganism described herein. Such embodiments, can also include supplying a substrate to the microorganism. In particular embodiments, the substrate can be selected from the group consisting of saw dust, wood flour, wood pulp, paper pulp, paper pulp waste steams, grasses, such as, switchgrass, biomass plants and crops, such as, crambe, algae, rice hulls, bagasse, jute, leaves, macroalgae matter, microalgae matter, grass clippings, corn stover, corn cobs, corn grain, corn grind, distillers grains, and pectin. In certain embodiments, the substrate can be pectin.

Some embodiments include methods for processing a substrate of a hydrolase that include providing a microorganism that exogenously expresses a *Clostridium phytofermentans* hydrolase; and supplying the substrate of the hydrolase to the microorganism, such that the substrate is processed to form a product. In some embodiments, the microorganism exogenously expresses a *Clostridium phytofermentans* ATP-binding cassette (ABC) transporter that transports (e.g., imports or exports) the product.

Some embodiments include a product for production of a biofuel that includes a lignocellulosic biomass and a microorganism that is capable of direct hydrolysis and fermentation of said biomass, wherein the microorganism is modified to provide enhanced activity of one or more cellulases (e.g., one or more cellulases disclosed herein, e.g., Cphy3367, Cphy3368, Cphy0218, Cphy3207, Cphy2058, and Cphy1163). In some embodiments, the microorganism is capable of direct fermentation of five carbon and six carbon sugars. In some embodiments, the microorganism is a bacterium, e.g., a species of *Clostridium*, e.g., *Clostridium phytofermentans*. In some embodiments, the microorganism comprises one or more heterologous polynucleotides that enhance that activity of one or more cellulases.

Some embodiments include a product for production of a biofuel that includes a carbonaceous biomass and a microorganism that is capable of direct hydrolysis and fermentation of said biomass, wherein said microorganism is modified to provide enhanced activity of one or more cellulases (e.g., one or more cellulases disclosed herein, e.g., Cphy3367, Cphy3368, Cphy0218, Cphy3207, Cphy2058, and Cphy1163). In some embodiments, the microorganism is capable of producing fermentive end products. In some embodiments, a substantial portion of the fermentive end products is ethanol. In some embodiments, the fermentive end products include lactic acid, acetic acid, and/or formic acid. In some embodiments, the microorganism is capable of uptake of one or more complex carbohydrates. In some embodiments, the biomass has a higher concentration of oligomeric carbohydrates relative to monomeric carbohydrates.

Some embodiments include a process for producing a biofuel that includes (a) contacting a carbonaceous biomass with a microorganism that is capable of direct hydrolysis and fermentation of said biomass, wherein the microorganism is modified to enhance activity of one or more cellulase enzymes (e.g., one or more cellulases disclosed herein, e.g., Cphy3367, Cphy3368, Cphy0218, Cphy3207, Cphy2058, and Cphy1163); and (b) allowing sufficient time for said hydrolysis and fermentation to produce a biofuel. In some embodiments, the microorganism is capable of uptake of one or more complex carbohydrates. In some embodiments, the biomass has a higher concentration of oligomeric carbohydrates relative to monomeric carbohydrates. In some embodiments, the hydrolysis results in a greater concentration of cellobiose and/or larger oligomers, relative to monomeric carbohydrates.

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to metrics such as temperatures, concentrations, and times discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the invention. The articles "a" and "an" are used herein to refer to one or to more than one (i.e., to at least one) of the grammatical object of the article. By way of example, "an element" means one element or more than one element.

Unless otherwise defined, scientific and technical terms used in connection with the invention described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. 2000). The nomenclatures utilized in connection with, and the laboratory procedures and techniques of described herein are those well known and commonly used in the art.

As utilized in accordance with the embodiments provided herein, the following terms, unless otherwise indicated, shall be understood to have the following meanings:

"Nucleotide" refers to a phosphate ester of a nucleoside, as a monomer unit or within a nucleic acid. "Nucleotide 5'-triphosphate" refers to a nucleotide with a triphosphate ester group at the 5' position, and are sometimes denoted as "NTP" or "dNTP" and "ddNTP" to particularly point out the structural features of the ribose sugar. The triphosphate ester group can include sulfur substitutions for the various oxygens, e.g. α-thio-nucleotide 5'-triphosphates. For a review of nucleic acid chemistry, see: Shabarova, Z. and Bogdanov, A. Advanced Organic Chemistry of Nucleic Acids, VCH, New York, 1994.

The term "nucleic acid" and "nucleic acid molecule" refer to natural nucleic acid sequences such as DNA (deoxyribonucleic acid) and RNA (ribonucleic acid), artificial nucleic acids, analogs thereof, or combinations thereof.

As used herein, the terms "polynucleotide" and "oligonucleotide" are used interchangeably and mean single-stranded and double-stranded polymers of nucleotide monomers (nucleic acids), including, but not limited to, 2'-deoxyribonucleotides (nucleic acid) and ribonucleotides (RNA) linked by internucleotide phosphodiester bond linkages, e.g. 3'-5' and 2'-5', inverted linkages, for example, 5'-5', branched structures, or analog nucleic acids. Polynucleotides have associated counter ions, such as $H^+$, $NH4^+$, trialkylammonium, $Mg^{2+}$, $Na^+$ and the like. A polynucleotide can be composed entirely of deoxyribonucleotides, entirely of ribonucleotides, or chimeric mixtures thereof. Polynucleotides can be comprised of nucleobase and sugar analogs. Polynucleotides typically range in size from a few monomeric units, for example, 5-40 when they are more commonly frequently referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine "Fuels and/or other chemicals" is used herein to refer to compounds suitable as liquid or gaseous fuels including, but not limited to hydrocarbons, hydrogen, methane, hydroxy compounds such as alcohols (e.g. ethanol, butanol, propanol, methanol, etc.), carbonyl compounds such as aldehydes and ketones (e.g. acetone, formaldehyde, 1-propanal, etc.), organic acids, derivatives of organic acids such as esters (e.g. wax esters, glycerides, etc.) and other functional compounds including, but not limited to, 1,2-propanediol, 1,3-propanediol, lactic acid, formic acid, acetic acid, succinic acid, and pyruvic acid, produced by enzymes such as cellulases, polysaccharases, lipases, proteases, ligninases, and hemicellulases.

The term "plasmid" refers to a circular nucleic acid vector. Generally, plasmids contain an origin of replication that allows many copies of the plasmid to be produced in a bacterial (or sometimes eukaryotic) cell without integration of the plasmid into the host cell DNA.

The term "construct" as used herein refers to a recombinant nucleotide sequence, generally a recombinant nucleic acid molecule, that has been generated for the purpose of the expression of a specific nucleotide sequence(s), or is to be used in the construction of other recombinant nucleotide sequences. In general, "construct" is used herein to refer to a recombinant nucleic acid molecule.

An "expression cassette" refers to a set of polynucleotide elements that permit transcription of a polynucleotide in a host cell. Typically, the expression cassette includes a promoter and a heterologous or native polynucleotide sequence that is transcribed. Expression cassettes or constructs may also include, e.g., transcription termination signals, polyadenylation signals, and enhancer elements.

By "expression vector" is meant a vector that permits the expression of a polynucleotide inside a cell. Expression of a polynucleotide includes transcriptional and/or post-transcriptional events. An "expression construct" is an expression vector into which a nucleotide sequence of interest has been inserted in a manner so as to be positioned to be operably linked to the expression sequences present in the expression vector.

An "operon" refers to a set of polynucleotide elements that produce a messenger RNA (mRNA). Typically, the operon includes a promoter and one or more structural genes. Typically, an operon contains one or more structural genes which are transcribed into one polycistronic mRNA: a single mRNA molecule that encodes more than one protein. In some embodiments, an operon may also include an operator that regulates the activity of the structural genes of the operon.

The term "host cell" as used herein refers to a cell that is to be transformed using the methods and compositions of the invention. In general, host cell as used herein means a microorganism cell into which a nucleic acid of interest is introduced.

The term "transformation" as used herein refers to a permanent or transient genetic change, e.g., a permanent genetic change, induced in a cell following incorporation of non-host nucleic acid sequences.

The term "transformed cell" as used herein refers to a cell into which (or into an ancestor of which) has been introduced, by means of recombinant nucleic acid techniques, a nucleic acid molecule encoding a gene product of interest, for example, RNA and/or protein.

The term "gene" as used herein refers to any and all discrete coding regions of a host genome, or regions that encode a functional RNA only (e.g., tRNA, rRNA, regulatory RNAs such as ribozymes) and includes associated non-coding regions and regulatory regions. The term "gene" includes within its scope open reading frames encoding specific polypeptides, introns, and adjacent 5' and 3' non-coding nucleotide sequences involved in the regulation of expression. In this regard, a gene may further comprise control signals such as promoters, enhancers, and/or termination signals that are naturally associated with a given gene, or heterologous control signals. A gene sequence may be cDNA or genomic nucleic acid or a fragment thereof. A gene may be introduced into an appropriate vector for extrachromosomal maintenance or for integration into the host.

The term "gene of interest," "nucleotide sequence of interest" "polynucleotide of interest" or "nucleic acid of interest" as used herein refers to any nucleotide or nucleic acid sequence that encodes a protein or other molecule that is desirable for expression in a host cell (e.g., for production of the protein or other biological molecule (e.g., an RNA product) in the target cell). The nucleotide sequence of interest can be operatively linked to other sequences which facilitate expression, e.g., a promoter.

The term "promoter" as used herein refers to a minimal nucleic acid sequence sufficient to direct transcription of a nucleic acid sequence to which it is operably linked. The term "inducible promoter" as used herein refers to a promoter that is transcriptionally active when bound to a transcriptional activator, which in turn is activated under a specific condition(s), e.g., in the presence of a particular chemical signal or combination of chemical signals that affect binding of the transcriptional activator to the inducible promoter and/or affect function of the transcriptional activator itself.

The terms "operator," "control sequences," or "regulatory sequence," as used herein refer to nucleic acid sequences that regulate the expression of an operably linked coding sequence in a particular host organism. The control sequences that are suitable for prokaryotes, for example, include a promoter, optionally an operator sequence, and a ribosome binding site.

By "operably connected" or "operably linked" and the like is meant a linkage of polynucleotide elements in a functional relationship. A nucleic acid sequence is "operably linked" when it is placed into a functional relationship with another nucleic acid sequence. For instance, a promoter or enhancer is operably linked to a coding sequence if it affects the transcription of the coding sequence. In some embodiments, operably linked means that the nucleic acid sequences being linked are typically contiguous and, where necessary to join two protein coding regions, contiguous and in reading frame. A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences are ultimately processed to produce the desired protein.

"Operably connecting" a promoter to a transcribable polynucleotide means placing the transcribable polynucleotide under the regulatory control of a promoter, which then controls the transcription and optionally translation of that polynucleotide. In the construction of heterologous promoter/structural gene combinations, it is typical to position a promoter or variant thereof at a distance from the transcription start site of the transcribable polynucleotide, which is approximately the same as the distance between that promoter and the gene it controls in its natural setting; namely, the gene from which the promoter is derived. As is known in the art, some variation in this distance can be accommodated without loss of function. Similarly, the typical positioning of a regulatory sequence element such as an operator, enhancer, with respect to a transcribable polynucleotide to be placed under its control is defined by the positioning of the element in its natural setting; namely, the genes from which it is derived.

"Culturing" signifies incubating a cell or organism under conditions wherein the cell or organism can carry out some, if not all, biological processes. For example, a cell that is cultured may be growing or reproducing, or it may be non-viable but still capable of carrying out biological and/or biochemical processes such as replication, transcription, translation, etc.

By "transgenic organism" is meant a non-human organism (e.g., single-cell organisms (e.g., microorganism), mammal, non-mammal (e.g., nematode or *Drosophila*)) having a non-endogenous (i.e., heterologous) nucleic acid sequence present in a portion of its cells or stably integrated into its germ line nucleic acid.

The term "biomass," as used herein refers to a mass of living or biological material and includes both natural and processed, as well as natural organic materials more broadly.

"Recombinant" refers to polynucleotides synthesized or otherwise manipulated in vitro ("recombinant polynucleotides") and to methods of using recombinant polynucleotides to produce gene products encoded by those polynucleotides in cells or other biological systems. For example, a cloned polynucleotide may be inserted into a suitable expression vector, such as a bacterial plasmid, and the plasmid can be used to transform a suitable host cell. A host cell that comprises the recombinant polynucleotide is referred to as a "recombinant host cell" or a "recombinant bacterium." The gene is then expressed in the recombinant host cell to produce, e.g., a "recombinant protein." In addition, a recombinant polynucleotide may serve a non-coding function, for example, promoter, origin of replication, or ribosome-binding site.

The term "homologous recombination" refers to the process of recombination between two nucleic acid molecules based on nucleic acid sequence similarity. The term embraces both reciprocal and nonreciprocal recombination (also referred to as gene conversion). In addition, the recombination can be the result of equivalent or non-equivalent crossover events. Equivalent crossing over occurs between two equivalent sequences or chromosome regions, whereas non-equivalent crossing over occurs between identical (or substantially identical) segments of nonequivalent sequences or chromosome regions. Unequal crossing over typically results in gene duplications and deletions. For a description of the enzymes and mechanisms involved in homologous recombination see, Watson et al., Molecular Biology of the Gene pp 313-327, The Benjamin/Cummings Publishing Co. 4th ed. (1987).

The term "non-homologous or random integration" refers to any process by which nucleic acid is integrated into the genome that does not involve homologous recombination. It appears to be a random process in which incorporation can occur at any of a large number of genomic locations.

A "heterologous polynucleotide sequence" or a "heterologous nucleic acid" is a relative term referring to a polynucleotide that is functionally related to another polynucleotide, such as a promoter sequence, in a manner so that the two polynucleotide sequences are not arranged in the same relationship to each other as in nature. Heterologous polynucleotide sequences include, e.g., a promoter operably linked to a heterologous nucleic acid, and a polynucleotide including its native promoter that is inserted into a heterologous vector for transformation into a recombinant host cell. Heterologous polynucleotide sequences are considered "exogenous" because they are introduced to the host cell via transformation techniques. However, the heterologous polynucleotide can originate from a foreign source or from the same source. Modification of the heterologous polynucleotide sequence may occur, e.g., by treating the polynucleotide with a restriction enzyme to generate a polynucleotide sequence that can be operably linked to a regulatory element. Modification can also occur by techniques such as site-directed mutagenesis.

The term "expressed endogenously" refers to polynucleotides that are native to the host cell and are naturally expressed in the host cell.

"Competent to express" refers to a host cell that provides a sufficient cellular environment for expression of endogenous and/or exogenous polynucleotides.

This application is related to U.S. Provisional Application Ser. No. 61/032,048, filed Feb. 27, 2008; International Application Serial No. PCT/US2009/35597, filed on Feb. 27, 2009; U.S. application Ser. No. 12/419,211, filed on Apr. 6, 2009; U.S. Provisional Application Ser. No. 61/060,620, filed on Jun. 11, 2008; and U.S. application Ser. No. 12/483,118, filed on Jun. 11, 2009, each of which is incorporated herein by reference in its entirety for any purpose.

The following figures, description, and examples illustrate certain embodiments of the present invention in detail. Those of skill in the art will recognize that there are numerous variations and modifications that are encompassed by its scope. Accordingly, the description of certain embodiments should not be deemed to limit the scope of the present invention.

BRIEF DESCRIPTION OF THE DRAWINGS

FIG. 2 is a series of diagrams of specific examples of gene combinations in C. phytofermentans. Numbers represent the location of specific sequences on the chromosome of C. phytofermentans.

FIG. 3 is a diagram of C. phytofermentans Affymetrix microarray design. The dashes represent 24-base probes synthesized on the microarray. The boxes represent predicted open reading frames, for example, protein coding regions. Eleven 24-base probes are used to measure the level of every open reading frame (ORF). The intergenic regions are covered on both sides of the DNA by 24-base probes separated by a single DNA base.

FIG. 4 is a diagram of the method of determination of mRNA transcript boundaries. A hypothetical mRNA transcript includes non-coding regions extending 5' and 3' of the corresponding predicted ORF. Probes are represented by dashes. In this example, three probes to the left (5') of the ORF and two probes to the right (3') of the ORF would indicate mRNA transcript boundaries.

FIG. 12 is a schematic diagram showing example putative hydrolases. Some hydrolases can be extracellular or membrane-bound. GH: Glycoside hydrolases; CBM: Carbohydrate binding domain.

DETAILED DESCRIPTION

Figure 1:
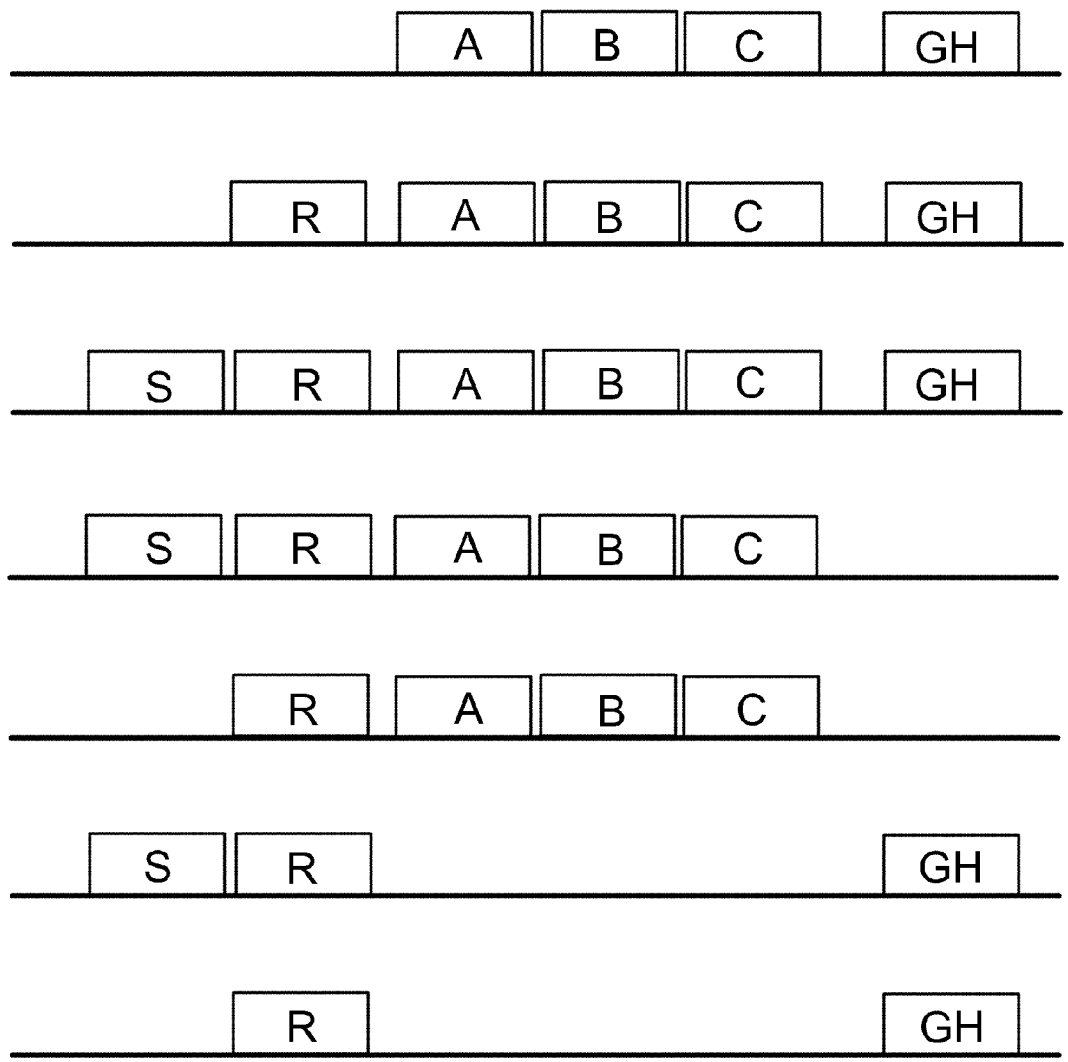
FIG. 1 is a series of diagrams of examples of gene combinations for polynucleotides. R represents a transcriptional regulator sequence; A, B, and C represent sequences encoding an ATP binding cassette (ABC)-transporter; GH represents a sequence encoding a glycoside hydrolase; and S represents signal sequence.

Various embodiments disclosed herein are generally directed towards compositions and methods for making recombinant microorganisms that are capable of producing a fuel when grown under a variety of fermentation conditions. Generally, a recombinant microorganism can efficiently and stably produce a fuel, such as ethanol, and related compounds, so that a high yield of fuel is provided from relatively inexpensive raw biomass materials such as cellulose. In some embodiments, a recombinant microorganism can efficiently and stably catalyze the conversion of inexpensive raw biomass materials, such as lignocellulose, to produce saccharides and polysaccharides, and related compounds.

At present, there are a limited number of techniques for utilizing recombinant organisms that are capable of producing a fuel. The various techniques often have problems that can lead to low fuel yield, high cost, and undesirable by-products. For example, some known techniques utilize corn grain and other cereals as feedstocks. However, competing feed and food demands on grain supplies and prices may eventually limit the expansion of producing ethanol from corn and other cereals. Other feedstock sources include lignocellulose from which ethanol can be produced via saccharification and fermentation (Lynd, L. R., Cushman, J. H., Nichols, R. J. & Wyman, C. E. Fuel ethanol from cellulosic biomass," Science 251, 1318-1323 (1991)). Because lignocellulose is the primary component of biomass and the most abundant biological material on earth, fuels derived from lignocellulosic biomass are thus renewable energy alternatives that have the potential to sustain the economy, energy, and the environment worldwide. However, conventional lignocellulosic ethanol production requires an expensive and complex multistep process including the production of and pretreatment of lignocellulosic material with exogenous saccharolytic enzymes, hydrolysis of polysaccharides present in pretreated biomass, and separate fermentation of hexose and pentose sugars.

In one embodiment, methods and compositions of the invention comprise genetically modifying or engineering a microorganism to enhance enzyme activity of one or more enzymes, including but not limited to cellulase(s). Examples of such modifications include modifying endogenous nucleic acid regulatory elements to increase expression of one or more enzymes (e.g., operably linking a gene encoding a target enzyme to a strong promoter), introducing into a microorganism additional copies of nucleic acid molecules to provide enhanced activity of an enzyme, operably linking genes encoding one or more enzymes to an inducible promoter or a combination thereof.

Various microorganisms of the invention can be modified to enhance activity of one or more cellulases, or enzymes associated with cellulose processing. The classification of cellulases is usually based on grouping enzymes together that form a family with similar or identical activity, but not necessary the same substrate specificity. One of these classifications is the CAZY system (CAZY stands for Carbohydrate-Active enzymes), for example, where there are 115 different Glycoside Hydrolases (GH) listed, named GH1 to GH155. Each of the different protein families usually has a corresponding enzyme activity. This database includes both cellulose and hemicellulase active enzymes. Furthermore, the entire annotated genome of *Clostridium phytofermentans* is available on the World Wide Web at www.ncbi.nlm.nih.gov/sites/entrez.

Some embodiments described herein simplify the conventional multistep process of lignocellulosic ethanol production by providing methods and compositions where lignocellulosic biomass can be fermented to ethanol in a single step. This is known as consolidated bioprocessing (CBP). Because CBP streamlines the entire conversion process, and reduces costs and energy waste, it is foreseen as the only economically and environmentally sustainable cellulosic ethanol bioprocess.

In some embodiments, polynucleotides and expression cassettes for an efficient fuel-producing system are provided. The polynucleotides and expression cassettes can be used to prepare expression vectors for transforming microorganisms to confer upon the transformed microorganisms the capability of efficiently producing products, such as fuel, in useful quantities.

In some embodiments, the metabolism of a microorganism can be modified by introducing and expressing various genes. In accordance with some embodiments of the present invention, the recombinant microorganisms can use genes from *Clostridium phytofermentans* (ISDgT, American Type Culture Collection 700394T) as a biocatalyst for the enhanced conversion of, for example, cellulose, to a fuel, such as ethanol and hydrogen.

In some embodiments, *C. phytofermentans* (American Type Culture Collection $700394^T$) can be defined based on the phenotypic and genotypic characteristics of a cultured strain, $ISDg^T$ (Warnick et al., International Journal of Systematic and Evolutionary Microbiology, 52:1155-60, 2002). The entire annotated genome of *Clostridium* phytofermentans is available on the World Wide Web at www.ncbi.nlm.nih.gov/sites/entrez. Various embodiments generally relate to systems, and methods and compositions for producing fuels and/or other useful organic products involving strain $ISDg^T$ and/or any other strain of the species *C. phytofermentans*, which may be derived from strain $ISDg^T$ or separately isolated. The species can be defined using standard taxonomic considerations (Stackebrandt and Goebel, International Journal of Systematic Bacteriology, 44:846-9, 1994): Strains with 16S rRNA sequence homology values of 97% and higher as compared to the type strain ($ISDg^T$) are considered strains of *C. phytofermentans*, unless they are shown to have DNA re-association values of less than 70%. Considerable evidence exists to indicate that microbes which have 70% or greater DNA re-association values also have at least 96% DNA sequence identity and share phenotypic traits defining a species. Analyses of the genome sequence of *C. phytofermentans* strain $ISDg^T$ indicate the presence of large numbers of genes and genetic loci that are likely to be involved in mechanisms and pathways for plant polysaccharide fermentation, giving rise to the unusual fermentation properties of this microbe. Based on the above-mentioned taxonomic considerations, all strains of the species *C. phytofermentans* would also possess all, or nearly all, of these fermentation properties. *C. phytofermentans* strains can be natural isolates, or genetically modified strains.

Various expression vectors can be introduced into a host microorganism so that the transformed microorganism can produce large quantities of fuel in various fermentation conditions. The recombinant microorganisms can be modified so that a fuel is stably produced with high yield when grown on a medium comprising, for example, cellulose.

*C. phytofermentans*, alone or in combination with one or more other microbes, can ferment on a large scale a cellulosic biomass material into a combustible biofuel, such as, ethanol, propanol, and/or hydrogen (see, e.g., U.S. Patent Application No. 2007/0178569; Warnick et. al., *Int J Syst Evol Microbiol* (2002), 52 1155-1160, each of which is herein incorporated by reference in its entirety).

The polynucleotides, expression cassettes, and expression vectors disclosed herein can be used with many different host microorganisms for the production of fuel such as ethanol and hydrogen. For example, in addition to *Clostridium phytofermentans*, cellulolytic microorganisms such as *Clostridium cellulovorans*, *Clostridium cellulolyticum*, *Clostridium thermocellum*, *Clostridium josui*, *Clostridium papyrosolvens*, *Clostridium cellobioparum*, *Clostridium hungatei*, *Clostridium cellulosi*, *Clostridium stercorarium*, *Clostridium termitidis*, *Clostridium thermocopriae*, *Clostridium thermocellum*, *Clostridium celerecrescens*, *Clostridium polysaccharolyticum*, *Clostridium populeti*, *Clostridium lentocellum*, *Clostridium chartatabidum*, *Clostridium aldrichii*,

*Clostridium herbivorans, Acetivibrio cellulolyticus, Bacteroides cellulosolvens, Caldicellulosiruptor saccharolyticum, Ruminococcus albus, Ruminococcus flavefaciens, Fibrobacter succinogenes, Eubacterium cellulosolvens, Butyrivibrio fibrisolvens, Anaerocellum thermophilum*, and *Halocella cellulolytica* are particularly attractive hosts, because they are capable of hydrolyzing cellulose. Other microorganisms that can be used include, for example, saccharolytic microbes such as *Thermoanaerobacterium thermosaccharolyticum* and *Thermoanaerobacterium saccharolyticum*. Additional potential hosts include other bacteria, yeasts, algae, fungi, and eukaryotic cells.

In various embodiments, the polynucleotides, expression cassettes, and expression vectors disclosed herein can be used with *C. phytofermentans* or other Clostridia species to increase the production of fuel such as ethanol and hydrogen.

As will be appreciated by one of skill in the art, the ability to produce recombinant organisms that can produce fuels can have great benefit, especially for efficient, cost-effective and environmentally friendly fuel production.

Exemplary Embodiments

The following description and examples illustrate some embodiments of the present invention in detail. Those of skill in the art will recognize that there are numerous variations and modifications that are encompassed by its scope. Accordingly, the description of a preferred embodiment should not be deemed to limit the scope of the present invention.

Various embodiments of the invention offer benefits relating to the production of fuels using recombinant microorganisms. Polynucleotides, expression cassettes, expression vectors and recombinant microorganisms for the optimization of fuel production are disclosed in accordance with some embodiments of the present invention.

Hydrolases

Some embodiments described herein relate to polynucleotides, polynucleotide cassettes, expression cassettes, expression vectors, and microorganisms comprising nucleic acids identified in *C. phytofermentans* as encoding hydrolases. Some embodiments relate to methods for producing fuel utilizing the polynucleotides, polynucleotide cassettes, expression cassettes, expression vectors, and microorganisms comprising nucleic acids identified in *C. phytofermentans* as encoding hydrolases. Advantages to utilizing nucleic acids that encode hydrolases include improving the capabilities and performance of microorganisms to hydrolyze polymers, for example, polysaccharides and polypeptides.

Hydrolases can include enzymes that degrade polymers such as disaccharides, trisaccharides and polysaccharides, polypeptides, and proteins. Polymers can also include, for example, celluloses, hemicelluloses, pectins, lignins, and proteoglycans. Examples of enzymes and enzyme activities that degrade polysaccharides can include, but are not limited to, glycoside hydrolases (GH), glycosyl transferases (GT), polysaccharide lyases (PL), carbohydrate esterases (CE), and proteins containing carbohydrate-binding modules (CBM) (available on the World Wide Web at "cazy.org"; Coutinho, P. M. & Henrissat, B. (1999) Carbohydrate-active enzymes: an integrated database approach. In "Recent Advances in Carbohydrate Bioengineering," H. J. Gilbert, G. Davies, B. Henrissat and B. Svensson eds., The Royal Society of Chemistry, Cambridge, pp. 3-12).

In some embodiments, GH, GT, PL, CE, and CMB can be individual enzymes with distinct activities. In other embodiments, GH, GT, PL, CE, and CMB can be enzyme domains with a particular catalytic activity. For example, an enzyme with multiple activities can have multiple enzyme domains, including for example GH, GT, PL, CE, and/or CBM catalytic domains.

O-glycosyl hydrolases are a widespread group of enzymes that hydrolyse the glycosidic bond between two or more carbohydrates, or between a carbohydrate and a non-carbohydrate moiety. A classification system for glycosyl hydrolases, based on sequence similarity, has led to the definition of 85 different families PUBMED:7624375, PUBMED: 8535779, PUBMED. This classification is available on the CAZy (CArbohydrate-Active EnZymes) web site PUBMED. Because the fold of proteins is better conserved than their sequences, some of the families can be grouped in "clans".

Glycoside hydrolase family 9 comprises enzymes with several known activities, such as endoglucanase and cellobiohydrolase. In *C. phytofermentans*, an exemplary GH9 cellulase is ABX43720.

Any hydrolytic enzyme can be selected from the annotated genome of *C. phytofermentans* for utilization in products and process of invention. Examples include enzymes such as one or more endoglucanase, chitinase, cellobiohydrolase or endoprocessive cellulases (either on reducing or non-reducing end).

Furthermore, a microorganism, such as *C. phytofermentans* can be modified to enhance production of one or more cellulase or hydrolase enzymes or one or more such enzymes can be heterologously expressed in a different host (e.g., other bacteria or yeast). For heterologous expression, bacteria or yeast can be modified through recombinant technology (e.g., Brat et al. Appl. Env. Microbiol. 29; 75:2304-2311, disclosing expression of xylose isomerase in *Saccharomyces cerevisiae*).

Other modifications can be made to enhance end-product (e.g., ethanol) production in a recombinant microorganism of the invention. For example, the host can further comprise an additional heterologous DNA segment, the expression product of which is a protein involved in the transport of mono- and/or oligosaccharides into the recombinant host. Likewise, additional genes from the glycolytic pathway can be incorporated into the host. In such ways, an enhanced rate of ethanol production can be achieved.

One of the most striking and unexpected features of the *C. phytofermentans* genome is the number and diversity of genes encoding carbohydrate-active enzymes. This diversity is unparalleled in organisms related to *C. phytofermentans*. Table 1 illustrates the diversity of carbohydrate genes in relation to other organisms.

TABLE 1

Number and diversity of carbohydrate-active genes

| Organism | Number of glycoside hydrolase genes | Glycoside hydrolase families |
| --- | --- | --- |
| C. phytofermentans | 109 | 39 |
| C. beijerinckii | 75 | 25 |
| C. botulinum | 23 | 10 |
| C. perfringens | 38 | 21 |
| C. thermocellum | 70 | 23 |
| Caldicellulosiruptor saccharolyticus | 61 | 31 |
| Thermoanaerobacter ethanolicus | 15 | 26 |

The *C. phytofermentans* genome includes a diverse range of GH, PL, CE, and CBM genes with a wide range of putative functions predicted using the methods described herein and methods well known in the art. Tables 2 to 5 show examples of some of the known activities of some of the GH, PL, CE, and CBM family members predicted to be present in *C. phytofermentans*, respectively. Known activities are listed by activity and corresponding EC number as determined by the International Union of Biochemistry and Molecular Biology.

TABLE 2

Known activities of glycoside hydrolase family members

| Glycoside Hydrolase Family | Known activities | Number of domains predicted in *C. phytofermentans* |
|---|---|---|
| 1 | beta-glucosidase (EC 3.2.1.21); beta-galactosidase (EC 3.2.1.23); beta-mannosidase (EC 3.2.1.25); beta-glucuronidase (EC 3.2.1.31); beta-D-fucosidase (EC 3.2.1.38); phlorizin hydrolase (EC 3.2.1.62); 6-phospho--galactosidase (EC 3.2.1.85); 6-phospho-beta-glucosidase (EC 3.2.1.86); strictosidinebeta-glucosidase (EC 3.2.1.105); lactase (EC 3.2.1.108); amygdalinbeta-glucosidase (EC 3.2.1.117); prunasin beta-glucosidase (EC 3.2.1.118); raucaffricine beta-glucosidase (EC 3.2.1.125); thioglucosidase (EC 3.2.1.147); beta-primeverosidase (EC 3.2.1.149); isoflavonoid 7-O-beta-apiosyl--glucosidase (EC 3.2.1.161); hydroxyisourate hydrolase (EC 3.—.—.—); beta-glycosidase (EC 3.2.1.—) | 1 |
| 2 | beta-galactosidase (EC 3.2.1.23); beta-mannosidase (EC 3.2.1.25); beta-glucuronidase (EC 3.2.1.31); mannosylglycoprotein endo-beta-mannosidase (EC 3.2.1.152); exo-beta-glucosaminidase (EC 3.2.1.—) | 5 |
| 3 | beta-glucosidase (EC 3.2.1.21); xylan 1,4-beta-xylosidase (EC 3.2.1.37); beta-N-acetylhexosaminidase (EC 3.2.1.52); glucan 1,3-beta-glucosidase (EC 3.2.1.58); glucan 1,4-beta-glucosidase (EC 3.2.1.74); exo-1,3-1,4-glucanase (EC 3.2.1.—); alpha-L-arabinofuranosidase (EC 3.2.1.55). | 8 |
| 4 | maltose-6-phosphate glucosidase (EC 3.2.1.122); alpha-glucosidase (EC 3.2.1.20); alpha-galactosidase (EC 3.2.1.22); 6-phospho-beta-glucosidase (EC 3.2.1.86); alpha-glucuronidase (EC 3.2.1.139). | 3 |
| 5 | chitosanase (EC 3.2.1.132); beta-mannosidase (EC 3.2.1.25); Cellulase (EC 3.2.1.4); glucan 1,3-beta-glucosidase (EC 3.2.1.58); licheninase (EC 3.2.1.73); glucan endo-1,6-beta-glucosidase (EC 3.2.1.75); mannan endo-1,4-beta-mannosidase (EC 3.2.1.78); Endo-1,4-beta-xylanase (EC 3.2.1.8); cellulose 1,4-beta-cellobiosidase (EC 3.2.1.91); endo-1,6-beta-galactanase (EC 3.2.1.—); beta-1,3-mannanase (EC 3.2.1.—); xyloglucan-specific endo-beta-1,4-glucanase (EC 3.2.1.151) | 3 |
| 8 | chitosanase (EC 3.2.1.132); cellulase (EC 3.2.1.4); licheninase (EC 3.2.1.73); endo-1,4-beta-xylanase (EC 3.2.1.8); reducing-end-xylose releasing exo-oligoxylanase (EC 3.2.1.156) | 1 |
| 9 | endoglucanase (EC 3.2.1.4); cellobiohydrolase (EC 3.2.1.91); beta-glucosidase (EC 3.2.1.21) | 1 |
| 10 | xylanase (EC 3.2.1.8); endo-1,3-beta-xylanase (EC 3.2.1.32) | 6 |
| 11 | xylanase (EC 3.2.1.8). | 1 |
| 12 | endoglucanase (EC 3.2.1.4); xyloglucan hydrolase (EC 3.2.1.151); beta-1,3-1,4-glucanase (EC 3.2.1.73); xyloglucan endotransglycosylase (EC 2.4.1.207) | 1 |
| 13 | apha-amylase (EC 3.2.1.1); pullulanase (EC 3.2.1.41); cyclomaltodextrin glucanotransferase (EC 2.4.1.19); cyclomaltodextrinase (EC 3.2.1.54); trehalose-6-phosphate hydrolase (EC 3.2.1.93); oligo-alpha-glucosidase (EC 3.2.1.10); maltogenic amylase (EC 3.2.1.133); neopullulanase (EC 3.2.1.135); alpha-glucosidase (EC 3.2.1.20); maltotetraose-forming alpha-amylase (EC 3.2.1.60); isoamylase (EC 3.2.1.68); glucodextranase (EC 3.2.1.70); maltohexaose-forming alpha-amylase (EC 3.2.1.98); branching enzyme (EC 2.4.1.18); trehalose synthase (EC 5.4.99.16); 4--glucanotransferase (EC 2.4.1.25); maltopentaose-forming-amylase (EC 3.2.1.—); amylosucrase (EC 2.4.1.4); sucrose phosphorylase (EC 2.4.1.7); malto-oligosyltrehalose trehalohydrolase (EC 3.2.1.141); isomaltulose synthase (EC 5.4.99.11). | 7 |
| 16 | xyloglucan:xyloglucosyltransferase (EC 2.4.1.207); keratan-sulfate endo-1,4-beta-galactosidase (EC 3.2.1.103); Glucan endo-1,3-beta-D-glucosidase (EC 3.2.1.39); endo-1,3(4)-beta-glucanase (EC 3.2.1.6); Licheninase (EC 3.2.1.73); agarase (EC 3.2.1.81); beta-carrageenase (EC 3.2.1.83); xyloglucanase (EC 3.2.1.151) | 1 |
| 18 | chitinase (EC 3.2.1.14); endo-beta-N-acetylglucosaminidase (EC 3.2.1.96); non-catalytic proteins: xylanase inhibitors; concanavalin B; narbonin | 6 |
| 19 | chitinase (EC 3.2.1.14). | 2 |
| 20 | beta-hexosaminidase (EC 3.2.1.52); lacto-N-biosidase (EC 3.2.1.140); -1,6-N-acetylglucosaminidase) (EC 3.2.1.—) | 3 |
| 25 | lysozyme (EC 3.2.1.17) | 1 |
| 26 | beta-mannanase (EC 3.2.1.78); beta-1,3-xylanase (EC 3.2.1.32) | 3 |

TABLE 2-continued

Known activities of glycoside hydrolase family members

| Glycoside Hydrolase Family | Known activities | Number of domains predicted in *C. phytofermentans* |
|---|---|---|
| 28 | polygalacturonase (EC 3.2.1.15); exo-polygalacturonase (EC 3.2.1.67); exo-polygalacturonosidase (EC 3.2.1.82); rhamnogalacturonase (EC 3.2.1.—); endo-xylogalacturonan hydrolase (EC 3.2.1.—); rhamnogalacturonan alpha-L-rhamnopyranohydrolase (EC 3.2.1.40) | 5 |
| 29 | alpha-L-fucosidase (EC 3.2.1.51) | 3 |
| 30 | glucosylceramidase (EC 3.2.1.45); beta-1,6-glucanase (EC 3.2.1.75); beta-xylosidase (EC 3.2.1.37) | 2 |
| 31 | alpha-glucosidase (EC 3.2.1.20); alpha-1,3-glucosidase (EC 3.2.1.84); sucrase-isomaltase (EC 3.2.1.48) (EC 3.2.1.10); alpha-xylosidase (EC 3.2.1.—); alpha-glucan lyase (EC 4.2.2.13); isomaltosyltransferase (EC 2.4.1.—). | 3 |
| 36 | alpha-galactosidase (EC 3.2.1.22); alpha-N-acetylgalactosaminidase (EC 3.2.1.49); stachyose synthase (EC 2.4.1.67); raffinose synthase (EC 2.4.1.82) | 2 |
| 38 | alpha-mannosidase (EC 3.2.1.24); alpha-mannosidase (EC 3.2.1.114) | 1 |
| 43 | beta-xylosidase (EC 3.2.1.37); beta-1,3-xylosidase (EC 3.2.1.—); alpha-L-arabinofuranosidase (EC 3.2.1.55); arabinanase (EC 3.2.1.99); xylanase (EC 3.2.1.8); galactan 1,3-beta-galactosidase (EC 3.2.1.145) | 8 |
| 48 | endoglucanase (EC 3.2.1.4); chitinase (EC 3.2.1.14); cellobiohydrolases: some cellobiohydrolases of this family have been reported to act from the reducing ends of cellulose (EC 3.2.1.—), while others have been reported to operate from the non-reducing ends to liberate cellobiose or cellotriose or cellotetraose (EC 3.2.1.—). This family also contains endo-processive cellulases (EC 3.2.1.—), whose activity is hard to distinguish from that of cellobiohydrolases. | 1 |
| 51 | alpha-L-arabinofuranosidase (EC 3.2.1.55); endoglucanase (EC 3.2.1.4) | 1 |
| 65 | trehalase (EC 3.2.1.28); maltose phosphorylase (EC 2.4.1.8); trehalose phosphorylase (EC 2.4.1.64); kojibiose phosphorylase (EC 2.4.1.230) | 4 |
| 67 | alpha-glucuronidase (EC 3.2.1.139); xylan alpha-1,2-glucuronosidase (EC 3.2.1.131) | 1 |
| 73 | peptidoglycan hydrolases with endo-beta-N-acetylglucosaminidase (EC 3.2.1.—) specificity; there is only one, unconfirmed, report of beta-1,4-N-acetylmuramoylhydrolase (EC 3.2.1.17) activity | 1 |
| 77 | amylomaltase or 4-alpha-glucanotransferase (EC 2.4.1.25) | 1 |
| 85 | endo-beta-N-acetylglucosaminidase (EC 3.2.1.96) | 1 |
| 87 | mycodextranase (EC 3.2.1.61); alpha-1,3-glucanase (EC 3.2.1.59) | 3 |
| 88 | d-4,5 unsaturated beta-glucuronyl hydrolase (EC 3.2.1.—) | 4 |
| 94 | cellobiose phosphorylase (EC 2.4.1.20); cellodextrin phosphorylase (EC 2.4.1.49); chitobiose phosphorylase (EC 2.4.1.—); cyclic beta-1,2-glucan synthase (EC 2.4.1.—) | 5 |
| 95 | alpha-1,2-L-fucosidase (EC 3.2.1.63); alpha-L-fucosidase (EC 3.2.1.51) | 2 |
| 105 | unsaturated rhamnogalacturonyl hydrolase (EC 3.2.1.—) | 3 |
| 106 | alpha-L-rhamnosidase (EC 3.2.1.40) | 1 |
| 112 | lacto-N-biose phosphorylase or galacto-N-biose phosphorylase (EC 2.4.1.211) | 3 |

TABLE 3

Known activities of polysaccharide lyase family members

| Polysaccharide lyase family | Known activities | Number of domains predicted in *C. phytofermentans* |
|---|---|---|
| 1 | pectate lyase (EC 4.2.2.2); exo-pectate lyase (EC 4.2.2.9); pectin lyase (EC 4.2.2.10). | 1 |
| 7 | alginate lyase (EC 4.2.2.3); -L-guluronate lyase (EC 4.2.2.11) | 1 |
| 9 | pectate lyase (EC 4.2.2.2); exopolygalacturonate lyase (EC 4.2.2.9). | 4 |
| 11 | pectate lyase (EC 4.2.2.2); exopolygalacturonate lyase (EC 4.2.2.9). | 1 |
| 12 | Heparin-sulfate lyase (EC 4.2.2.8) | 1 |
| 15 | oligo-alginate lyase (EC 4.2.2.—) | 1 |
| 17 | alginate lyase (EC 4.2.2.3). | 1 |

TABLE 4

Known activities of carbohydrate esterase family members

| Carbohydrate esterase family | Known activities | Number of domains predicted in C. phytofermentans |
|---|---|---|
| 2 | acetyl xylan esterase (EC 3.1.1.72). | 2 |
| 4 | acetyl xylan esterase (EC 3.1.1.72); chitin deacetylase (EC 3.5.1.41); chitooligosaccharide deacetylase (EC 3.5.1.—); peptidoglycan GlcNAc deacetylase (EC 3.5.1.—); peptidoglycan N-acetylmuramic acid deacetylase (EC 3.5.1.—). | 8 |
| 8 | pectin methylesterase (EC 3.1.1.11). | 1 |
| 9 | N-acetylglucosamine 6-phosphate deacetylase (EC 3.5.1.25); N-acetylgalactosamine-6-phosphate deacetylase (EC 3.5.1.80). | 2 |
| 12 | pectin acetylesterase (EC 3.1.1.—); rhamnogalacturonan acetylesterase (EC 3.1.1.—); acetyl xylan esterase (EC 3.1.1.72) | 1 |
| 15 | 4-O-methyl-glucuronyl esterase (3.1.1.—) | 1 |

TABLE 5

Known activities of carbohydrate-binding module family members

| CBM family | Known activities | Number of domains predicted in C. phytofermentans |
|---|---|---|
| 2 | Modules of approx. 100 residues found in many bacterial enzymes with putative cellulose, chitin and/or xylan binding activities. | 1 |
| 3 | Modules of approx. 150 residues found in bacterial enzymes. The cellulose-binding function has been demonstrated in many cases. In one instance binding to chitin has been reported. | 5 |
| 4 | Modules of approx. 150 residues found in bacterial enzymes. Binding of these modules has been demonstrated with xylan, -1,3-glucan, -1,3-1,4-glucan, -1,6-glucan and amorphous cellulose but not with crystalline cellulose. | 4 |
| 5 | Modules of approx. 60 residues found in bacterial enzymes. Distantly related to the CBM12 family. | 1 |
| 6 | Modules of approx. 120 residues. The cellulose-binding function has been demonstrated in one case on amorphous cellulose and xylan. Some of these modules also bind-1,3-glucan. | 1 |
| 12 | Modules of approx. 40-60 residues. The majority of these modules is found among chitinases where the function is chitin-binding. Distantly related to the CBM5 family. | 2 |
| 13 | Modules of approx. 150 residues which often appear as a threefold internal repeat, an exception includes, xylanase II of Actinomadura sp. FC7 (GenBank U08894). These modules were first identified in several plant lectins such as ricin or agglutinin of Ricinus communis which bind galactose residues. The three-dimensional structure of a plant lectin has been determined and displays a pseudo-threefold symmetry in accord with the observed sequence threefold repeat. These modules have since been found in a number of other proteins of various functions including glycoside hydrolases and glycosyltransferases. While in the plant lectins this module binds mannose, binding to xylan has been demonstrated in the Streptomyces lividans xylanase A and arabinofuranosidase B. Binding to GalNAc has been shown for the corresponding module of GalNAc transferase 4. For the other proteins, the binding specificity of these modules has not been established. The pseudo three-fold symmetry of the CBM13 module has now been confirmed in the 3-D structure of the intact, two-domain, xylanase of Streptomyces olivaceoviridis. | 1 |
| 22 | A xylan binding function has been demonstrated in several cases and affinity with mixed -1,3/-1,4-glucans in one. In several cases a thermostabilizing effect has also been seen. | 1 |
| 32 | Binding to galactose and lactose has been demonstrated for the module of Micromonospora viridifaciens sialidase (PMID: 16239725); binding to polygalacturonic acid has been shown for a Yersinia member (PMID: 17292916); binding to LacNAc (-D-galactosyl-1,4--D-N-acetylglucosamine) has been shown for an N-acetylglucosaminidase from Clostridium perfingens (PMID: 16990278). | 5 |

TABLE 5-continued

Known activities of carbohydrate-binding module family members

| CBM family | Known activities | Number of domains predicted in *C. phytofermentans* |
|---|---|---|
| 35 | Modules of approx. 130 residues. A module that is conserved in three *Cellvibrio* xylan-degrading enzymes binds to xylan and the interaction is calcium dependent, while a module from a *Cellvibrio mannanase* binds to decorated soluble mannans and mannooligosaccharides. A module in a *Phanerochaete chrysosporium* galactan 1,3--galactosidase binds to -galactan. | 4 |
| 36 | Modules of approx. 130 residues. A module that is conserved in three Cellvibrio xylan-degrading enzymes binds to xylan and the interaction is calcium dependent, while a module from a *Cellvibrio mannanase* binds to decorated soluble mannans and mannooligosaccharides. A module in a *Phanerochaete chrysosporium* galactan 1,3--galactosidase binds to -galactan. | 1 |
| 41 | Modules of approx. 100 residues found in primarily in bacterial pullulanases. The N-terminal module from *Thermotoga maritima* Pul13 has been shown to bind to the -glucans amylose, amylopectin, pullulan, and oligosaccharide fragments derived from these polysaccharides. | 1 |
| 46 | Modules of approx. 100 residues, found at the C-terminus of several GH5 cellulases. Cellulose-binding function demonstrated in one case. | 1 |
| 48 | Modules of approx. 100 residues with glycogen-binding function, appended to GH13 modules. Also found in the beta subunit (glycogen-binding) of AMP-activated protein kinases (AMPK) | 2 |
| 50 | Modules of approx. 50 residues found attached to various enzymes from families GH18, GH19, GH23, GH24, GH25 and GH73, i.e. enzymes cleaving either chitin or peptidoglycan. Binding to chitopentaose demonstrated in the case of Pteris ryukyuensis chitinase A [Ohnuma T et al.; PMID: 18083709]. CBM50 modules are also found in a multitude of other enzymes targeting the petidoglycan such as peptidases and amidases. | 4 |

Some embodiments include genes encoding hydrolases shown in Table 6. The JGI number refers to the NCBI locus tag on the GenBank record.

TABLE 6

Predicted hydrolases in *C. phytofermentans*

| JGI No. | GH | GH Module Architecture |
|---|---|---|
| Cphy0191 | GH43 | |
| Cphy0203 | GH105 | |
| Cphy0218 | GH31 | |
| Cphy0220 | GH3 | |
| Cphy0288 | GH88 | |
| Cphy0430 | GH94 | |
| Cphy0530 | GH2 | |
| Cphy0531 | GH43 | |
| Cphy0607 | GH20 | |
| Cphy0662 | GH3 | |
| Cphy0666 | GH106 | |
| Cphy0694 | GH94 | |
| Cphy0699 | GH3 | |
| Cphy0711 | GH2 | |
| Cphy0769 | GH4 | |
| Cphy0776 | GH88 | |
| Cphy0857 | GH94 | |
| Cphy0858 | GH30 | |
| Cphy0874 | GH95 | |
| Cphy0875 | GH43 | |
| Cphy0934 | GH88 | |
| Cphy1019 | GH65 | |
| Cphy1071 | GH26 | CBM35-GH26-CBM3 |
| Cphy1125 | GH3 | |
| Cphy1163 | GH5 | |
| Cphy1169 | GH51 | |
| Cphy1308 | GH87 | |
| Cphy1395 | GH95 | |
| Cphy1435 | GH19 | |
| Cphy1510 | GH10 | |
| Cphy1596 | GH3 | |
| Cphy1612 | | |
| Cphy1640 | GH12 | |
| Cphy1652 | GH18 | |
| Cphy1688 | GH* | |
| Cphy1711 | GH28 | |
| Cphy1714 | GH85 | GH85-CBM32 |
| Cphy1720 | GH38 | |
| Cphy1750 | GH105 | |
| Cphy1775 | GH* | SLH-GH*-CBM32-CBM32 |
| Cphy1799 | GH18 | CBM12-GH18 |
| Cphy1800 | GH18 | GH18-CBM12 |
| Cphy1815 | GH18 | GH18-LRR |
| Cphy1873 | GH87 | CBM35-CBM6-GH87 |
| Cphy1874 | GH65 | |
| Cphy1877 | GH31 | |
| Cphy1882 | GH87 | GH87-SORT |
| Cphy1888 | | |
| Cphy1919 | GH105 | |
| Cphy1929 | GH94 | |
| Cphy1934 | GH13 | |
| Cphy1936 | GH36 | |
| Cphy1937 | GH1 | |
| Cphy1943 | GH19 | CBM5-GH19 |
| Cphy2025 | GH2 | |
| Cphy2028 | GH43 | |
| Cphy2058 | GH5 | |
| Cphy2105 | GH11 | |
| Cphy2108 | GH10 | CBM22-GH10-SORT |
| Cphy2128 | GH26 | CBM35-GH26-X2-X2-CBM3 |
| Cphy2190 | GH29 | |
| Cphy2276 | GH26 | CBM35-GH26 |

TABLE 6-continued

Predicted hydrolases in *C. phytofermentans*

| JGI No. | GH | GH Module Architecture |
|---|---|---|
| Cphy2304 | GH13 | CBM41-CBM48-GH13-SORT |
| Cphy2331 | GH13 | CBM48-GH13 |
| Cphy2332 | GH3 | |
| Cphy2341 | GH13 | |
| Cphy2342 | GH13 | |
| Cphy2344 | GH13 | |
| Cphy2349 | GH77 | |
| Cphy2350 | GH13 | |
| Cphy2567 | GH28 | |
| Cphy2572 | GH18 | |
| Cphy2632 | GH43 | |
| Cphy2736 | GH28 | |
| Cphy2848 | GH4 | |
| Cphy2919 | | |
| Cphy3009 | GH3 | |
| Cphy3010 | GH10 | |
| Cphy3011 | GH43 | |
| Cphy3023 | GH29 | |
| Cphy3028 | GH29 | |
| Cphy3029 | GH88 | |
| Cphy3056 | GH36 | |
| Cphy3081 | GH2 | |
| Cphy3109 | GH25 | |
| Cphy3158 | GH67 | |
| Cphy3160 | GH2 | |
| Cphy3202 | GH5 | GH5-X2-CBM46-CBM2 |
| Cphy3207 | GH8 | |
| Cphy3217 | GH28 | |
| Cphy3239 | GH20 | |
| Cphy3310 | GH28 | |
| Cphy3313 | GH65 | |
| Cphy3314 | GH65 | |
| Cphy3329 | GH3 | |
| Cphy3367 | GH9 | GH9-CBM3-X2-X2-CBM3 |
| Cphy3368 | GH48 | GH48-X2-CBM3 |
| Cphy3388 | GH16 | GH16-CBM4-CBM4-CBM4-CBM4 |
| Cphy3396 | GH4 | |
| Cphy3398 | GH43 | |
| Cphy3404 | GH30 | |
| Cphy3466 | GH73 | |
| Cphy3571 | GH20 | |
| Cphy3586 | GH53 | GH53-CBM13 |
| Cphy3618 | GH43 | |
| Cphy3749 | GH18 | |
| Cphy3785 | GH31 | |
| Cphy3854 | GH94 | |
| Cphy3862 | GH10 | GH10-GH10-CE15 |

In some embodiments, enzymes that degrade polysaccharides can include enzymes that degrade cellulose, namely, cellulases. Some cellulases, including endocellulases (EC 3.2.1.4) and exo-cellulases (EC 3.2.1.91), hydrolyze beta-1,4-glucosidic bonds.

Examples of predicted endo-cellulases in *C. phytofermentans* can include genes within the GH5 family, such as, Cphy3368; Cphy1163, and Cphy2058; the GH8 family, such as Cphy3207; and the GH9 family, such as Cphy3367. Examples of exo-cellulases in *C. phytofermentans* can include genes within the GH48 family, such as Cphy3368. Some exo-cellulases hydrolyze polysaccharides to produce 2 to 4 unit oligosaccharides of glucose, resulting in cellodextrins disaccharides (cellobiose), trisaccharides (cellotriose), or tetrasaccharides (cellotetraose). Members of the GH5, GH9 and GH48 families can have both exo- and endo-cellulase activity.

In some embodiments, enzymes that degrade polysaccharides can include enzymes that have the ability to degrade hemicellulose, namely, hemicellulases (Leschine, S. B. in Handbook on Clostridia (ed. Dürre, P.) (CRC Press, Boca Raton, 2005)). Hemicellulose can be a major component of plant biomass and can contain a mixture of pentoses and hexoses, for example, D-xylopyranose, L-arabinofuranose, D-mannopyranose, D-glucopyranose, D-galactopyranose, D-glucopyranosyluronic acid and other sugars (Aspinall, G. O. The Biochemistry of Plants 473, 1980; Han, J. S. & Rowell, J. S. in *Paper and composites from agro-based resources* 83, 1997). In certain embodiments, predicted hemicellulases identified in *C. phytofermentans* can include enzymes active on the linear backbone of hemicellulose, for example, endo-beta-1,4-D-xylanase (EC 3.2.1.8), such as GH5, GH10, GH11, and GH43 family members; 1,4-beta-D-xyloside xylohydrolase (EC 3.2.1.37), such as GH30, GH43, and GH3 family members; and beta-mannanase (EC 3.2.1.78), such as GH26 family members. (See Table 6).

In some embodiments, predicted hemicellulases identified in *C. phytofermentans* can include enzymes active on the side groups and substituents of hemicellulose, for example, alpha-L-arabinofuranosidase (EC 3.2.1.55), such as GH3, GH43, and GH51 family members; alpha-xylosidase, such as GH31 family members; alpha-fucosidase (EC 3.2.1.51), such as GH95 and GH29 family members; galactosidase, such as GH1, GH2, GH4, GH36, GH43 family members; and acetyl-xylan esterase (EC 3.1.1.72), such as CE2 and CE4. (See Table 6).

In some embodiments, enzymes that degrade polysaccharides can include enzymes that have the ability to degrade pectin, namely, pectinases. In plant cell walls, the cross-linked cellulose network can be embedded in a matrix of pectins that may be covalently cross-linked to xyloglucans and certain structural proteins. Pectin can comprise homogalacturonan (HG) or rhamnogalacturonan (RH).

In other embodiments, pectinases identified in *C. phytofermentans* can hydrolyze HG. HG can be composed of D-galacturonic acid (D-galA) units, which may be acetylated and methylated. Enzymes that hydrolyze HG can include, for example, 1,4-alpha-D galacturonan lyase (EC 4.2.2.2), such as PL1, PL9, and PL11 family members; glucuronyl hydrolase, such as GH88 and GH105 family members; pectin acetylesterase such as CE12 family members; and pectin methylesterase, such as CE8 family members. (See Table 6).

In even some embodiments, pectinases identified in *C. phytofermentans* can hydrolyze RH. RH can be a backbone composed of alternating 1,2-alpha-L-rhamnose (L-Rha) and 1,4-alpha-D-galacturonic residues (Lau, J. M., McNeil M., Darvill A. G. & Albersheim P. Structure of the backbone of rhamnogalacturonan I, a pectic polysaccharide in the primary cell walls of plants. *Carbohydrate research* 137, 111 (1985)). The rhamnose residues of the backbones can have galactan, arabinan, or arabinogalactan attached to C4 as side chains. Enzymes that hydrolyze HG can include, for example, endo-rhamnogalacturonase, such as GH28 family members; and rhamnogalacturonan lyase, such as PL11 family members. (See Table 6).

Some embodiments include enzymes that can hydrolyze starch. *C. phytofermentans* can degrade starch and chitin (Warnick, T. A., Methe, B. A. & Leschine, S. B. *Clostridium phytofermentans* sp. nov., a cellulolytic mesophile from forest soil. *Int. J. Syst. Evol. Microbiol.* 52, 1155-1160 (2002); Leschine, S. B. in *Handbook on Clostridia* (ed Dürre, P.) (CRC Press, Boca Raton, 2005); Reguera, G. & Leschine, S. B. Chitin degradation by cellulolytic anaerobes and facultative aerobes from soils and sediments. *FEMS Microbiol. Lett.* 204, 367-374 (2001)). Enzymes that hydrolyze starch include alpha-amylase, glucoamylase, beta-amylase, exo-alpha-1,4-glucanase, and pullulanase. Examples of predicted enzymes identified in *C. phytofermentans* involved in starch hydrolysis include GH13 family members. (See Table 6).

In other embodiments, hydrolases can include enzymes that hydrolyze chitin. Examples of enzymes that may hydrolyze chitin include GH18 and GH19 family members. (See Table 6).

In even some embodiments, hydrolases can include enzymes that hydrolyze lichen, namely, lichenase, for example, GH16 family members, such as Cphy3388.

In some embodiments, hydrolases can include CBM family members. Without wishing to be bound to any one theory, CBM domains may function to localize enzyme complexes to particular substrates. Examples of predicted CBM families identified in *C. phytofermentans* that may bind cellulose include CBM2, CBM3, CBM4, CBM6, and CBM46 family members. Examples of predicted CBM families identified in *C. phytofermentans* that may bind xylan include CBM2, CBM4, CBM6, CBM13, CBM22, CBM35, and CBM36 family members. (See Table 6). In other embodiments, CBM domain family members may function to stabilize an enzyme complex.

Some embodiments include polynucleotides encoding at least one predicted hydrolase identified in *C. phytofermentans*.

ATP-Binding Cassette Transporters

Some embodiments described herein relate to polynucleotides, polynucleotide cassettes, expression cassettes, expression vectors, and microorganisms comprising nucleic acids identified in *C. phytofermentans* that encode ATP-binding cassette-transporters (ABC-transporters). Some embodiments relate to methods for producing fuel utilizing these polynucleotides, polynucleotide cassettes, expression cassettes, expression vectors, and microorganisms comprising nucleic acids identified in *C. phytofermentans* that encode ABC-transporters. Advantages to utilizing nucleic acids encoding ABC-transporters include increasing the capacity of transformed organisms to transport compounds into the organism and utilize such compounds in the biochemical pathways to produce fuel, and thus improve fuel production. Examples of such compounds include the products of polymer hydrolysis.

ABC-transporter proteins utilize ATP hydrolysis to transport a wide variety of substances across the plasma membrane. Such substances can include sugars and amino acids. ABC-transporters can be identified using the methods described herein and methods well known in the art. ABC transporters comprise at least two types of domains, transmembrane domains and nucleotide (e.g., ATP) binding domains. Some ABC transporters also include a solute binding domain that assists in mediation of solute transport. These domains can be present on the same polypeptide chain or multiple polypeptide chains. Some members of the ABC-transporter family comprise the ABC_tran (pfam00005) domain. More members of the ABC-transporter family can comprise 4 domains within two symmetric halves that are linked by a long charged region and a highly hydrophobic segment (Hyde et al., Nature, 346:362-365 (1990); Luciani et al., Genomics, 21: 150-159 (1994)).

In more exemplary embodiments, polynucleotide cassettes, expression cassettes, expression vectors, and organisms comprising ABC-transporters are identified in *C. phytofermentans*. Such gene clusters can be identified using the methods described herein and the methods well known in the art. In some embodiments, genes and gene clusters can be identified by the degree of homology between clusters of orthologous groups of proteins (COG). Such genes and gene clusters can be included on cassettes or expressed together. Examples can include the predicted ABC-transporters and ABC-transporter domains shown in Table 7. Column "No." represents putative clusters. ABC-transporter domains can include signal transduction domains.

TABLE 7

Predicted ABC-transporters and other proteins/domains in *C. phytofermentans*

| No. | JGI No. | Location | COG | COG Description |
|---|---|---|---|---|
| 1 | Cphy0110 | 147354 . . . 148388 | CDA1 | Predicted xylanase/chitin deacetylase |
|   | Cphy0111 | 148828 . . . 149403 | Pth | Peptidyl-tRNA hydrolase |
|   | Cphy0112 | 149444 . . . 152983 | Mfd | Transcription-repair coupling factor (superfamily II helicase) |
|   | Cphy0113 | 153051 . . . 154184 |  | NoCogMatch |
|   | Cphy0114 | 154273 . . . 155049 | CcmA | ABC-type multidrug transport system, ATPase component |
|   | Cphy0115 | 155051 . . . 156268 | NatB | ABC-type Na+ efflux pump, permease component |
|   | Cphy0116 | 156368 . . . 156760 | ArsR | Predicted transcriptional regulators |
|   | Cphy0117 | 156810 . . . 157454 | COG0490 | Putative regulatory, ligand-binding protein related to C-terminal domains of K+ channels |
|   | Cphy0118 | 158002 . . . 159138 | OpuBA | ABC-type proline/glycine betaine transport systems, ATPase components |
|   | Cphy0119 | 159135 . . . 160706 | OpuBC | Periplasmic glycine betaine/choline-binding (lipo)protein of an ABC-type transport system (osmoprotectant binding protein) |
| 2 | Cphy0191 | 236617 . . . 238155 | XynB | Beta-xylosidase |
|   | Cphy0192 | 238298 . . . 240091 | SalX | ABC-type antimicrobial peptide transport system, ATPase component |
|   | Cphy0193 | 240094 . . . 242037 | SalX | ABC-type antimicrobial peptide transport system, ATPase component |
|   | Cphy0194 | 242049 . . . 242735 |  | NoCogMatch |
|   | Cphy0195 | 242919 . . . 244052 | BaeS | Signal transduction histidine kinase |
|   | Cphy0196 | 244049 . . . 244729 | OmpR | Response regulators consisting of a CheY-like receiver domain and a winged-helix DNA-binding domain |
| 3 | Cphy0288 | 358277 . . . 359431 | COG1331 | Highly conserved protein containing a thioredoxin domain |
|   | Cphy0289 | 359443 . . . 360273 | UgpE | ABC-type sugar transport system, permease component |
|   | Cphy0290 | 360288 . . . 361181 | UgpA | ABC-type sugar transport systems, permease components |
|   | Cphy0291 | 361234 . . . 362583 | UgpB | ABC-type sugar transport system, periplasmic component |
|   | Cphy0292 | 362867 . . . 364387 | LytS | Putative regulator of cell autolysis |
|   | Cphy0293 | 364406 . . . 366004 | COG4753 | Response regulator containing CheY-like receiver domain and AraC-type DNA-binding domain |

TABLE 7-continued

Predicted ABC-transporters and other proteins/domains in *C. phytofermentans*

| No. | JGI No. | Location | COG | COG Description |
|---|---|---|---|---|
| 4 | Cphy0337 | 423685 ... 425433 | MdlB | ABC-type multidrug transport system, ATPase and permease components |
|  | Cphy0338 | 425701 ... 427869 | Tex | Transcriptional accessory protein |
|  | Cphy0339 | 428277 ... 429278 | LplB | ABC-type polysaccharide transport system, permease component |
|  | Cphy0340 | 429392 ... 430300 | UgpE | ABC-type sugar transport system, permease component |
|  | Cphy0341 | 430405 ... 432018 | UgpB | ABC-type sugar transport system, periplasmic component |
|  | Cphy0342 | 432371 ... 434707 | AraC | AraC-type DNA-binding domain-containing proteins |
|  | Cphy0343 | 434803 ... 437214 |  | NoCogMatch |
| 5 | Cphy0430 | 547250 ... 549745 | COG3459 | Cellobiose phosphorylase |
|  | Cphy0431 | 550144 ... 551712 | DdpA | ABC-type dipeptide transport system, periplasmic component |
|  | Cphy0432 | 551801 ... 552742 | DppB | ABC-type dipeptide/oligopeptide/nickel transport systems, permease components |
|  | Cphy0433 | 552764 ... 553552 | DppC | ABC-type dipeptide/oligopeptide/nickel transport systems, permease components |
|  | Cphy0434 | 553633 ... 555201 | COG1123 | ATPase components of various ABC-type transport systems, contain duplicated ATPase |
| 6 | Cphy0484 | 612448 ... 613455 | PurR | Transcriptional regulators |
|  | Cphy0485 | 613468 ... 614448 | LplB | ABC-type polysaccharide transport system, permease component |
|  | Cphy0486 | 614460 ... 615353 | UgpE | ABC-type sugar transport system, permease component |
|  | Cphy0487 | 615427 ... 617103 | UgpB | ABC-type sugar transport system, periplasmic component |
|  | Cphy0488 | 617267 ... 619552 |  | NoCogMatch |
|  | Cphy0489 | 619572 ... 621440 |  | NoCogMatch |
|  | Cphy0490 | 621481 ... 622278 | FabG | Dehydrogenases with different specificities (related to short-chain alcohol dehydrogenases) |
|  | Cphy0491 | 622395 ... 623030 | RpiB | Ribose 5-phosphate isomerase RpiB |
|  | Cphy0492 | 623046 ... 627716 | COG3858 | Predicted glycosyl hydrolase |
|  | Cphy0493 | 627945 ... 630125 | Tar | Methyl-accepting chemotaxis protein |
|  | Cphy0494 | 630357 ... 631754 | UgpB | ABC-type sugar transport system, periplasmic component |
|  | Cphy0495 | 631901 ... 633715 | COG2972 | Predicted signal transduction protein with a C-terminal ATPase domain |
|  | Cphy0496 | 633810 ... 635441 | COG4753 | Response regulator containing CheY-like receiver domain and AraC-type DNA-binding domain |
|  | Cphy0497 | 635568 ... 638291 | markorf3686 | Glycosyl transferase, family 51:Penicillin-binding protein, transpeptidase precursor |
|  | Cphy0498 | 638612 ... 641344 | MrcA | Membrane carboxypeptidase/penicillin-binding protein |
| 7 | Cphy0525 | 665552 ... 667120 | COG4753 | Response regulator containing CheY-like receiver domain and AraC-type DNA-binding domain |
|  | Cphy0526 | 667117 ... 668901 | COG2972 | Predicted signal transduction protein with a C-terminal ATPase domain |
|  | Cphy0527 | 669186 ... 670076 | UgpA | ABC-type sugar transport systems, permease components |
|  | Cphy0528 | 670088 ... 670933 | UgpE | ABC-type sugar transport system, permease component |
|  | Cphy0529 | 671066 ... 672460 | UgpB | ABC-type sugar transport system, periplasmic component |
|  | Cphy0530 | 672748 ... 674523 | LacZ | Beta-galactosidase/beta-glucuronidase |
|  | Cphy0531 | 674706 ... 676121 | XynB | Beta-xylosidase |
| 8 | Cphy0615 | 800570 ... 801004 |  | NoCogMatch |
|  | Cphy0616 | 801007 ... 801984 |  | NoCogMatch |
|  | Cphy0617 | 802351 ... 804156 | LytS | Putative regulator of cell autolysis |
|  | Cphy0618 | 804146 ... 804922 | COG4753 | Response regulator containing CheY-like receiver domain and AraC-type DNA-binding domain |
|  | Cphy0619 | 805147 ... 806538 | UgpB | ABC-type sugar transport system, periplasmic component |
|  | Cphy0620 | 806729 ... 807646 | UgpA | ABC-type sugar transport systems, permease components |
|  | Cphy0621 | 807636 ... 808505 | UgpE | ABC-type sugar transport system, permease component |
|  | Cphy0622 | 808851 ... 809189 | MutS | Mismatch repair ATPase (MutS family) |
|  | Cphy0623 | 809475 ... 810185 |  | NoCogMatch |
|  | Cphy0624 | 810523 ... 812793 | XynA | Beta-1,4-xylanase |
|  | Cphy0625 | 813011 ... 813778 | COG0627 | Predicted esterase |
|  | Cphy0626 | 813769 ... 814512 | COG0627 | Predicted esterase |
| 9 | Cphy0662 | 862473 ... 864716 | BglX | Beta-glucosidase-related glycosidases |
|  | Cphy0663 | 864876 ... 866546 | UgpB | ABC-type sugar transport system, periplasmic component |
|  | Cphy0664 | 866795 ... 867769 | LplB | ABC-type polysaccharide transport system, permease component |
|  | Cphy0665 | 867787 ... 868674 | UgpE | ABC-type sugar transport system, permease component |
|  | Cphy0666 | 868759 ... 871452 |  | NoCogMatch |
|  | Cphy0667 | 871581 ... 872183 | AcrR | Transcriptional regulator |
|  | Cphy0668 | 873253 ... 873825 |  | NoCogMatch |
|  | Cphy0669 | 873964 ... 874098 | GalE | UDP-glucose 4-epimerase |
| 10 | Cphy0694 | 896904 ... 900245 | COG3459 | Cellobiose phosphorylase |
|  | Cphy0695 | 900644 ... 901510 | LplB | ABC-type polysaccharide transport system, permease component |
|  | Cphy0696 | 901526 ... 902437 | UgpE | ABC-type sugar transport system, permease component |
|  | Cphy0697 | 902506 ... 904050 | UgpB | ABC-type sugar transport system, periplasmic component |
|  | Cphy0698 | 904124 ... 905161 | PurR | Transcriptional regulators |
|  | Cphy0699 | 905298 ... 907529 | BglX | Beta-glucosidase-related glycosidases |

TABLE 7-continued

Predicted ABC-transporters and other proteins/domains in *C. phytofermentans*

| No. | JGI No. | Location | COG | COG Description |
|---|---|---|---|---|
| 11 | Cphy0764 | 986994 ... 988166 | Med | Uncharacterized ABC-type transport system, periplasmic component/surface lipoprotein |
| | Cphy0765 | 988605 ... 990140 | COG3845 | ABC-type uncharacterized transport systems, ATPase components |
| | Cphy0766 | 990133 ... 991233 | COG4603 | ABC-type uncharacterized transport system, permease component |
| | Cphy0767 | 991233 ... 992192 | COG1079 | Uncharacterized ABC-type transport system, permease component |
| | Cphy0768 | 992375 ... 993160 | AraC | AraC-type DNA-binding domain-containing proteins |
| | Cphy0769 | 993285 ... 994607 | CelF | Alpha-galactosidases/6-phospho-beta-glucosidases, family 4 of glycosyl hydrolases |
| 12 | Cphy0770 | 994704 ... 995759 | | NoCogMatch |
| | Cphy0771 | 995811 ... 996878 | COG4753 | Response regulator containing CheY-like receiver domain and AraC-type DNA-binding domain |
| | Cphy0772 | 996904 ... 998826 | COG2972 | Predicted signal transduction protein with a C-terminal ATPase domain |
| | Cphy0773 | 999105 ... 1000040 | LplB | ABC-type polysaccharide transport system, permease component |
| | Cphy0774 | 1000095 ... 1000940 | UgpE | ABC-type sugar transport system, permease component |
| | Cphy0775 | 1001005 ... 1002576 | UgpB | ABC-type sugar transport system, periplasmic component |
| | Cphy0776 | 1002623 ... 1003717 | COG1331 | Highly conserved protein containing a thioredoxin domain |
| 13 | Cphy0854 | 1089598 ... 1090047 | MarR | Transcriptional regulators |
| | Cphy0855 | 1090050 ... 1092317 | MdlB | ABC-type multidrug transport system, ATPase and permease components |
| | Cphy0856 | 1092314 ... 1094194 | MdlB | ABC-type multidrug transport system, ATPase and permease components |
| | Cphy0857 | 1094446 ... 1097148 | COG3459 | Cellobiose phosphorylase |
| | Cphy0858 | 1097657 ... 1098994 | COG5520 | O-Glycosyl hydrolase |
| | Cphy0859 | 1099142 ... 1099768 | | NoCogMatch |
| | Cphy0860 | 1099884 ... 1100825 | LplB | ABC-type polysaccharide transport system, permease component |
| | Cphy0861 | 1100837 ... 1101745 | UgpE | ABC-type sugar transport system, permease component |
| | Cphy0862 | 1101768 ... 1103474 | UgpB | ABC-type sugar transport system, periplasmic component |
| | Cphy0863 | 1103665 ... 1105464 | COG2972 | Predicted signal transduction protein with a C-terminal ATPase domain |
| | Cphy0864 | 1105480 ... 1106991 | COG4753 | Response regulator containing CheY-like receiver domain and AraC-type DNA-binding domain |
| 14 | Cphy0928 | 1182272 ... 1184572 | AraC | AraC-type DNA-binding domain-containing proteins |
| | Cphy0929 | 1184776 ... 1185768 | LplB | ABC-type polysaccharide transport system, permease component |
| | Cphy0930 | 1185782 ... 1186666 | UgpE | ABC-type sugar transport system, permease component |
| | Cphy0931 | 1186734 ... 1188368 | UgpB | ABC-type sugar transport system, periplasmic component |
| | Cphy0932 | 1188484 ... 1190736 | | NoCogMatch |
| | Cphy0933 | 1190798 ... 1191850 | | NoCogMatch |
| | Cphy0934 | 1191923 ... 1193098 | | NoCogMatch |
| 15 | Cphy1010 | 1276704 ... 1277816 | COG1476 | Predicted transcriptional regulators |
| | Cphy1011 | 1278019 ... 1278399 | | NoCogMatch |
| | Cphy1012 | 1278635 ... 1279747 | PurR | Transcriptional regulators |
| | Cphy1013 | 1280007 ... 1281491 | UgpB | ABC-type sugar transport system, periplasmic component |
| | Cphy1014 | 1281508 ... 1282416 | UgpA | ABC-type sugar transport systems, permease components |
| | Cphy1015 | 1282416 ... 1283258 | UgpE | ABC-type sugar transport system, permease component |
| 16 | Cphy1071 | 1354865 ... 1357051 | ManB | Beta-mannanase |
| | Cphy1074 | 1358682 ... 1360004 | UgpB | ABC-type sugar transport system, periplasmic component |
| | Cphy1075 | 1360064 ... 1360906 | UgpA | ABC-type sugar transport systems, permease components |
| | Cphy1076 | 1360906 ... 1361769 | UgpE | ABC-type sugar transport system, permease component |
| | Cphy1077 | 1361911 ... 1362948 | PurR | Transcriptional regulators |
| 17 | Cphy1118 | 1410194 ... 1411819 | UgpB | ABC-type sugar transport system, periplasmic component |
| | Cphy1119 | 1411890 ... 1412846 | LplB | ABC-type polysaccharide transport system, permease component |
| | Cphy1120 | 1412857 ... 1413726 | UgpE | ABC-type sugar transport system, permease component |
| | Cphy1121 | 1413748 ... 1414641 | COG2103 | Predicted sugar phosphate isomerase |
| | Cphy1122 | 1414707 ... 1415564 | RpiR | Transcriptional regulators |
| | Cphy1123 | 1415584 ... 1416768 | COG2377 | Predicted molecular chaperone distantly related to HSP70-fold metalloproteases |
| | Cphy1124 | 1416904 ... 1418049 | COG3876 | Uncharacterized protein conserved in bacteria |
| | Cphy1125 | 1418251 ... 1419804 | BglX | Beta-glucosidase-related glycosidases |
| 18 | Cphy1390 | 1729845 ... 1730771 | UgpA | ABC-type sugar transport systems, permease components |
| | Cphy1391 | 1730803 ... 1731633 | UgpE | ABC-type sugar transport system, permease component |
| | Cphy1392 | 1731696 ... 1733045 | UgpB | ABC-type sugar transport system, periplasmic component |
| | Cphy1393 | 1733168 ... 1734928 | COG2972 | Predicted signal transduction protein with a C-terminal ATPase domain |
| | Cphy1394 | 1734977 ... 1736548 | COG4753 | Response regulator containing CheY-like receiver domain and AraC-type DNA-binding domain |
| | Cphy1395 | 1736693 ... 1738969 | | NoCogMatch |

TABLE 7-continued

Predicted ABC-transporters and other proteins/domains in *C. phytofermentans*

| No. | JGI No. | Location | COG | COG Description |
|---|---|---|---|---|
| 19 | Cphy1679 | 2059856 . . . 2060530 | OmpR | Response regulators consisting of a CheY-like receiver domain and a winged-helix DNA-binding domain |
|  | Cphy1680 | 2060527 . . . 2061597 | BaeS | Signal transduction histidine kinase |
|  | Cphy1681 | 2061728 . . . 2063485 | MdlB | ABC-type multidrug transport system, ATPase and permease components |
|  | Cphy1682 | 2063482 . . . 2065323 | MdlB | ABC-type multidrug transport system, ATPase and permease components |
|  | Cphy1683 | 2065548 . . . 2066213 | AraC | AraC-type DNA-binding domain-containing proteins |
|  | Cphy1685 | 2067701 . . . 2068645 |  | NoCogMatch |
|  | Cphy1686 | 2068969 . . . 2070048 | COG2706 | 3-carboxymuconate cyclase |
|  | Cphy1687 | 2070592 . . . 2071602 | CDA1 | Predicted xylanase/chitin deacetylase |
|  | Cphy1688 | 2071762 . . . 2073555 | COG3292 | Predicted periplasmic ligand-binding sensor domain |
| 20 | Cphy1706 | 2092890 . . . 2095226 | AraC | AraC-type DNA-binding domain-containing proteins |
|  | Cphy1707 | 2095571 . . . 2097463 | DraG | ADP-ribosylglycohydrolase |
|  | Cphy1708 | 2097665 . . . 2099221 | UgpB | ABC-type sugar transport system, periplasmic component |
|  | Cphy1709 | 2099418 . . . 2100341 | LplB | ABC-type polysaccharide transport system, permease component |
|  | Cphy1710 | 2100360 . . . 2101262 | UgpE | ABC-type sugar transport system, permease component |
|  | Cphy1711 | 2101420 . . . 2103282 | PGU1 | Endopygalactorunase |
|  | Cphy1712 | 2103332 . . . 2104336 | Aes | Esterase/lipase |
|  | Cphy1713 | 2104536 . . . 2105900 |  | NoCogMatch |
|  | Cphy1714 | 2106148 . . . 2109003 | COG4724 | Endo-beta-N-acetylglucosaminidase D |
|  | Cphy1715 | 2109418 . . . 2110368 | LplB | ABC-type polysaccharide transport system, permease component |
|  | Cphy1716 | 2110380 . . . 2111312 | UgpE | ABC-type sugar transport system, permease component |
|  | Cphy1717 | 2111371 . . . 2112876 | UgpB | ABC-type sugar transport system, periplasmic component |
|  | Cphy1720 |  |  | glycoside hydrolase family 38 |
|  | Cphy1719 |  |  | hypothetical protein |
|  | Cphy1718 |  |  | glycosidase PH1107-related |
| 21 | Cphy1873 | 2302530 . . . 2305805 | COG1572 | Uncharacterized conserved protein |
|  | Cphy1874 | 2305913 . . . 2308174 | ATH1 | Trehalose and maltose hydrolases (possible phosphorylases) |
|  | Cphy1875 | 2308280 . . . 2308927 | COG0637 | Predicted phosphatase/phosphohexomutase |
|  | Cphy1876 | 2309264 . . . 2310301 | PurR | Transcriptional regulators |
|  | Cphy1877 | 2310355 . . . 2312748 | COG1501 | Alpha-glucosidases, family 31 of glycosyl hydrolases |
|  | Cphy1878 | 2312810 . . . 2314963 | Tar | Methyl-accepting chemotaxis protein |
|  | Cphy1879 | 2315244 . . . 2316557 | MalE | Maltose-binding periplasmic proteins/domains |
|  | Cphy1880 | 2316885 . . . 2318273 | UgpA | ABC-type sugar transport systems, permease components |
|  | Cphy1881 | 2318273 . . . 2319553 | MalG | ABC-type maltose transport systems, permease component |
|  | Cphy1882 | 2319649 . . . 2323881 |  | NoCogMatch |
|  | Cphy1883 | 2324145 . . . 2325200 | PurR | Transcriptional regulators |
| 22 | Cphy1915 | 2362169 . . . 2364496 | AraC | AraC-type DNA-binding domain-containing proteins |
|  | Cphy1916 | 2364818 . . . 2365780 | LplB | ABC-type polysaccharide transport system, permease component |
|  | Cphy1917 | 2365793 . . . 2366710 | UgpE | ABC-type sugar transport system, permease component |
|  | Cphy1918 | 2366768 . . . 2368441 | UgpB | ABC-type sugar transport system, periplasmic component |
|  | Cphy1919 | 2369079 . . . 2370116 | COG4225 | Predicted unsaturated glucuronyl hydrolase involved in regulation of bacterial surface properties, and related proteins |
| 23 | Cphy2187 | 2700406 . . . 2702664 | AraC | AraC-type DNA-binding domain-containing proteins |
|  | Cphy2188 | 2702785 . . . 2703105 |  | NoCogMatch |
|  | Cphy2189 | 2703144 . . . 2704676 | CcdA | Cytochrome c biogenesis protein |
|  | Cphy2190 | 2704764 . . . 2706071 | COG3669 | Alpha-L-fucosidase |
|  | Cphy2191 | 2706212 . . . 2707117 | UgpE | ABC-type sugar transport system, permease component |
|  | Cphy2192 | 2707130 . . . 2708053 | LplB | ABC-type polysaccharide transport system, permease component |
|  | Cphy2193 | 2708129 . . . 2709802 | UgpB | ABC-type sugar transport system, periplasmic component |
| 24 | Cphy2265 | 2791741 . . . 2793189 | UgpB | ABC-type sugar transport system, periplasmic component |
|  | Cphy2266 | 2793236 . . . 2795134 |  | NoCogMatch |
|  | Cphy2267 | 2795272 . . . 2796264 | UgpE | ABC-type sugar transport system, permease component |
|  | Cphy2268 | 2796278 . . . 2797195 | UgpA | ABC-type sugar transport systems, permease components |
|  | Cphy2269 | 2797161 . . . 2799770 |  | NoCogMatch |
|  | Cphy2272 | 2801915 . . . 2802787 | UgpE | ABC-type sugar transport system, permease component |
|  | Cphy2273 | 2802804 . . . 2803739 | UgpA | ABC-type sugar transport systems, permease components |
|  | Cphy2274 | 2803758 . . . 2806796 | UgpB | ABC-type sugar transport system, periplasmic component |
|  | Cphy2275 | 2806789 . . . 2807427 | COG5578 | Predicted integral membrane protein |
|  | Cphy2276 | 2807484 . . . 2809082 | ManB | Beta-mannanase |
|  | Cphy2277 | 2809660 . . . 2810001 | markorf1779 | Hypothetical protein |
|  | Cphy2278 | 2810437 . . . 2811483 | PurR | Transcriptional regulators |

TABLE 7-continued

Predicted ABC-transporters and other proteins/domains in *C. phytofermentans*

| No. | JGI No. | Location | COG | COG Description |
|---|---|---|---|---|
| 25 | Cphy2304 | 2836995 . . . 2840126 | PulA | Type II secretory pathway, pullulanase PulA and related glycosidases |
|  | Cphy2305 | 2840111 . . . 2840968 |  | NoCogMatch |
|  | Cphy2306 | 2840949 . . . 2841791 | MalG | ABC-type maltose transport systems, permease component |
|  | Cphy2307 | 2841802 . . . 2843130 | UgpA | ABC-type sugar transport systems, permease components |
|  | Cphy2308 | 2843299 . . . 2844621 | MalE | Maltose-binding periplasmic proteins/domains |
| 26 | Cphy2338 | 2882581 . . . 2883465 | AraC | AraC-type DNA-binding domain-containing proteins |
|  | Cphy2339 | 2883550 . . . 2884353 | LolE | ABC-type transport system, involved in lipoprotein release, permease component |
|  | Cphy2340 | 2884437 . . . 2885246 | LolE | ABC-type transport system, involved in lipoprotein release, permease component |
|  | Cphy2341 | 2885548 . . . 2887212 | AmyA | Glycosidases |
|  | Cphy2342 | 2887378 . . . 2888994 | AmyA | Glycosidases |
|  | Cphy2343 | 2889298 . . . 2891253 | GDB1 | Glycogen debranching enzyme |
|  | Cphy2344 | 2891543 . . . 2893270 | AmyA | Glycosidases |
|  | Cphy2345 | 2893664 . . . 2894530 | MalG | ABC-type maltose transport systems, permease component |
|  | Cphy2346 | 2894530 . . . 2895924 | UgpA | ABC-type sugar transport systems, permease components |
| 27 | Cphy2567 | 3133582 . . . 3135006 | PGU1 | Endopygalactorunase |
|  | Cphy2568 | 3135310 . . . 3135972 | COG1600 | Uncharacterized Fe—S protein |
|  | Cphy2569 | 3136132 . . . 3137703 | UgpB | ABC-type sugar transport system, periplasmic component |
|  | Cphy2570 | 3137758 . . . 3138693 | UgpE | ABC-type sugar transport system, permease component |
|  | Cphy2571 | 3138707 . . . 3139672 | LplB | ABC-type polysaccharide transport system, permease component |
|  | Cphy2572 | 3140149 . . . 3141216 | ChiA | Chitinase |
| 28 | Cphy2731 | 3321178 . . . 3322029 | UgpE | ABC-type sugar transport system, permease component |
|  | Cphy2732 | 3322042 . . . 3322992 | LplB | ABC-type polysaccharide transport system, permease component |
|  | Cphy2733 | 3323144 . . . 3324745 | UgpB | ABC-type sugar transport system, periplasmic component |
|  | Cphy2734 | 3325192 . . . 3327486 | AraC | AraC-type DNA-binding domain-containing proteins |
|  | Cphy2735 | 3327576 . . . 3328295 | TesA | Lysophospholipase L1 and related esterases |
|  | Cphy2736 | 3328548 . . . 3330104 | PGU1 | Endopygalactorunase |
| 29 | Cphy3009 | 3672467 . . . 3674620 | BglX | Beta-glucosidase-related glycosidases |
|  | Cphy3010 | 3674634 . . . 3675599 | XynA | Beta-1,4-xylanase |
|  | Cphy3011 | 3676460 . . . 3678076 | XynB | Beta-xylosidase |
|  | Cphy3012 | 3678276 . . . 3679193 | SufB | ABC-type transport system involved in Fe—S cluster assembly, permease component |
|  | Cphy3013 | 3679197 . . . 3679919 | SufC | ABC-type transport system involved in Fe—S cluster assembly, ATPase component |
| 30 | Cphy3066 | 3748299 . . . 3750080 | MdlB | ABC-type multidrug transport system, ATPase and permease components |
|  | Cphy3067 | 3750058 . . . 3751908 | MdlB | ABC-type multidrug transport system, ATPase and permease components |
|  | Cphy3068 | 3751920 . . . 3752993 |  | NoCogMatch |
|  | Cphy3069 | 3753565 . . . 3754962 | CDA1 | Predicted xylanase/chitin deacetylase |
| 31 | Cphy3102 | 3792846 . . . 3793784 | COG1216 | Predicted glycosyltransferases |
|  | Cphy3103 | 3793820 . . . 3794788 | COG1215 | Glycosyltransferases, probably involved in cell wall biogenesis |
|  | Cphy3104 | 3794965 . . . 3796023 | COG1123 | ATPase components of various ABC-type transport systems, contain duplicated ATPase |
|  | Cphy3105 | 3796156 . . . 3797211 | DppD | ABC-type dipeptide/oligopeptide/nickel transport system, ATPase component |
|  | Cphy3106 | 3797424 . . . 3798398 | DppC | ABC-type dipeptide/oligopeptide/nickel transport systems, permease components |
|  | Cphy3107 | 3798399 . . . 3799337 | DppB | ABC-type dipeptide/oligopeptide/nickel transport systems, permease components |
|  | Cphy3108 | 3799364 . . . 3801211 | OppA | ABC-type oligopeptide transport system, periplasmic component |
|  | Cphy3109 | 3802071 . . . 3803957 | Acm | Lyzozyme M1 (1,4-beta-N-acetylmuramidase) |
| 32 | Cphy3207 | 3910130 . . . 3911275 | CelA | Endoglucanase Y |
|  | Cphy3208 | 3911468 . . . 3912373 | UgpE | ABC-type sugar transport system, permease component |
|  | Cphy3209 | 3912465 . . . 3913424 | LplB | ABC-type polysaccharide transport system, permease component |
|  | Cphy3210 | 3913601 . . . 3915310 | UgpB | ABC-type sugar transport system, periplasmic component |
|  | Cphy3211 | 3915499 . . . 3917145 | COG4753 | Response regulator containing CheY-like receiver domain and AraC-type DNA-binding domain |
|  | Cphy3212 | 3917186 . . . 3918976 | COG2972 | Predicted signal transduction protein with a C-terminal ATPase domain |
|  | Cphy3213 | 3919325 . . . 3919876 |  | NoCogMatch |
|  | Cphy3217 | 3921799 . . . 3923274 | PGU1 | Endopygalactorunase |

TABLE 7-continued

Predicted ABC-transporters and other proteins/domains in *C. phytofermentans*

| No. | JGI No. | Location | COG | COG Description |
|---|---|---|---|---|
| 33 | Cphy3239 | 3943604 ... 3945511 | Chb | N-acetyl-beta-hexosaminidase |
|  | Cphy3240 | 3945691 ... 3947259 | UgpB | ABC-type sugar transport system, periplasmic component |
|  | Cphy3241 | 3947325 ... 3948227 | UgpE | ABC-type sugar transport system, permease component |
|  | Cphy3242 | 3948227 ... 3949159 | LplB | ABC-type polysaccharide transport system, permease component |
| 34 | Cphy3309 | 4028258 ... 4028884 |  | NoCogMatch |
|  | Cphy3310 | 4028993 ... 4030549 | PGU1 | Endopygalacturonase |
|  | Cphy3311 | 4030600 ... 4031262 | COG0637 | Predicted phosphatase/phosphohexomutase |
|  | Cphy3312 | 4031558 ... 4032568 | PurR | Transcriptional regulators |
|  | Cphy3313 | 4032640 ... 4034886 | ATH1 | Trehalose and maltose hydrolases (possible phosphorylases) |
|  | Cphy3314 | 4035015 ... 4037432 | ATH1 | Trehalose and maltose hydrolases (possible phosphorylases) |
|  | Cphy3315 | 4037436 ... 4038314 | UgpE | ABC-type sugar transport system, permease component |
|  | Cphy3316 | 4038325 ... 4039221 | UgpA | ABC-type sugar transport systems, permease components |
|  | Cphy3317 | 4039364 ... 4040842 | UgpB | ABC-type sugar transport system, periplasmic component |
|  | Cphy3318 | 4041326 ... 4041751 | MarR | Transcriptional regulators |
| 35 | Cphy3327 | 4049796 ... 4050236 | COG4753 | Response regulator containing CheY-like receiver domain and AraC-type DNA-binding domain |
|  | Cphy3328 | 4050701 ... 4050982 |  | NoCogMatch |
|  | Cphy3329 | 4051097 ... 4054015 | BglX | Beta-glucosidase-related glycosidases |
|  | Cphy3330 | 4054141 ... 4054431 |  | NoCogMatch |
|  | Cphy3331 | 4055168 ... 4057156 | SalY | ABC-type antimicrobial peptide transport system, permease component |
|  | Cphy3332 | 4057149 ... 4057928 | SalX | ABC-type antimicrobial peptide transport system, ATPase component |
|  | Cphy3333 | 4058214 ... 4059266 | BaeS | Signal transduction histidine kinase |
|  | Cphy3334 | 4059285 ... 4059956 | OmpR | Response regulators consisting of a CheY-like receiver domain and a winged-helix DNA-binding domain |
| 36 | Cphy3395 | 4154158 ... 4154739 | AcrR | Transcriptional regulator |
|  | Cphy3396 | 4154932 ... 4156332 | CelF | Alpha-galactosidases/6-phospho-beta-glucosidases, family 4 of glycosyl hydrolases |
|  | Cphy3397 | 4156675 ... 4157571 | AraC | AraC-type DNA-binding domain-containing proteins |
|  | Cphy3398 | 4157639 ... 4159183 | XynB | Beta-xylosidase |
|  | Cphy3399 | 4159229 ... 4161427 | ATH1 | Trehalose and maltose hydrolases (possible phosphorylases) |
|  | Cphy3400 | 4161559 ... 4162410 | UgpE | ABC-type sugar transport system, permease component |
|  | Cphy3401 | 4162423 ... 4163340 | UgpA | ABC-type sugar transport systems, permease components |
|  | Cphy3402 | 4163470 ... 4164825 | UgpB | ABC-type sugar transport system, periplasmic component |
|  | Cphy3403 | 4165352 ... 4166407 |  | NoCogMatch |
| 37 | Cphy3404 | 4166683 ... 4168008 | COG5520 | O-Glycosyl hydrolase |
|  | Cphy3405 | 4168051 ... 4168812 | COG4753 | Response regulator containing CheY-like receiver domain and AraC-type DNA-binding domain |
|  | Cphy3406 | 4168817 ... 4170628 | COG2972 | Predicted signal transduction protein with a C-terminal ATPase domain |
|  | Cphy3407 | 4170711 ... 4171556 | UgpE | ABC-type sugar transport system, permease component |
|  | Cphy3408 | 4171564 ... 4172445 | UgpA | ABC-type sugar transport systems, permease components |
|  | Cphy3409 | 4172661 ... 4174016 | UgpB | ABC-type sugar transport system, periplasmic component |
| 38 | Cphy3568 | 4405037 ... 4406263 | UgpE | ABC-type sugar transport system, permease component |
|  | Cphy3569 | 4406276 ... 4407250 | LplB | ABC-type polysaccharide transport system, permease component |
|  | Cphy3570 | 4407401 ... 4409101 | UgpB | ABC-type sugar transport system, periplasmic component |
|  | Cphy3571 | 4409134 ... 4411029 | Chb | N-acetyl-beta-hexosaminidase |
| 39 | Cphy3585 | 4427384 ... 4428406 | PurR | Transcriptional regulators |
|  | Cphy3586 | 4428652 ... 4430196 | COG3867 | Arabinogalactan endo-1,4-beta-galactosidase |
|  | Cphy3587 | 4430612 ... 4432444 |  | NoCogMatch |
|  | Cphy3588 | 4432750 ... 4433562 | UgpE | ABC-type sugar transport system, permease component |
|  | Cphy3589 | 4433555 ... 4434439 | UgpA | ABC-type sugar transport systems, permease components |
|  | Cphy3590 | 4434607 ... 4435923 | UgpB | ABC-type sugar transport system, periplasmic component |
|  | Cphy3591 | 4436346 ... 4438502 | Tar | Methyl-accepting chemotaxis protein |
| 40 | Cphy3778 | 4630973 ... 4631749 | COG3694 | ABC-type uncharacterized transport system, permease component |
|  | Cphy3779 | 4631756 ... 4632532 | COG4587 | ABC-type uncharacterized transport system, permease component |
|  | Cphy3780 | 4632622 ... 4633419 | COG4586 | ABC-type uncharacterized transport system, ATPase component |
|  | Cphy3781 | 4633787 ... 4635553 | MdlB | ABC-type multidrug transport system, ATPase and permease components |
|  | Cphy3782 | 4635540 ... 4637324 | MdlB | ABC-type multidrug transport system, ATPase and permease components |
|  | Cphy3783 | 4637694 ... 4638797 | LytR | Transcriptional regulator |
|  | Cphy3784 | 4638930 ... 4639193 |  | NoCogMatch |
|  | Cphy3785 | 4639618 ... 4641696 | COG1501 | Alpha-glucosidases, family 31 of glycosyl hydrolases |

TABLE 7-continued

Predicted ABC-transporters and other proteins/domains in *C. phytofermentans*

| No. | JGI No. | Location | COG | COG Description |
|---|---|---|---|---|
| 41 | Cphy3854 | 4724145...4726538 | COG3459 | Cellobiose phosphorylase |
| | Cphy3855 | 4726828...4728252 | {ManB} | Phosphomannomutase |
| | Cphy3857 | 4730021...4731766 | LytS | Putative regulator of cell autolysis |
| | Cphy3858 | 4731867...4733216 | UgpB | ABC-type sugar transport system, periplasmic component |
| | Cphy3859 | 4733354...4734235 | UgpA | ABC-type sugar transport systems, permease components |
| | Cphy3860 | 4734248...4735123 | UgpE | ABC-type sugar transport system, permease component |
| | Cphy3861 | 4735380...4736159 | COG4753 | Response regulator containing CheY-like receiver domain and AraC-type DNA-binding domain |
| | Cphy3862 | 4736925...4744298 | XynA | Beta-1,4-xylanase |

Certain embodiments include the use of nucleic acids encoding predicted ABC-transporters that transport any product of polymer hydrolysis. Such products of hydrolysis can include monosaccharides, for example, glucose, mannose, fucose, galactose, arabinose, rhamnose, and xylose; disaccharides, for example, trehalose, maltose, lactose, sucrose, cellobiose; xylobiose, and oligosaccharides, for example, cellotriose, cellotetraose, xylotriose, xylotetraose, inulin, raffinose, and melezitose.

Certain embodiments include predicted ABC-transporters that transport cellobiose, for example, predicted ABC-transporters encoded by Cphy2464, Cphy2465, and Cphy2466.

Transcriptional Regulators

Some embodiments described herein relate to polynucleotides, polynucleotide cassettes, expression cassettes, expression vectors, and microorganisms comprising nucleic acids identified in *C. phytofermentans* that encode transcriptional regulators. Other embodiments relate to methods for producing fuel utilizing the polynucleotides, polynucleotide cassettes, expression cassettes, expression vectors, and microorganisms including nucleic acids identified in *C. phytofermentans* encoding transcriptional regulators.

Transcriptional regulators identified in *C. phytofermentans* include members of the AraC and PurR families. AraC regulators can include transcriptional activators of genes involved in carbon metabolism (Gallegos M. T. et al. AraC/XylS Family of Transcriptional Regulators. *Microbiol. Mol. Biol. Rev.* 61, 393-410 (1997)). PurR regulators can include members of the lactose repressor family (Ramos, J. L. et al. The TetR family of transcriptional repressors. *Microbiol. Mol. Biol. Rev.* 69, 326-356 (2005)).

Some embodiments include the predicted transcriptional regulators shown in Table 8.

TABLE 8

Predicted transcriptional regulators in *C. phytofermentans*

| JGI No. | COG | COG Description |
|---|---|---|
| Cphy0029 | AraC | AraC-type DNA-binding domain-containing proteins |
| Cphy0171 | AraC | AraC-type DNA-binding domain-containing proteins |
| Cphy0342 | AraC | AraC-type DNA-binding domain-containing proteins |
| Cphy0385 | AraC | AraC-type DNA-binding domain-containing proteins |
| Cphy0464 | AraC | AraC-type DNA-binding domain-containing proteins |
| Cphy0572 | AraC | AraC-type DNA-binding domain-containing proteins |
| Cphy0176 | AcrR | Transcriptional regulator |
| Cphy0461 | AcrR | Transcriptional regulator |
| Cphy0674 | AraC | AraC-type DNA-binding domain-containing proteins |
| Cphy0709 | AraC | AraC-type DNA-binding domain-containing proteins |
| Cphy0730 | AraC | AraC-type DNA-binding domain-containing proteins |
| Cphy0768 | AraC | AraC-type DNA-binding domain-containing proteins |
| Cphy0928 | AraC | AraC-type DNA-binding domain-containing proteins |
| Cphy0971 | AraC | AraC-type DNA-binding domain-containing proteins |
| Cphy0610 | AcrR | Transcriptional regulator |
| Cphy1148 | AraC | AraC-type DNA-binding domain-containing proteins |
| Cphy1165 | AraC | AraC-type DNA-binding domain-containing proteins |
| Cphy1168 | AraC | AraC-type DNA-binding domain-containing proteins |
| Cphy0667 | AcrR | Transcriptional regulator |
| Cphy0672 | AcrR | Transcriptional regulator |
| Cphy1364 | AcrR | Transcriptional regulator |
| Cphy1472 | AraC | AraC-type DNA-binding domain-containing proteins |
| Cphy1367 | AcrR | Transcriptional regulator |
| Cphy1513 | AcrR | Transcriptional regulator |
| Cphy1528 | AraC | AraC-type DNA-binding domain-containing proteins |
| Cphy1546 | AraC | AraC-type DNA-binding domain-containing proteins |
| Cphy1633 | AcrR | Transcriptional regulator |
| Cphy1683 | AraC | AraC-type DNA-binding domain-containing proteins |
| Cphy1706 | AraC | AraC-type DNA-binding domain-containing proteins |
| Cphy1762 | AcrR | Transcriptional regulator |
| Cphy1837 | AcrR | Transcriptional regulator |
| Cphy1838 | AcrR | Transcriptional regulator |
| Cphy1856 | AcrR | Transcriptional regulator |
| Cphy1864 | AcrR | Transcriptional regulator |
| Cphy1910 | AcrR | Transcriptional regulator |
| Cphy2667 | AcrR | Transcriptional regulator |

TABLE 8-continued

Predicted transcriptional regulators in *C. phytofermentans*

| JGI No. | COG | COG Description |
|---|---|---|
| Cphy3395 | AcrR | Transcriptional regulator |
| Cphy3621 | AcrR | Transcriptional regulator |
| Cphy1915 | AraC | AraC-type DNA-binding domain-containing proteins |
| Cphy2187 | AraC | AraC-type DNA-binding domain-containing proteins |
| Cphy2230 | AraC | AraC-type DNA-binding domain-containing proteins |
| Cphy2239 | AraC | AraC-type DNA-binding domain-containing proteins |
| Cphy2338 | AraC | AraC-type DNA-binding domain-containing proteins |
| Cphy2461 | AraC | AraC-type DNA-binding domain-containing proteins |
| Cphy2556 | AraC | AraC-type DNA-binding domain-containing proteins |
| Cphy0989 | ARO8 | Transcriptional regulators containing a DNA-binding HTH domain and an aminotransferase domain (MocR family) and their eukaryotic orthologs |
| Cphy1088 | ARO8 | Transcriptional regulators containing a DNA-binding HTH domain and an aminotransferase domain (MocR family) and their eukaryotic orthologs |
| Cphy2734 | AraC | AraC-type DNA-binding domain-containing proteins |
| Cphy2228 | ARO8 | Transcriptional regulators containing a DNA-binding HTH domain and an aminotransferase domain (MocR family) and their eukaryotic orthologs |
| Cphy1297 | ARO8 | Transcriptional regulators containing a DNA-binding HTH domain and an aminotransferase domain (MocR family) and their eukaryotic orthologs |
| Cphy1446 | ARO8 | Transcriptional regulators containing a DNA-binding HTH domain and an aminotransferase domain (MocR family) and their eukaryotic orthologs |
| Cphy3132 | AraC | AraC-type DNA-binding domain-containing proteins |
| Cphy3142 | AraC | AraC-type DNA-binding domain-containing proteins |
| Cphy3156 | AraC | AraC-type DNA-binding domain-containing proteins |
| Cphy3159 | AraC | AraC-type DNA-binding domain-containing proteins |
| Cphy3181 | AraC | AraC-type DNA-binding domain-containing proteins |
| Cphy3256 | AraC | AraC-type DNA-binding domain-containing proteins |
| Cphy0116 | ArsR | Predicted transcriptional regulators |
| Cphy3397 | AraC | AraC-type DNA-binding domain-containing proteins |
| Cphy0179 | ArsR | Predicted transcriptional regulators |
| Cphy1004 | ArsR | Predicted transcriptional regulators |
| Cphy1359 | ArsR | Predicted transcriptional regulators |
| Cphy2129 | ArsR | Predicted transcriptional regulators |
| Cphy2151 | ArsR | Predicted transcriptional regulators |
| Cphy2725 | COG1327 | Predicted transcriptional regulator, consists of a Zn-ribbon and ATP-cone domains |
| Cphy2664 | COG1329 | Transcriptional regulators, similar to M. xanthus CarD |
| Cphy2583 | COG1386 | Predicted transcriptional regulator containing the HTH domain |
| Cphy0065 | COG1476 | Predicted transcriptional regulators |
| Cphy0169 | COG1476 | Predicted transcriptional regulators |
| Cphy0954 | COG1476 | Predicted transcriptional regulators |
| Cphy1010 | COG1476 | Predicted transcriptional regulators |
| Cphy1967 | COG1476 | Predicted transcriptional regulators |
| Cphy2111 | COG1476 | Predicted transcriptional regulators |
| Cphy2424 | COG1476 | Predicted transcriptional regulators |
| Cphy0424 | COG1521 | Putative transcriptional regulator, homolog of Bvg accessory factor |
| Cphy1270 | COG1695 | Predicted transcriptional regulators |
| Cphy1963 | COG1695 | Predicted transcriptional regulators |
| Cphy2018 | COG1695 | Predicted transcriptional regulators |
| Cphy2071 | COG1695 | Predicted transcriptional regulators |
| Cphy2526 | COG1695 | Predicted transcriptional regulators |
| Cphy3164 | COG1695 | Predicted transcriptional regulators |
| Cphy3562 | COG1695 | Predicted transcriptional regulators |
| Cphy0073 | COG1725 | Predicted transcriptional regulators |
| Cphy0185 | COG1725 | Predicted transcriptional regulators |
| Cphy1279 | COG1725 | Predicted transcriptional regulators |
| Cphy2235 | COG1725 | Predicted transcriptional regulators |
| Cphy2319 | COG1725 | Predicted transcriptional regulators |
| Cphy3464 | COG1725 | Predicted transcriptional regulators |
| Cphy3903 | COG1725 | Predicted transcriptional regulators |
| Cphy1405 | COG1733 | Predicted transcriptional regulators |
| Cphy1661 | COG1733 | Predicted transcriptional regulators |
| Cphy1850 | COG1733 | Predicted transcriptional regulators |
| Cphy0009 | COG1959 | Predicted transcriptional regulator |
| Cphy1824 | COG1959 | Predicted transcriptional regulator |
| Cphy0991 | COG2378 | Predicted transcriptional regulator |
| Cphy1647 | COG2378 | Predicted transcriptional regulator |
| Cphy2042 | COG2378 | Predicted transcriptional regulator |
| Cphy3341 | COG2378 | Predicted transcriptional regulator |
| Cphy0512 | COG3437 | Response regulator containing a CheY-like receiver domain and an HD-GYP domain |
| Cphy1859 | COG3655 | Predicted transcriptional regulator |
| Cphy2069 | COG3682 | Predicted transcriptional regulator |
| Cphy2324 | COG3682 | Predicted transcriptional regulator |
| Cphy2354 | COG3682 | Predicted transcriptional regulator |
| Cphy3800 | COG4109 | Predicted transcriptional regulator containing CBS domains |

TABLE 8-continued

Predicted transcriptional regulators in *C. phytofermentans*

| JGI No. | COG | COG Description |
|---|---|---|
| Cphy0293 | COG4753 | Response regulator containing CheY-like receiver domain and AraC-type DNA-binding domain |
| Cphy0496 | COG4753 | Response regulator containing CheY-like receiver domain and AraC-type DNA-binding domain |
| Cphy0525 | COG4753 | Response regulator containing CheY-like receiver domain and AraC-type DNA-binding domain |
| Cphy0579 | COG4753 | Response regulator containing CheY-like receiver domain and AraC-type DNA-binding domain |
| Cphy0618 | COG4753 | Response regulator containing CheY-like receiver domain and AraC-type DNA-binding domain |
| Cphy0771 | COG4753 | Response regulator containing CheY-like receiver domain and AraC-type DNA-binding domain |
| Cphy0864 | COG4753 | Response regulator containing CheY-like receiver domain and AraC-type DNA-binding domain |
| Cphy1394 | COG4753 | Response regulator containing CheY-like receiver domain and AraC-type DNA-binding domain |
| Cphy1583 | COG4753 | Response regulator containing CheY-like receiver domain and AraC-type DNA-binding domain |
| Cphy1722 | COG4753 | Response regulator containing CheY-like receiver domain and AraC-type DNA-binding domain |
| Cphy2007 | COG4753 | Response regulator containing CheY-like receiver domain and AraC-type DNA-binding domain |
| Cphy2141 | COG4753 | Response regulator containing CheY-like receiver domain and AraC-type DNA-binding domain |
| Cphy2253 | COG4753 | Response regulator containing CheY-like receiver domain and AraC-type DNA-binding domain |
| Cphy3034 | COG4753 | Response regulator containing CheY-like receiver domain and AraC-type DNA-binding domain |
| Cphy3211 | COG4753 | Response regulator containing CheY-like receiver domain and AraC-type DNA-binding domain |
| Cphy3282 | COG4753 | Response regulator containing CheY-like receiver domain and AraC-type DNA-binding domain |
| Cphy3327 | COG4753 | Response regulator containing CheY-like receiver domain and AraC-type DNA-binding domain |
| Cphy3405 | COG4753 | Response regulator containing CheY-like receiver domain and AraC-type DNA-binding domain |
| Cphy3697 | COG4753 | Response regulator containing CheY-like receiver domain and AraC-type DNA-binding domain |
| Cphy3861 | COG4753 | Response regulator containing CheY-like receiver domain and AraC-type DNA-binding domain |
| Cphy3887 | COG4753 | Response regulator containing CheY-like receiver domain and AraC-type DNA-binding domain |
| Cphy0782 | COG4800 | Predicted transcriptional regulator with an HTH domain |
| Cphy2167 | COG4977 | Transcriptional regulator containing an amidase domain and an AraC-type DNA-binding HTH domain |
| Cphy1848 | COG4978 | Transcriptional regulator, effector-binding domain/component |
| Cphy1313 | FadR | Transcriptional regulators |
| Cphy1561 | FadR | Transcriptional regulators |
| Cphy3829 | FadR | Transcriptional regulators |
| Cphy1187 | GlpR | Transcriptional regulators of sugar metabolism |
| Cphy2030 | GlpR | Transcriptional regulators of sugar metabolism |
| Cphy0655 | GntR | Transcriptional regulators |
| Cphy3095 | GntR | Transcriptional regulators |
| Cphy3764 | GntR | Transcriptional regulators |
| Cphy0097 | HipB | Predicted transcriptional regulators |
| Cphy0275 | HipB | Predicted transcriptional regulators |
| Cphy0510 | HipB | Predicted transcriptional regulators |
| Cphy2912 | HipB | Predicted transcriptional regulators |
| Cphy2313 | HrcA | Transcriptional regulator of heat shock gene |
| Cphy0149 | Lrp | Transcriptional regulators |
| Cphy1811 | Lrp | Transcriptional regulators |
| Cphy1102 | LysR | Transcriptional regulator |
| Cphy1229 | LysR | Transcriptional regulator |
| Cphy1477 | LysR | Transcriptional regulator |
| Cphy1757 | LysR | Transcriptional regulator |
| Cphy1783 | LysR | Transcriptional regulator |
| Cphy1902 | LysR | Transcriptional regulator |
| Cphy2431 | LysR | Transcriptional regulator |
| Cphy3040 | LysR | Transcriptional regulator |
| Cphy1293 | LysR | Transcriptional regulator |
| Cphy2156 | LysR | Transcriptional regulator |
| Cphy3352 | LysR | Transcriptional regulator |
| Cphy3361 | LysR | Transcriptional regulator |
| Cphy2557 | LytR | Transcriptional regulator |
| Cphy2794 | LytR | Transcriptional regulator |
| Cphy2795 | LytR | Transcriptional regulator |

TABLE 8-continued

Predicted transcriptional regulators in *C. phytofermentans*

| JGI No. | COG | COG Description |
|---|---|---|
| Cphy3783 | LytR | Transcriptional regulator |
| Cphy3892 | LytR | Transcriptional regulator |
| Cphy0854 | MarR | Transcriptional regulators |
| Cphy1696 | MarR | Transcriptional regulators |
| Cphy1755 | MarR | Transcriptional regulators |
| Cphy1844 | MarR | Transcriptional regulators |
| Cphy1979 | MarR | Transcriptional regulators |
| Cphy2138 | MarR | Transcriptional regulators |
| Cphy2555 | MarR | Transcriptional regulators |
| Cphy2561 | MarR | Transcriptional regulators |
| Cphy2661 | MarR | Transcriptional regulators |
| Cphy3318 | MarR | Transcriptional regulators |
| Cphy3835 | MarR | Transcriptional regulators |
| Cphy3246 | NagC | Transcriptional regulator/sugar kinase |
| Cphy0329 | NagC | Transcriptional regulator/sugar kinase |
| Cphy1578 | NagC | Transcriptional regulator/sugar kinase |
| Cphy3420 | NagC | Transcriptional regulator/sugar kinase |
| Cphy3573 | NagC | Transcriptional regulator/sugar kinase |
| Cphy1273 | PspC | Putative stress-responsive transcriptional regulator |
| Cphy0484 | PurR | Transcriptional regulators |
| Cphy0568 | PurR | Transcriptional regulators |
| Cphy0595 | PurR | Transcriptional regulators |
| Cphy0698 | PurR | Transcriptional regulators |
| Cphy1077 | PurR | Transcriptional regulators |
| Cphy1821 | PurR | Transcriptional regulators |
| Cphy1876 | PurR | Transcriptional regulators |
| Cphy1883 | PurR | Transcriptional regulators |
| Cphy2278 | PurR | Transcriptional regulators |
| Cphy2351 | PurR | Transcriptional regulators |
| Cphy3312 | PurR | Transcriptional regulators |
| Cphy3585 | PurR | Transcriptional regulators |
| Cphy1454 | PurR | Transcriptional regulators |
| Cphy1012 | PurR | Transcriptional regulators |
| Cphy0590 | PurR | Transcriptional regulators |
| Cphy2353 | PurR | Transcriptional regulators |
| Cphy2467 | PurR | Transcriptional regulators |
| Cphy2742 | PurR | Transcriptional regulators |
| Cphy3700 | PurR | Transcriptional regulators |
| Cphy1265 | RocR | Transcriptional regulator containing PAS, AAA-type ATPase, and DNA-binding domains |
| Cphy1122 | RpiR | Transcriptional regulators |
| Cphy3564 | RpiR | Transcriptional regulators |
| Cphy0098 | SoxR | Predicted transcriptional regulators |
| Cphy0276 | SoxR | Predicted transcriptional regulators |
| Cphy0738 | SoxR | Predicted transcriptional regulators |
| Cphy1008 | SoxR | Predicted transcriptional regulators |
| Cphy1410 | SoxR | Predicted transcriptional regulators |
| Cphy1458 | SoxR | Predicted transcriptional regulators |
| Cphy1609 | SoxR | Predicted transcriptional regulators |
| Cphy1613 | SoxR | Predicted transcriptional regulators |
| Cphy2039 | SoxR | Predicted transcriptional regulators |
| Cphy3049 | SoxR | Predicted transcriptional regulators |
| Cphy3623 | SoxR | Predicted transcriptional regulators |
| Cphy3713 | SoxR | Predicted transcriptional regulators |
| Cphy3755 | SoxR | Predicted transcriptional regulators |
| Cphy3934 | Spo0J | Predicted transcriptional regulators |
| Cphy1191 | TroR | Mn-dependent transcriptional regulator |

Certain embodiments include a predicted transcriptional regulator encoded by Cphy2467.

Combinations

Some embodiments described herein relate to polynucleotides, polynucleotide cassettes, expression cassettes, expression vectors, and organisms comprising more than one, e.g., two or more genes identified in *C. phytofermentans*. Some embodiments relate to methods for producing fuel utilizing the polynucleotides, polynucleotide cassettes, expression cassettes, expression vectors, and microorganisms comprising more than one gene, e.g., two or more genes, identified in *C. phytofermentans*.

Combinations can include polynucleotide cassettes containing more than one gene identified in *C. phytofermentans*. In such embodiments, any gene described herein can be utilized in combination with any other gene described herein. For example, any nucleic acid identified in *C. phytofermentans* that encodes a hydrolase can be utilized in combination with any nucleic acid identified in *C. phytofermentans* that encodes an ABC-transporter. In further embodiments, any nucleic acid encoding a hydrolase identified in *C. phytofermentans* can be utilized in combination with a nucleic acid encoding a cognizant ABC-transporter identified in *C. phytofermentans*, such as a nucleic acid encoding a xylanase combined with a nucleic acid encoding a xylose transporter.

As used herein, cognizant can refer to at least two genes associated with a particular biochemical pathway. For example, cognizant can refer to at least two genes where the product of the first gene can be the substrate for the second gene, and so forth. Advantages of utilizing cognizant genes include the ability to engender a recombinant organism with multiple activities encoded by a polynucleotide cassette, for example, an organism transformed with a polynucleotide cassette comprising a hydrolase and the cognizant ABC-transporter can hydrolase the particular substrate polymer for the hydrolase, and transport the hydrolyzed product into the cell via the cognizant ABC-transporter. One skilled in the art can identify examples of cognizant genes described herein.

In other embodiments, any nucleic acid identified in *C. phytofermentans* encoding a hydrolase can be utilized in combination with any nucleic acid identified in *C. phytofermentans* encoding a transcriptional regulator. In further embodiments, any nucleic acid encoding a hydrolase identified in *C. phytofermentans* can be utilized in combination with a nucleic acid encoding a cognizant transcriptional regulator identified in *C. phytofermentans*.

In particular embodiments, any nucleic acid identified in *C. phytofermentans* encoding an ABC-transporter can be utilized in combination with any nucleic acid identified in *C. phytofermentans* encoding a transcriptional regulator. In further embodiments, any nucleic acid encoding an ABC-transporter identified in *C. phytofermentans* can be utilized in combination with a nucleic acid encoding a cognizant transcriptional regulator identified in *C. phytofermentans*.

In some embodiments, any nucleic acid identified in *C. phytofermentans* encoding a hydrolase can be utilized in combination with any nucleic acid identified in *C. phytofermentans* encoding an ABC-transporter, and any nucleic acid identified in *C. phytofermentans* encoding a transcriptional regulator. In further embodiments, any nucleic acid encoding a hydrolase identified in *C. phytofermentans* can be utilized in combination with any nucleic acid encoding a cognizant ABC-transporter identified in *C. phytofermentans*, and any nucleic acid encoding a cognizant transcriptional regulator identified in *C. phytofermentans*.

In some embodiments, combinations can include the sequential use of more than one gene identified in *C. phytofermentans*. For example, an organism can be transformed with a polynucleotide comprising any gene described herein, and subsequently transformed with at least one different gene described herein.

Exemplary embodiments of polynucleotide cassettes comprising, or consisting essentially of, combinations of at least two genes are shown in FIG. 1. In one embodiment, the predicted hydrolase encoded by Cphy2276 can be combined with the predicted cognizant ABC-transporter domains encoded by Cphy2272, Cphy2273, and Cphy2274. In another embodiment, the predicted hydrolase encoded by Cphy3207 can be combined with the predicted cognizant ABC-transporter domains encoded by Cphy3210, Cphy3209, and Cphy3208, and the predicted cognizant transcriptional regulator encoded by Cphy3211, and the predicted cognizant signal transduction protein encoded by Cphy3212. In another embodiment, the predicted ABC-transporter domains encoded by Cphy0862, Cphy0861, and Cphy0860 can be combined with the predicted transcriptional regulator encoded by Cphy0864, and the predicted signal transduction protein encoded by Cphy0863. In another embodiment, the predicted ABC-transporter domains encoded by Cphy2466, Cphy2465, and Cphy2464 can be combined with the predicted transcriptional regulator encoded by Cphy2467. In another embodiment, the predicted hydrolase encoded by Cphy1877 can be combined with the predicted transcriptional regulator encoded by Cphy1876.

In more exemplary embodiments, polynucleotide cassettes, expression cassettes, expression vectors, and organisms comprising more than one gene can comprise gene clusters identified in *C. phytofermentans*. Such gene clusters can be identified using the methods described herein and the methods well known in the art. In some embodiments, genes and gene clusters can be identified by the degree of homology between clusters of orthologous groups of proteins (COG). Such genes and gene clusters can be included on cassettes or expressed together. Examples of gene clusters identified in *C. phytofermentans* are shown in Table 9.

TABLE 9

Gene Clusters Identified in *C. phytofermentans*

| Cluster | JGI No. | Location | COG | COG Description |
|---|---|---|---|---|
| 1 | Cphy1799 | 2214443 . . . 2216098 | COG3469 | Chitinase |
|   | Cphy1800 | 2216331 . . . 2218289 | ChiA | Chitinase |
| 2 | Cphy1528 | 1877364 . . . 1878218 | AraC | AraC-type DNA-binding domain-containing proteins |
|   | Cphy1529 | 1878477 . . . 1879796 | UgpB | ABC-type sugar transport system, periplasmic component |
|   | Cphy1530 | 1879890 . . . 1880777 | UgpA | ABC-type sugar transport systems, permease components |
|   | Cphy1531 | 1880788 . . . 1881615 | UgpE | ABC-type sugar transport system, permease component |
|   | Cphy1532 | 1881755 . . . 1882096 | COG5646 | Uncharacterized conserved protein |
| 3 | Cphy3206 | 3907719 . . . 3909908 | Tar | Methyl-accepting chemotaxis protein |
|   | Cphy3207 | 3910130 . . . 3911275 | CelA | Endoglucanase Y |
|   | Cphy3208 | 3911468 . . . 3912373 | UgpE | ABC-type sugar transport system, permease component |
|   | Cphy3209 | 3912465 . . . 3913424 | LplB | ABC-type polysaccharide transport system, permease component |
|   | Cphy3210 | 3913601 . . . 3915310 | UgpB | ABC-type sugar transport system, periplasmic component |
|   | Cphy3211 | 3915499 . . . 3917145 | COG4753 | Response regulator containing CheY-like receiver domain and AraC-type DNA-binding domain |
|   | Cphy3212 | 3917186 . . . 3918976 | COG2972 | Predicted signal transduction protein with a C-terminal ATPase domain |
| 4 | Cphy3367 | 4103996 . . . 4106953 | — | — |
|   | Cphy3368 | 4107033 . . . 4109792 | — | — |

TABLE 9-continued

Gene Clusters Identified in *C. phytofermentans*

| Cluster | JGI No. | Location | COG | COG Description |
|---|---|---|---|---|
| 5 | Cphy3858 | 4731867...4733216 | UgpB | ABC-type sugar transport system, periplasmic component |
|  | Cphy3859 | 4733354...4734235 | UgpA | ABC-type sugar transport systems, permease components |
|  | Cphy3860 | 4734248...4735123 | UgpE | ABC-type sugar transport system, permease component |
|  | Cphy3861 | 4735380...4736159 | COG4753 | Response regulator containing CheY-like receiver domain and AraC-type DNA-binding domain |
|  | Cphy3862 | 4736925...4744298 | XynA | Beta-1,4-xylanase |
| 6 | Cphy2272 | 2801915...2802787 | UgpE | ABC-type sugar transport system, permease component |
|  | Cphy2273 | 2802804...2803739 | UgpA | ABC-type sugar transport systems, permease components |
|  | Cphy2274 | 2803758...2806796 | UgpB | ABC-type sugar transport system, periplasmic component |
|  | Cphy2275 | 2806789...2807427 | COG5578 | Predicted integral membrane protein |
|  | Cphy2276 | 2807484...2809082 | ManB | Beta-mannanase |
| 7 | Cphy2464 | 3025234...3026121 | UgpE | ABC-type sugar transport system, permease component |
|  | Cphy2465 | 3026126...3027100 | UgpA | ABC-type sugar transport systems, permease components |
|  | Cphy2466 | 3027334...3028755 | UgpB | ABC-type sugar transport system, periplasmic component |
|  | Cphy2467 | 3028826...3029881 | PurR | Transcriptional regulators |
| 8 | Cphy1448 | 1788560...1789609 | PhnD | ABC-type phosphate/phosphonate transport system, periplasmic component |
|  | Cphy1449 | 1789748...1790512 | COG3638 | ABC-type phosphate/phosphonate transport system, ATPase component |
|  | Cphy1450 | 1790509...1791330 | COG3639 | ABC-type phosphate/phosphonate transport system, permease component |
|  | Cphy1451 | 1791345...1792154 | COG3639 | ABC-type phosphate/phosphonate transport system, permease component |
|  | Cphy1452 | 1792326...1793861 | UshA | 5'-nucleotidase/2',3'-cyclic phosphodiesterase and related esterases |
| 9 | Cphy1071 | 1354865...1357051 | ManB | Beta-mannanase |
|  | Cphy1074 | 1358682...1360004 | UgpB | ABC-type sugar transport system, periplasmic component |
|  | Cphy1075 | 1360064...1360906 | UgpA | ABC-type sugar transport systems, permease components |
|  | Cphy1076 | 1360906...1361769 | UgpE | ABC-type sugar transport system, permease component |
| 10 | Cphy1132 | 1424925...1425929 | RbsB | ABC-type sugar transport system, periplasmic component |
|  | Cphy1133 | 1426063...1427142 | AraH | Ribose/xylose/arabinose/galactoside ABC-type transport systems, permease components |
|  | Cphy1134 | 1427155...1428675 | MglA | ABC-type sugar transport system, ATPase component |
| 11 | Cphy1694 | 2078054...2081500 | — | — |
|  | Cphy1695 | 2081574...2082656 | WcaA | Glycosyltransferases involved in cell wall biogenesis |
| 12 | Cphy1876 | 2309264...2310301 | PurR | Transcriptional regulators |
|  | Cphy1877 | 2310355...2312748 | COG1501 | Alpha-glucosidases, family 31 of glycosyl hydrolases |
| 13 | Cphy2105 | 2602117...2602755 | — | — |
|  | Cphy2106 | 2603026...2603856 | COG1262 | Uncharacterized conserved protein |
|  | Cphy2107 | 2604341...2605282 | COG3708 | Uncharacterized protein conserved in bacteria |
|  | Cphy2108 | 2605495...2607915 | XynA | Beta-1,4-xylanase |
| 14 | Cphy2237 | 2756774...2758021 | GalK | Galactokinase |
|  | Cphy2238 | 2758041...2758286 | — | — |
|  | Cphy2239 | 2758623...2759510 | AraC | AraC-type DNA-binding domain-containing proteins |
|  | Cphy2240 | 2759556...2760221 | — | — |
|  | Cphy2241 | 2760521...2761603 | MglC | ABC-type glucose/galactose transport system, permease component |
|  | Cphy2242 | 2761619...2763118 | MglA | ABC-type sugar transport system, ATPase component |
|  | Cphy2243 | 2763191...2764294 | RbsB | ABC-type sugar transport system, periplasmic component |

TABLE 9-continued

Gene Clusters Identified in *C. phytofermentans*

| Cluster | JGI No. | Location | COG | COG Description |
|---|---|---|---|---|
| 15 | Cphy2262 | 2788055...2789236 | COG2942 | N-acyl-D-glucosamine 2-epimerase |
| | Cphy2263 | 2789493...2790608 | TesA | Lysophospholipase L1 and related esterases |
| | Cphy2264 | 2790617...2791639 | COG2152 | Predicted glycosylase |
| | Cphy2265 | 2791741...2793189 | UgpB | ABC-type sugar transport system, periplasmic component |
| | Cphy2266 | 2793236...2795134 | — | — |
| | Cphy2267 | 2795272...2796264 | UgpE | ABC-type sugar transport system, permease component |
| | Cphy2268 | 2796278...2797195 | UgpA | ABC-type sugar transport systems, permease components |
| | Cphy2269 | 2797161...2799770 | — | — |
| | Cphy2270 | | | |
| | Cphy2271 | | | |
| | Cphy2272 | | | binding-protein-dependent transport systems inner membrane component |
| | Cphy2273 | | | binding-protein-dependent transport systems inner membrane component |
| | Cphy2274 | | | extracellular solute-binding protein family 1 |
| | Cphy2275 | | | hypothetical protein |
| | Cphy2276 | | | Mannan endo-1,4-beta-mannosidase |
| 16 | Cphy2569 | 3136132...3137703 | UgpB | ABC-type sugar transport system, periplasmic component |
| | Cphy2570 | 3137758...3138693 | UgpE | ABC-type sugar transport system, permease component |
| | Cphy2571 | 3138707...3139672 | LplB | ABC-type polysaccharide transport system, permease component |
| 17 | Cphy2654 | 3239628...3241388 | UgpB | ABC-type sugar transport system, periplasmic component |
| | Cphy2655 | 3241527...3242447 | UgpE | ABC-type sugar transport system, permease component |
| | Cphy2656 | 3242462...3243409 | LplB | ABC-type polysaccharide transport system, permease component |
| 18 | Cphy2807 | 3420322...3421581 | COG1216 | Predicted glycosyltransferases |
| | Cphy2808 | 3421710...3422930 | — | — |
| | Cphy2809 | 3423037...3429723 | Smc | Chromosome segregation ATPases |
| | Cphy2810 | 3429863...3430933 | WcaA | Glycosyltransferases involved in cell wall biogenesis |
| | Cphy2811 | 3430994...3433558 | RfaG | Glycosyltransferase |
| | Cphy2812 | 3433803...3434108 | — | — |
| | Cphy2813 | 3434217...3435191 | RfaG | Glycosyltransferase |
| | Cphy2814 | 3435346...3436719 | COG1216 | Predicted glycosyltransferases |
| | Cphy2815 | 3437022...3437582 | COG1633 | Uncharacterized conserved protein |
| | Cphy2816 | 3437827...3438198 | — | — |
| | Cphy2817 | 3438599...3440215 | — | — |
| | Cphy2818 | 3440301...3440876 | AmiC | N-acetylmuramoyl-L-alanine amidase |
| 19 | Cphy3009 | 3672467...3674620 | BglX | Beta-glucosidase-related glycosidases |
| | Cphy3010 | 3674634...3675599 | XynA | Beta-1,4-xylanase |
| 20 | Cphy3419 | 4198367...4199833 | XylB | Sugar (pentulose and hexulose) kinases |
| | Cphy3420 | 4200152...4201297 | NagC | Transcriptional regulator/sugar kinase |
| 21 | Cphy3854 | 4724145...4726538 | COG3459 | Cellobiose phosphorylase |
| | Cphy3855 | 4726828...4728252 | ManB | Phosphomannomutase |
| | Cphy3857 | 4730021...4731766 | LytS | Putative regulator of cell autolysis |
| 22 | Cphy2008 | | | multi-sensor signal transduction histidine kinase |
| | Cphy2009 | | | periplasmic binding protein/LacI transcriptional regulator |
| | Cphy2010 | | | ABC transporter related |
| | Cphy2011 | | | Monosaccharide-transporting ATPase |
| | Cphy2012 | | | periplasmic binding protein/LacI transcriptional regulator |

Enzymes Involved in Xylose Assimilation

Some embodiments described herein relate to polynucleotides, polynucleotide cassettes, expression cassettes, expression vectors, and microorganisms comprising nucleic acids identified in *C. phytofermentans* that encode genes involved in xylose assimilation. Other embodiments relate to methods for producing fuel utilizing the polynucleotides, polynucleotide cassettes, expression cassettes, expression vectors, and microorganisms including nucleic acids identified in *C. phytofermentans* that encode genes involved in xylose assimilation.

Figure 13:
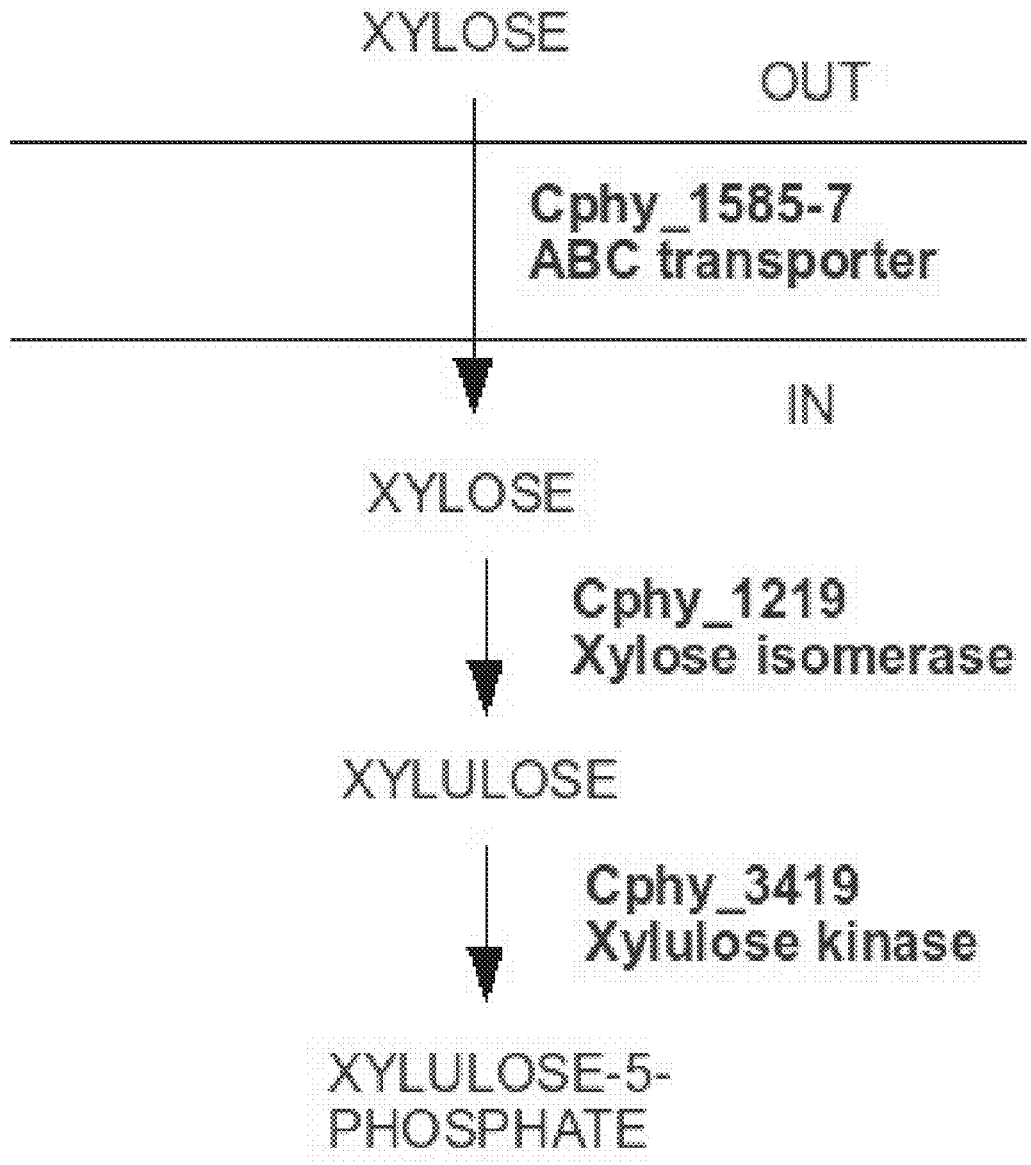
FIG. 13 is a depiction of xylose uptake and metabolism in C. phytofermentans.

As used herein, genes involved in xylose assimilation can include, for example, genes encoding hydrolases for the hydrolysis of polymers to xylose, ABC-transporters for the transportation of xylose into the cell, transcription regulators for the regulation of these genes encoding hydrolases and/or ABC-transporters, and enzymes related to the fermentation of pentose sugars, such as xylose, to alcohols. Genes identified as upregulated when *C. phytofermentans* was grown on xylose include Cphy3419, Cphy1219, and Cphy1585, Cphy1586, and Cphy1587 (see FIG. 13).

While many species of Clostridia can degrade hemicellulose, most species are unable to ferment the pentose sugars that result from such hydrolysis. Remarkably, *C. phytofermentans* is able to hydrolyze hemicellulose to pentose sugars and ferment pentose sugars to alcohols. *C. phytofermentans* may transport pentoses into the cell as oligosaccharides or as monosaccharides. The *C. phytofermentans* genome contains genes encoding enzymes for xylose assimilation including enzymes in the non-oxidative pentose phosphate pathway which is related to the conversion of pentoses into hexoses. Consistent with the ability to ferment pentoses, expression data with cells grown on xylan has shown that key enzymes in the pentose phosphate pathway, namely, transaldolase (EC 2.2.1.1, Cphy0013) and transketolase (EC 2.2.1.1, Cphy0014), are among the most abundant transcripts. Glyceraldehyde-3-phosphate dehydrogenase (EC 1.2.1.12, Cphy2879), which connects the pentose phosphate pathway and priming reactions of glycolysis to energy harvesting steps of glycolysis, is strongly induced on xylan, cellulose, cellobiose, and glucose. Other genes upregulated during growth on xylan include Cphy2105, Cphy2106, Cphy2108, Cphy1510, Cphy3158, Cphy3009, Cphy3010, Cphy3419, Cphy1219, Cphy2632, Cphy3206, Cphy3207, Cphy3208, Cphy3209, Cphy3210, Cphy3211, Cphy3212, Cphy1448, Cphy1449, Cphy1450, Cphy1451, Cphy1132, Cphy1133, Cphy1134, Cphy1528, Cphy1529, Cphy1530, Cphy1531, and Cphy1532.

Fermentation of hexoses and pentoses terminates with the reduction of acetyl-coA to ethanol catalyzed by enzymes including NAD(P)-dependent acetaldehyde dehydrogenase (Ald) and NAD-dependent alcohol dehydrogenase (Adh). The *C. phytofermentans* genome contains putative genes encoding at least 7 Ald (Domain PutA), and at least 6 Adh, for example, the putative protein encoded at Cphy3925 which contains Ald and Adh domains. 4 Ald and 3 Adh are encoded by genes in three clusters: Cphy1173-1183; Cphy1411-1430; and Cphy2634-2650.

Enzymes Involved in Propanol Production, the Metabolism of Ethanolamine and/or Propanediol Some embodiments described herein relate to polynucleotides, polynucleotide cassettes, expression cassettes, expression vectors, and microorganisms comprising nucleic acids identified in *C. phytofermentans* that encode genes involved in propanol production, the metabolism of ethanolamine and/or propanediol. Some embodiments relate to methods for producing fuel utilizing the polynucleotides, polynucleotide cassettes, expression cassettes, expression vectors, and microorganisms including nucleic acids identified in *C. phytofermentans* that encode genes involved in propanol production, the metabolism of ethanolamine and/or propanediol.

*C. phytofermentans* contains proteinaceous microcompartments ("PMC") that are not found in other bacteria of similar biotechnological interest, such as *C. cellulolyticum*, *C. thermocellum*, *C. acetobutylicum*, and *C. beijinrincki*. These microcompartments have been observed by electron microscopy. Particular enzymes involved in the conversion of carbohydrates to alcohols are localized to these microcompartments, suggesting the compartmentalization of particular pathways and greater metabolic efficiency (Conrado, R. J., Mansell, T. J., Varner, J. D. & DeLisa, M. P. Stochastic reaction-diffusion simulation of enzyme compartmentalization reveals improved catalytic efficiency for a synthetic metabolic pathway. *Metab. Eng.* 9, 355-363 (2007)).

Three genetic loci in *C. phytofermentans* encode proteins localized to proteinaceous compartments. These proteinaceous compartments are similar to the proteinaceous compartments involved in carbon dioxide fixation, and in ethanolamine and propanediol utilization found in other organisms. Each locus includes enzymes for conversion of five-carbon sugars and alcohol dehydrogenases to primary alcohols.

Of the 7 Ald and 6 Adh identified in *C. phytofermentans*, 4 Ald and 3 Adh, are localized to the proteinaceous microcompartments. The Adh localized to the proteinaceous microcompartments show sequence identity to Fe-Adh or Zn-Adh, and are encoded by genes in three clusters: Cphy1173-1183; Cphy1411-1430; and Cphy2634-2650.

More enzymes localized to the proteinaceous microcompartments may be related to the fucose to propanol pathway, as well as the metabolism of ethanolamine and propanediol. For example, the Cphy2634-2650 cluster contains orthologs of genes involved in ethanolamine metabolism in *Salmonella typhimurium*, and the Cphy1411-1430 cluster contains genes encoding products that may be functionally related to the propanediol utilization operon in *Salmonella typhimurium*.

Figure 14:
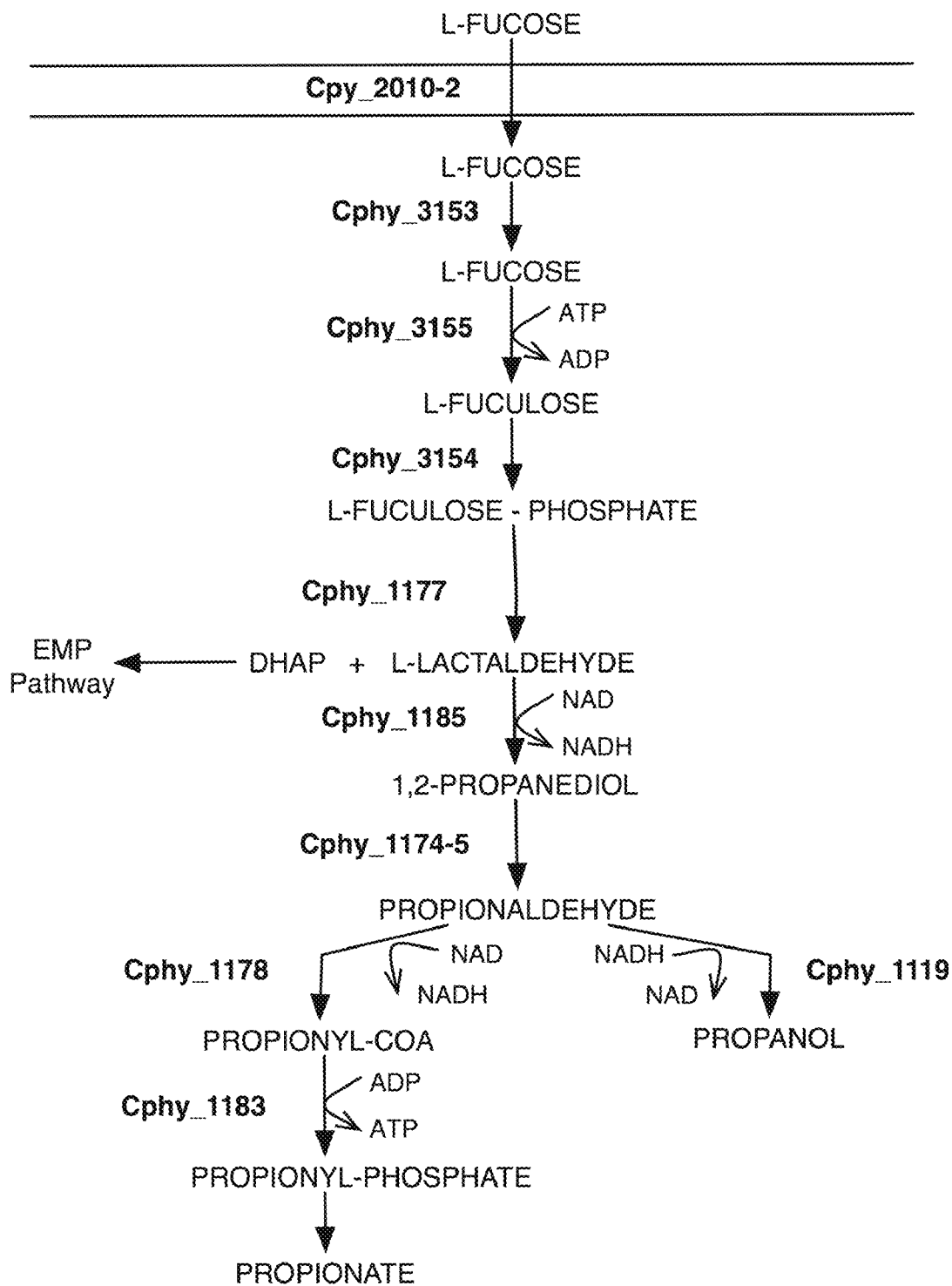
FIG. 14 is a depiction of fucose uptake and metabolism in C. phytofermentans.
Figure 15:
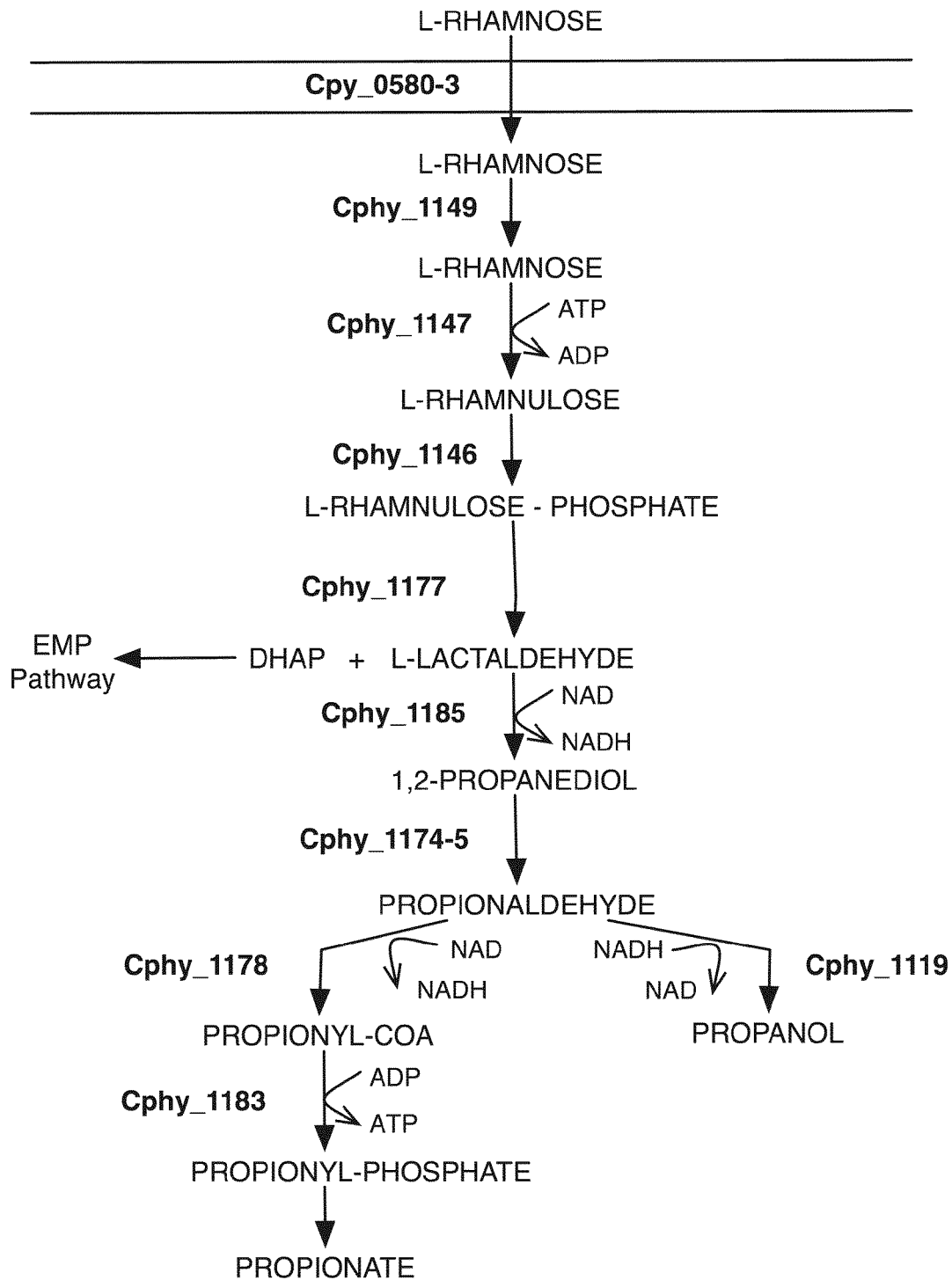
FIG. 15 is a depiction of rhamnose uptake and metabolism in C. phytofermentans.

In addition, the Cphy1173-1187 cluster contains genes homologous to a microcompartment found in *Roseburia inulinovorans* (Scott, K. P., Martin, J. C., Campbell, G., Mayer, C. D. & Flint, H. J. Whole-genome transcription profiling reveals genes up-regulated by growth on fucose in the human gut bacterium *Roseburia inulinivorans*. *J. Bacteriol.* 188, 4340-4349 (2006)) and genes encoding putative enzymes involved in fucose and rhamnose utilization (see FIGS. 14 and 15). Additional genes identified as upregulated during growth on fucose or otherwise predicted as being involved in utilization of fucose include Cphy3153, Cphy3154, Cphy3155, Cphy2010, Cphy2011, and Cphy2012 (FIG. 14). Additional genes identified as upregulated during growth on rhamnose or otherwise predicted as being involved in utilization of rhamnose include Cphy0578, Cphy0579, Cphy0580, Cphy0581, Cphy0582, Cphy0583, Cphy0584, Cphy1146, Cphy1147, Cphy1148, Cphy1149 (FIG. 15).

Hydrogen Production.

Some embodiments described herein relate to polynucleotides, polynucleotide cassettes, expression cassettes, expression vectors, and microorganisms comprising nucleic acids identified in *C. phytofermentans* that encode genes involved in hydrogen production. Other embodiments relate to methods for producing fuel utilizing the polynucleotides, polynucleotide cassettes, expression cassettes, expression vectors, and microorganisms including nucleic acids identified in *C. phytofermentans* as encoding genes involved in hydrogen production.

Hydrogen can be produced from the fermentation of a variety of sugars. In some embodiments, polynucleotides can comprise nucleic acids encoding ferredoxin hydrogenases identified in *C. phytofermentans*. Examples of genes encoding ferredoxin hydrogenases identified in *C. phytofermentans* include Cphy0087, Cphy0090, Cphy0092, Cphy2056, Cphy3805, Cphy3798.

Multimodular Polysaccharide Lyase

Some embodiments described herein relate to polynucleotides, polynucleotide cassettes, expression cassettes, expression vectors, and microorganisms comprising nucleic acids identified in *C. phytofermentans* that encode enzymes/protein domains involved in the hydrolysis of pectin. Some embodiments relate to methods for producing fuel utilizing the polynucleotides, polynucleotide cassettes, expression cassettes, expression vectors, and microorganisms including nucleic acids identified in *C. phytofermentans* as encoding enzymes/protein domains involved in hydrolysis of pectin. Examples of genes encoding enzymes/protein domains involved in the hydrolysis of pectin can include genes at the locus Cphy1612. The Cphy1612 locus encodes predicted PL1 and PL9 domains. PL1 includes a pectate lyase (EC 4.2.2.2); exo-pectate lyase (EC 4.2.2.9); and pectin lyase (EC 4.2.2.10)

domain. PL9 includes a pectate lyase (EC 4.2.2.2) and exopolygalacturonate lyase (EC 4.2.2.9) domain.

Multimodular Xylanase and Esterase

Some embodiments described herein relate to polynucleotides, polynucleotide cassettes, expression cassettes, expression vectors, and microorganisms comprising nucleic acids identified in *C. phytofermentans* that encode enzymes/protein domains including xylanase and esterase activities. Other embodiments relate to methods for producing fuel utilizing the polynucleotides, polynucleotide cassettes, expression cassettes, expression vectors, and microorganisms that include nucleic acids identified in *C. phytofermentans* as encoding enzymes/protein domains including xylanase and esterase activities. Examples of genes encoding enzymes/protein domains including xylanase and esterase activities, can include genes at the Cphy3862 locus. The Cphy3862 locus includes three predicted domains, namely, two GH10 domains and a CE15 domain, having the following activities: GH10 with xylanase (EC 3.2.1.8) activity; GH10 with endo-1,3-xylanase (EC 3.2.1.32) activity, and CE15, with glucuronyl esterase (EC 3.1.1.-) and 4-O-methyl-glucuronyl esterase (EC 3.1.1.-) activities.

Laminarin Utilization

Figure 16:
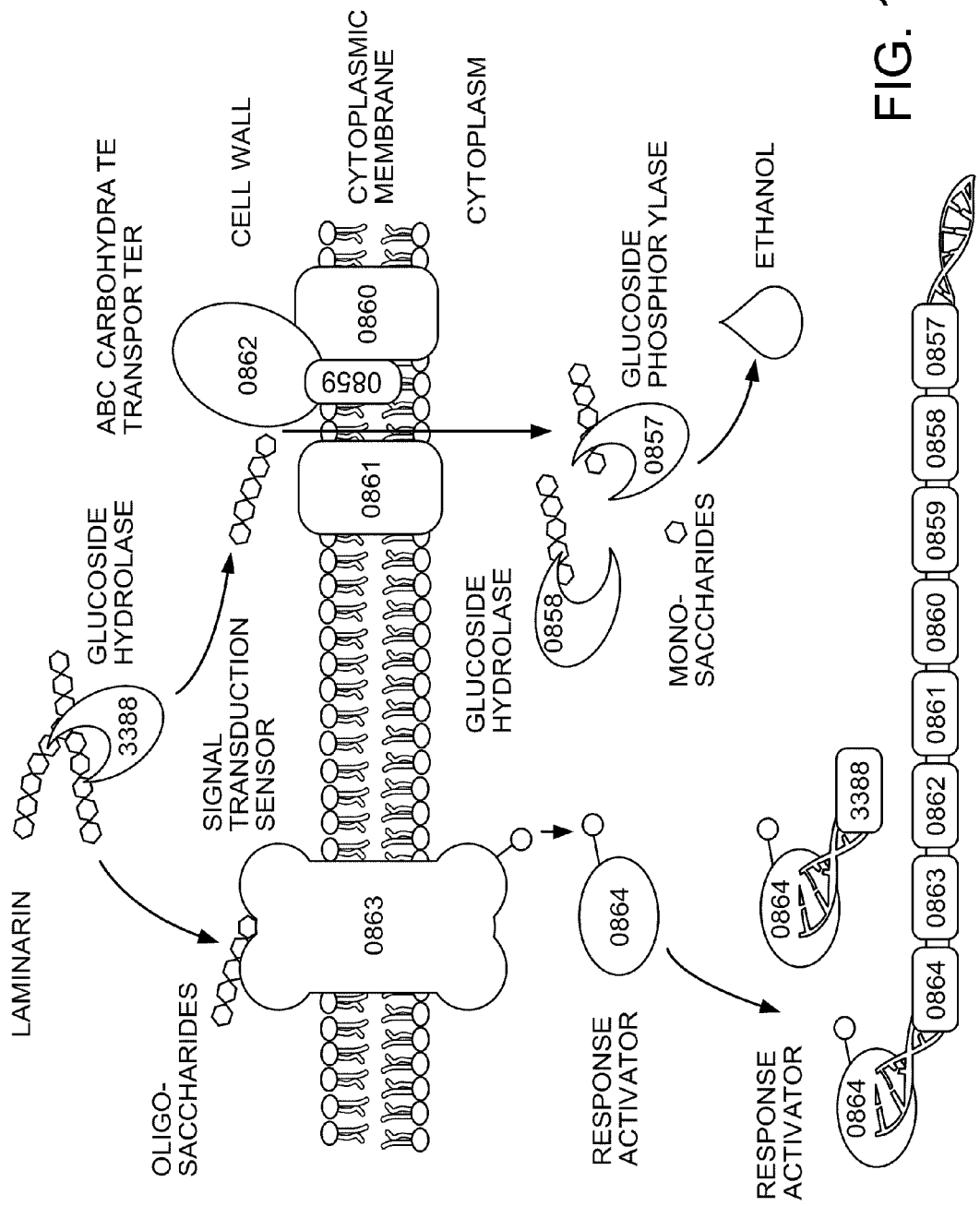
FIG. 16 is a depiction of laminarin regulation, uptake, and metabolism in C. phytofermentans.

Some embodiments described herein relate to polynucleotides, polynucleotide cassettes, expression cassettes, expression vectors, and microorganisms comprising nucleic acids identified in *C. phytofermentans* encoding enzymes/protein domains involved in laminin utilization. Some embodiments relate to methods for producing fuel utilizing the polynucleotides, polynucleotide cassettes, expression cassettes, expression vectors, and microorganisms including nucleic acids identified in *C. phytofermentans* encoding enzymes/protein domains involved in laminin utilization. Laminarin is a storage glucan (a polysaccharide of glucose) found in brown algae. Examples of genes identified as upregulated during growth on laminarin include Cphy0857, Cphy0858, Cphy0859, Cphy0860, Cphy0861, Cphy0862, Cphy0863, Cphy0864, Cphy0865, and Cphy3388 (see FIG. 16).

Cellobiose Utilization

Figure 17:
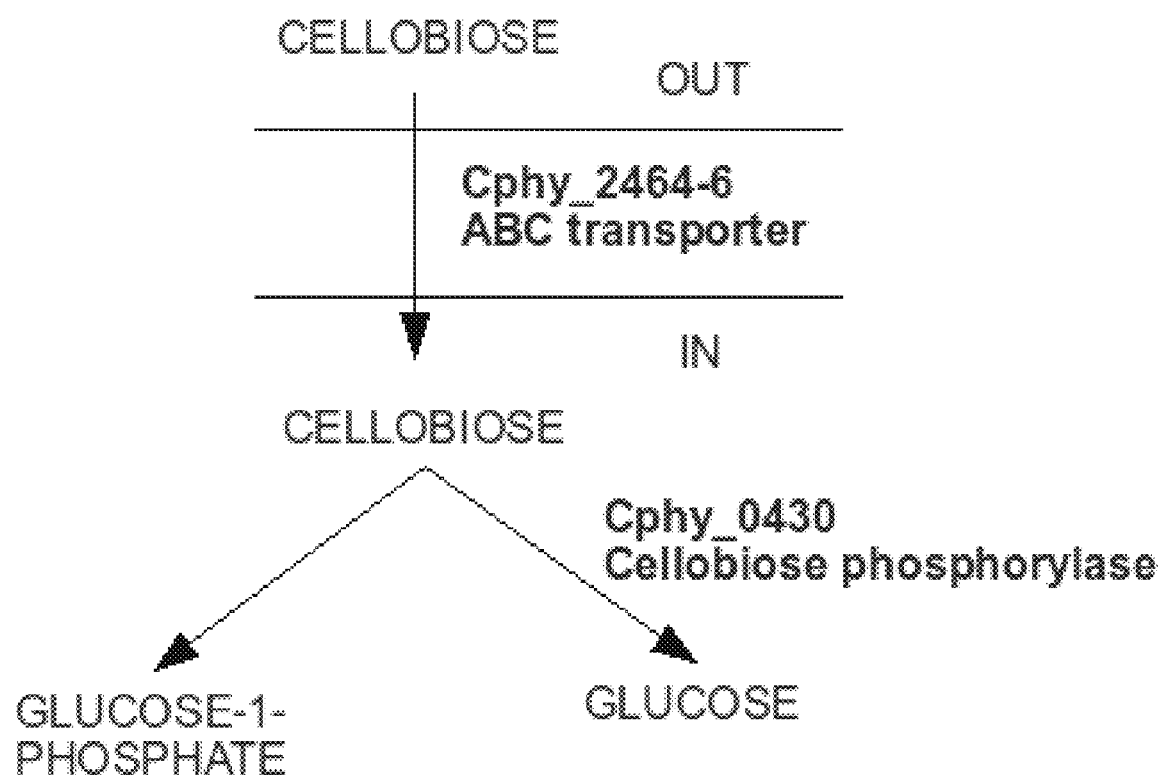
FIG. 17 is a depiction of cellobiose uptake and metabolism in C. phytofermentans.

Some embodiments described herein relate to polynucleotides, polynucleotide cassettes, expression cassettes, expression vectors, and microorganisms comprising nucleic acids identified in *C. phytofermentans* encoding enzymes/protein domains involved in cellobiose utilization. Other embodiments relate to methods for producing fuel utilizing the polynucleotides, polynucleotide cassettes, expression cassettes, expression vectors, and microorganisms including nucleic acids identified in *C. phytofermentans* encoding enzymes/protein domains involved in cellobiose utilization. Cellobiose is a disaccharide derived from the condensation of two glucose molecules linked in a β(1→4) bond. Examples of genes identified as upregulated during growth on cellobiose include Cphy0430, Cphy2464, Cphy2465, Cphy2466, and Cphy2467 (see FIG. 17).

Cellulose Utilization

Some embodiments described herein relate to polynucleotides, polynucleotide cassettes, expression cassettes, expression vectors, and microorganisms comprising nucleic acids identified in *C. phytofermentans* encoding enzymes/protein domains involved in cellulose utilization. Some embodiments relate to methods for producing fuel utilizing the polynucleotides, polynucleotide cassettes, expression cassettes, expression vectors, and microorganisms including nucleic acids identified in *C. phytofermentans* encoding enzymes/protein domains involved in cellulose utilization. Examples of genes identified as upregulated during growth on cellulose or otherwise predicted as being involved in utilization of cellulose include Cphy3367, Cphy3368, Cphy1163, Cphy3202, Cphy3160, Cphy0430, Cphy3854, Cphy3855, Cphy3857, Cphy3858, Cphy3859, Cphy3860, Cphy3861, Cphy3862, Cphy2569, Cphy2570, Cphy2571, Cphy2464, Cphy2465, Cphy2466, Cphy2467, Cphy1528, Cphy1529, Cphy1530, Cphy1531, and Cphy1532.

Pectin Utilization

Some embodiments described herein relate to polynucleotides, polynucleotide cassettes, expression cassettes, expression vectors, and microorganisms comprising nucleic acids identified in *C. phytofermentans* encoding enzymes/protein domains involved in pectin utilization. Other embodiments relate to methods for producing fuel utilizing the polynucleotides, polynucleotide cassettes, expression cassettes, expression vectors, and microorganisms including nucleic acids identified in *C. phytofermentans* encoding enzymes/protein domains involved in pectin utilization. Examples of genes identified as upregulated during growth on pectin include Cphy3585, Cphy3586, Cphy3587, Cphy3588, Cphy3589, Cphy3590, Cphy2262, Cphy2263, Cphy2264, Cphy2265, Cphy2266, Cphy2267, Cphy2268, Cphy2269, Cphy2272, Cphy2273, Cphy2274, Cphy2275, Cphy2276, Cphy2464, Cphy2465, Cphy2466, Cphy2467, Cphy1714, Cphy1715, Cphy1716, Cphy1717, Cphy1718, Cphy1719, Cphy1720, Cphy3153, Cphy3154, Cphy3155, Cphy2010, Cphy2011, Cphy1174, Cphy1175, Cphy1176, Cphy1177, Cphy1178, Cphy1179 Cphy1180, Cphy1181, Cphy1182, Cphy1183, Cphy1929, Cphy1612, Cphy0218, Cphy0219, Cphy0220, Cphy3160, and Cphy2919.

Genes upregulated during growth on pectin and predicted to be involved in the breakdown and transport of the arabinogalactan side chain of rhamnogalacturonan-I include Cphy3585, Cphy3586, Cphy3587, Cphy3588, Cphy3589, and Cphy3590. Genes upregulated during growth on pectin and predicted to be involved in the breakdown and transport of rhamnogalacturonan-I or rhamnogalacturonan-II sidechains include Cphy2262, Cphy2263, Cphy2264, Cphy2265, Cphy2266, Cphy2267, Cphy2268, Cphy2269, Cphy2272, Cphy2273, Cphy2274, Cphy2275, Cphy2276, Cphy1714, Cphy1715, Cphy1716, Cphy1717, Cphy1718, Cphy1719, and Cphy1720. Genes upregulated during growth on pectin and predicted to be involved in sugar transport include Cphy2464, Cphy2465, Cphy2466, and Cphy2467. Genes predicted to be involved in the breakdown and transport of polygalacturonic acid include Cphy0288, Cphy0289, Cphy0290, Cphy0291, Cphy0292, and Cphy0293. Genes predicted to be involved in rhamnogalacturonan lysis and transport include Cphy0339, Cphy0340, Cphy0341, Cphy0342, Cphy0343. Genes predicted to be involved in rhamnose transport and breakdown include Cphy0578, Cphy0579, Cphy0580, Cphy0581, Cphy0582, Cphy0583, Cphy0584, Cphy1146, Cphy1147, Cphy1148, and Cphy1149. Genes upregulated during growth on pectin and/or predicted to be involved in fucose transport and breakdown include Cphy3153, Cphy3154, Cphy3155, Cphy2010, Cphy2011, and Cphy2012. Genes upregulated during growth on pectin and/or predicted to be involved in fucose and rhamnose metabolism include Cphy1174, Cphy1175, Cphy1176, Cphy1177, Cphy1178, Cphy1179, Cphy1180, Cphy1181, Cphy1182, Cphy1183, Cphy1184, Cphy1185, Cphy1186, and Cphy1187.

Genes upregulated during growth on pectin and/or predicted to be involved in polygalacturonic acid utilization include Cphy2919, Cphy0288, Cphy0289, Cphy0290, Cphy0291, Cphy0292, Cphy0293, Cphy3308, Cphy3309, Cphy3310, Cphy3311, Cphy3312, Cphy3313, Cphy3314, Cphy3315, Cphy3316, Cphy3317, Cphy1118, Cphy1119, Cphy1120, Cphy1121, Cphy1879, Cphy1880, Cphy1881, Cphy1882, Cphy1883, Cphy2736, Cphy2737, Cphy2738, Cphy2739, Cphy2740, Cphy2741, Cphy2742, and Cphy2743.

Identifying Nucleic Acid Sequences in C. Phytofermentans

Some embodiments described herein relate to methods for identifying genes in C. phytofermentans. Such methods can include identifying nucleic acid sequences that contain coding sequences, non-coding sequences, regulatory sequences, intergenic sequences, operons or clusters of genes. In some embodiments, methods for identifying genes in C. phytofermentans can include genomic and/or microarray analyses.

In some embodiments, a gene in C. phytofermentans can be identified by the gene's similarity to another sequence. Similarity can be determined between polynucleotide sequences or polypeptide sequences. In some embodiments, another sequence can be a sequence present in another organism. Examples of other organisms can include an organism of a different species of Clostridia, such as C. beijerinckii or C. acetobutylicum; or an organism of a different genus, such as Bacillus subtilis.

In some embodiments, similarity can be measured as a percent identity. The percent sequence identity can be a relationship between two or more polypeptide sequences or two or more polynucleotide sequences, as determined by comparing the sequences. In further embodiments, identity of sequences can be the degree of sequence relatedness between polypeptide or polynucleotide sequences, as the case may be, as determined by the match between strings of such sequences. Typically, sequence identity and sequence similarity can be readily calculated by known methods, including but not limited to those described in: Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, NY (1991). Methods to determine sequence identity can be designed to give the best match between the sequences tested. Some methods to determine sequence identity and sequence similarity are codified in publicly available computer programs. Sequence alignments and percent identity calculations can be performed using the Megalign program of the LASERGENE bioinformatics computing suite (DNASTAR Inc., Madison, Wis.). Multiple alignment of the sequences can be performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

In other embodiments, a gene in C. phytofermentans can be identified by predicting the presence of a gene in a nucleic acid sequence and/or putative translated polypeptide sequence using algorithms well known in the art. For example, computer algorithms in programs can be used, such as GeneMark™ (Besemer, J., and M. Borodovsky. 2005. GeneMark: web software for gene finding in prokaryotes, eukaryotes and viruses. Nucleic Acids Res 33:W451-4) and Glimmer (Delcher, A. L., K. A. Bratke, E. C. Powers, and S. L. Salzberg. 2007. Identifying bacterial genes and endosymbiont DNA with Glimmer. Bioinformatics 23:673-9).

In some embodiments, nucleotide or amino acid sequences can be analyzed using a computer algorithm or software program. In related embodiments, sequence analysis software can be commercially available or independently developed. Examples of sequence analysis software includes the GCG suite of programs (Wisconsin Package Version 9.0, Genetics Computer Group (GCG), Madison, Wis.), BLASTP, BLASTN, BLASTX (Altschul et al., J. Mol. Biol. 215:403-410 (1990), and DNASTAR (DNASTAR, Inc. 1228 S. Park St. Madison, Wis. 53715 USA), and the FASTA program incorporating the Smith-Waterman algorithm (W. R. Pearson, Comput. Methods Genome Res., [Proc. Int. Symp.] (1994), Meeting Date 1992, 111-20. Editor(s): Suhai, Sandor. Publisher: Plenum, New York, N.Y.). Typically, the default values of a program can be used, for example, a set of values or parameters originally load with the software when first initialized.

In other embodiments databases of conserved protein domains and protein families can be used to identify a gene in C. phytofermentans. For example, the Conserved Domain Database (CDD) of the National Center for Biotechnology Information (NCBI) comprises several databases including the curated NCBI Conserved Domains, SMART (smart.embl-heidelberg.de/SMART), PFAM (available on the World Wide Web at sanger.ac.uk/Software/Pfam/PFAM), and COGS (Phylogenetic classification of proteins encoded in complete genomes).

In some embodiments, genes can be identified and metabolic pathways of putative proteins encoded by the genes can be predicted. In such embodiments, metabolic pathways databases can be used. For example, the Kyoto Encyclopedia of Genes and Genomes (KEGG), where the KEGG Automatic Annotation Server (available on the World Wide Web at genome.jp/kegg/kaas/) can provide functional annotation of identified genes using BLAST comparisons against the KEGG GENES database.

Isolating Nucleic Acid Sequences from C. phytofermentans

Nucleic acid sequences can be cloned from the C. phytofermentans genome using techniques well known in the art. For example, recombinant DNA and molecular cloning techniques which can be utilized are described by Sambrook, J., Fritsch, E. F. and Maniatis, T., Molecular Cloning: A Laboratory Manual, Second Edition, Cold Spring Harbor Laboratory Press, Cold Spring Harbor, N.Y. (1989); and by Silhavy, T. J., Bennan, M. L. and Enquist, L. W., Experiments with Gene Fusions, Cold Spring Harbor Laboratory Cold Press Spring Harbor, N.Y. (1984); and by Ausubel, F. M. et al., Current Protocols in Molecular Biology, published by Greene Publishing Assoc. and Wiley-Interscience (1987). Additionally, methods to isolate homologous or orthologous genes using sequence-dependent protocols are well known in the art. Examples of sequence-dependent protocols include, but are not limited to, methods of nucleic acid hybridization, and methods of DNA and RNA amplification as exemplified by various uses of nucleic acid amplification technologies, such as, polymerase chain reaction (PCR; Mullis et al., U.S. Pat. No. 4,683,202), ligase chain reaction (LCR; Tabor, S. et al., Proc. Acad. Sci. USA 82, 1074, (1985)) or strand displacement amplification (SDA; Walker, et al., Proc. Natl. Acad. Sci. U.S.A., 89, 392, (1992)).

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotide as specific hybridization probes in the Diagnosis of Genetic Disorders", in Human Genetic Diseases: A Practical Approach, K. E. Davis Ed., (1986) pp. 33-50 IRL Press, Hemdon, Va.; Rychlik, W. (1993) In White, B. A. (ed.), Methods in Molecular Biology, Vol. 15, pages 31-39, PCR Protocols: Current Methods and Applications. Humania Press, Inc., Totowa, N.J.).

Generally, two short segments of an identified sequence can be used in PCR protocols to amplify longer nucleic acid fragments encoding homologous genes from DNA or RNA. The PCR can be performed on a library of cloned nucleic acid fragments wherein the sequence of one primer is derived from the identified nucleic acid sequence, and the sequence of the other primer is derived from the characteristic polyadenylic acid tracts 3' of the mRNA precursor encoding microbial genes. Alternatively, the second primer sequence may be based upon sequences derived from a cloning vector. For example, the RACE protocol (Frohman et al., PNAS USA 85:8998 (1988)) provides a means to generate cDNAs using PCR to amplify copies of the region between a single point in the transcript and the 3' or 5' end. Primers oriented in the 3' and 5' directions can be designed from the identified sequence. Using commercially available 3' RACE or 5' RACE systems (BRL), specific 3' or 5' cDNA fragments can be isolated (Ohara et al., PNAS USA 86:5673 (1989); Loh et al., Science 243:217 (1989)).

In some embodiments, identified nucleic acid sequences can be isolated by screening a *C. phytofermentans* DNA library using a portion of the identified nucleic acid as a DNA hybridization probe. Examples of probes can include DNA probes labeled by methods such as, random primer DNA labeling, nick translation, or end-labeling techniques, and RNA probes produced by methods such as, in vitro transcription systems. Additionally, specific oligonucleotides can be designed and used to amplify a part of or full-length of the instant sequences. The resulting amplification products can be labeled directly during amplification reactions or labeled after amplification reactions, and used as probes to isolate full length DNA fragments under conditions of appropriate stringency.

In some embodiments, isolated nucleic acids are cloned into vectors. Typically, vectors have the ability to replicate in a host microorganism. Numerous vectors are known, for example, bacteriophage, plasmids, viruses, or hybrids thereof. Vectors can be operable as cloning vectors or expression vectors in the selected host cell. Typically, a vector comprises an isolated nucleic acid, a selectable marker, and sequences allowing autonomous replication or chromosomal integration. Further embodiments can comprise a promoter sequence driving expression of an isolated nucleic acid, an enhancer, or a termination sequence. In other embodiments, a vector can comprise sequences that allow excision of sequences subsequent to integration into chromosomal DNA of vector sequences. Examples include loxP sequences or FRT sequences, these sequences are responsive to CRE recombinase and FLP recombinase, respectively.

Polynucleotides, Polynucleotide Cassettes Expression Cassettes and Expression Vectors Some embodiments described herein relate to polynucleotides, polynucleotide cassettes, expression cassettes, and expression vectors useful for the production of a fuel or other product in a recombinant microorganism.

Polynucleotide cassettes can comprise at least one polynucleotide of interest. In some embodiments, a polynucleotide cassette can comprise more than one polynucleotide of interest. For example, a polynucleotide cassette can comprise two or more, three or more, or any number of genes and/or polynucleotides of interest described herein.

In some embodiments, a polynucleotide of interest can include one or more nucleic acids described herein identified in *C. phytofermentans*. In some embodiments, the polynucleotide of interest can have at least 50%, 55%, 60%, 65%, 70%, 80%, 85%, 90%, 95%, 96%, 97%, 98%, 99%, and 100% identity with one or more genes identified in *C. phytofermentans*. In other embodiments, the polynucleotide of interest can encode one or more proteins comprising conservative substitutions to the wild type protein. In further embodiments, the polynucleotide of interest can encode one or more proteins comprising substitutions that alter the efficiency of the protein for fuel production. For example, proteins encoding enzymes may be made more efficient catalyzing reactions.

As used herein, an expression cassette can be a polynucleotide(s) of interest operably linked to a regulatory sequence, such as a promoter. Promoters suitable for the present invention include any promoter for expression of the polynucleotide of interest. In some embodiments, the promoter can be the promoter sequence identified in *C. phytofermentans*. In some embodiments, the promoter can be a promoter sequences identified in a host organism. In some embodiments, the promoter can be an inducible promoter, such as, for example, a light-inducible promoter or a temperature sensitive promoter. In other embodiments, the promoter can be a constitutive promoter. In some embodiments, a promoter can be selected based upon the desired expression level for the polynucleotide(s) of interest in the host microorganism. In some embodiments, the promoter can be positioned about the same distance from the heterologous transcription start site as it is from the transcription start site in its natural setting. As is known in the art, however, some variation in this distance can be accommodated without loss of promoter function. In other embodiments, an expression cassette can further comprise regulatory sequences such as enhancers and/or termination sequences.

Promoter elements can be selected and mobilized in a vector (e.g., pIMPCphy). For example, a transcription regulatory sequence is operably linked to gene(s) of interest (e.g., in an expression construct). The promoter can be any array of DNA sequences that interact specifically with cellular transcription factors to regulate transcription of the downstream gene. The selection of a particular promoter depends on what cell type is to be used to express the protein of interest. Generally, a useful transcription regulatory sequence is one from the host microorganism. In various embodiments, constitutive or inducible promoters are selected for use in a host cell. Depending on the host cell, there are potentially hundreds of constitutive and inducible promoters that are known and that can be engineered to function in the host cell.

A promoter can be any array of DNA sequences that interact specifically with cellular transcription factors to regulate transcription of the downstream gene. The selection of a particular promoter depends on what cell type is to be used to express the protein of interest. Transcription regulatory sequences can be those from the host microorganism. In various embodiments, constitutive or inducible promoters are selected for use in a host cell. Depending on the host cell, there are potentially hundreds of constitutive and inducible promoters that are known and that can be engineered to function in the host cell.

In some instances, promoters widely utilized in recombinant technology, for example *Escherichia coli* lac and trp operons, the tac promoter, the bacteriophage pL promoter, bacteriophage T7 and SP6 promoters, beta-actin promoter, insulin promoter, baculoviral polyhedrin and p10 promoter, can be utilized.

In other instances, a constitutive promoter can be utilized. Non-limiting examples of constitutive promoters include the int promoter of bacteriophage lambda, the bla promoter of the beta-lactamase gene sequence of pBR322, hydA or thlA in *Clostridium, Streptomyces coelicolor* hrdB, or whiE, the CAT promoter of the chloramphenicol acetyl transferase gene sequence of pPR325, Staphylococcal constitutive promoter blaZ and the like.

A promoter useful for the present invention can also be an inducible promoter that regulates the expression of downstream gene in a controlled manner, such as under a specific condition of the cell culture. Examples of inducible prokaryotic promoters include the major right and left promoters of bacteriophage, the trp, recA, lacZ, AraC, and gal promoters of *E. coli*, the alpha-amylase (Ulmanen Ett at., J. Bacteriol. 162:176-182, 1985) and the sigma-D-specific promoters of *Bacillus subtilis* (Gilman et al., Gene sequence 32:11-20 (1984)), the promoters of the bacteriophages of *Bacillus* (Gryczan, In: The Molecular Biology of the Bacilli, Academic Press, Inc., NY (1982)), *Streptomyces* promoters (Ward et al., Mol. Gen. Genet. 203:468-478, 1986), and the like. Exemplary prokaryotic promoters are reviewed by Glick (J. Ind. Microtiot. 1:277-282, 1987); Cenatiempo (Biochimie 68:505-516, 1986); and Gottesrnan (Ann. Rev. Genet. 18:415-442, 1984).

A promoter that is constitutively active under certain culture conditions, may be inactive in other conditions. For example, the promoter of the hydA gene from *Clostridium acetobutylicum*, expression is known to be regulated by the environmental pH. Furthermore, temperature regulated promoters are also known and can be utilized. Therefore, in some embodiments, depending on the desired host cell, a pH-regulated or temperature regulated promoter can be utilized with the expression constructs of the invention. Other pH regulatable promoters are known, such as P170 functioning in lactic acid bacteria, as disclosed in U.S. Patent Application No. 2002-0137140.

In general, to express the desired gene/nucleotide sequence efficiently, various promoters may be used; e.g., the original promoter of the gene, promoters of antibiotic resistance genes such as for instance the kanamycin resistant gene of Tn5, ampicillin resistant gene of pBR322, and promoters of lambda phage, and any promoters which may be functional in the host cell. For expression, other regulatory elements, such as for instance a Shine-Dalgarno (SD) sequence including natural and synthetic sequences operable in the host cell) and a transcriptional terminator (inverted repeat structure including any natural and synthetic sequence) that operable in the host cell (into which the coding sequence will be introduced to provide a recombinant cell of this invention) can be used with the above described promoters.

Examples of promoters that can be utilized with products and processes of the invention include those disclosed in the following patent documents: US 2004/0171824, U.S. Pat. No. 6,410,317, WO 2005/024019. Several promoter-operator systems, such as lac, (D. V. Goeddel et al., "Expression in *Escherichia coli* of Chemically Synthesized Genes for Human Insulin," Proc. Nat. Acad. Sci. U.S.A., 76:106-110 (1979)); trp (J. D. Windass et al. "The Construction of a Synthetic *Escherichia coli* Trp Promoter and Its Use In the Expression of a Synthetic Interferon Gene", Nucl. Acids. Res., 10:6639-57 (1982)) and λ PL operons (R. Crowl et al., "Versatile Expression Vectors for High-Level Synthesis of Cloned Gene Products in *Escherichia coli*", Gene, 38:31-38 (1985)) exist in *E. coli* and have been used for the regulation of gene expression in recombinant cells. The corresponding regulators are the lac repressor, trpR, and cI repressors, respectively.

Repressors are protein molecules that bind specifically to particular operators. For example, the lac repressor molecule binds to the operator of the lac promoter-operator system, while the cro repressor binds to the operator of the $\lambda P_R$ promoter. Other combinations of repressor and operator are known in the art. See, e.g., J. D. Watson et al., Molecular Biology Of The Gene, p. 373 (4th ed. 1987). The structure formed by the repressor and operator blocks the productive interaction of the associated promoter with RNA polymerase, thereby preventing transcription. Other molecules, termed inducers, bind to repressors, thereby preventing the repressor from binding to its operator. Thus, the suppression of protein expression by repressor molecules may be reversed by reducing the concentration of repressor or by neutralizing the repressor with an inducer.

Analogous promoter-operator systems and inducers are known in other microorganisms. In yeast, the GAL10 and GAL1 promoters are repressed by extracellular glucose, and activated by addition of galactose, an inducer. Protein GAL80 is a repressor for the system, and GAL4 is a transcriptional activator. Binding of GAL80 to galactose prevents GAL80 from binding GAL4. Then, GAL4 can bind to an upstream activation sequence (UAS) activating transcription. See Y. Oshima, "Regulatory Circuits for Gene Expression: The Metabolisms Of Galactose And Phosphate" in The Molecular Biology Of The Yeast Saccharomyces, Metabolism And Gene Expression, J. N. Strathern et al. eds. (1982).

Transcription under the control of the PHO5 promoter is repressed by extracellular inorganic phosphate, and induced to a high level when phosphate is depleted. R. A. Kramer and N. Andersen, "Isolation of Yeast Genes with mRNA Levels Controlled By Phosphate Concentration," Proc. Nat. Acad. Sci. U.S.A., 77:6451-6545 (1980). A number of regulatory genes for PHO5 expression have been identified, including some involved in phosphate regulation.

Matα2 is temperature regulated promoter system in yeast. A repressor protein, operator, and promoter sites have been identified in this system. A. Z. Sledziewski et al., "Construction Of Temperature-Regulated Yeast Promoters Using The Matα2 Repression System," Bio/Technology, 6:411-16 (1988).

Another example of a repressor system in yeast is the CUP1 promoter, which can be induced by $Cu^{2+}$ ions. The CUP1 promoter is regulated by a metallothionine protein. J. A. Gorman et al., "Regulation of The Yeast Metallothionine Gene," Gene, 48:13-22 (1986).

Similarly, to obtain desired expression of one or more cellulases, a higher copy number plasmid can utilized in a product or process of the invention. Constructs can be prepared for chromosomal integration of the desired genes. Chromosomal integration of foreign genes can offer several advantages over plasmid-based constructions, the latter having certain limitations for commercial processes. Ethanologenic genes have been integrated chromosomally in *E. coli* B; see Ohta et al. (1991) Appl. Environ. Microbiol. 57:893-9. In general, this is accomplished by purification of a DNA fragment containing (1) the desired genes upstream from an antibiotic resistance gene and (2) a fragment of homologous DNA from the target microorganism. This DNA can be ligated to form circles without replicons and used for transformation. Thus, the gene of interest can be introduced in a heterologous host such as *E. coli*, and short, random fragments can be isolated and operably linked to target genes (e.g., genes encoding cellulase enzymes) to promote homologous recombination.

Expression Vectors

Expression vectors can comprise any expression cassette described herein, and typically include all the elements required for expression of one or more polynucleotides of interest in a host cell. In some embodiments, a polynucleotide of interest is introduced into a vector to create a recombinant expression vector suitable for transformation of a host cell for the production of a fuel in a recombinant microorganism. In other embodiments, an expression cassette can be introduced into a vector to create a recombinant expression vector suitable for transformation of a host cell. In some embodiments, expression vectors comprising one more expression cassettes are provided.

Expression vectors can replicate autonomously, or they can replicate by being inserted into the genome of the host cell. In some embodiments, an expression cassette can be homologously integrated into the host cell genome. In other embodiments, the genes can be non-homologously integrated into the host cell genome. In some embodiments, the expression cassette can integrate into a desired locus via double homologous recombination.

In some embodiments, it can desirable for a vector to be usable in more than one host cell. For example, a vector can be used for cloning in *E. coli* and for expression in a *Clostridium* species. Such a vector will typically include an *E. coli* origin of replication and an origin compatible with *Clostridium* or other Gram-positive bacteria. Several *E. coli* and Gram positive plasmid replication origins are known. Additional elements of the vector can include, for example, selectable markers, e.g., kanamycin resistance or ampicillin resistance, which permit detection and/or selection of those cells transformed with the desired polynucleotide sequences. Exemplary Clostridial shuttle vectors are described in Mauchline et al. (1999) In: Clostridia: Manual of Industrial Microbiology and Biotechnology, A L Demain and J E Davies, ed. (ASM Press), pp. 475-492; and Heap et al., J. Microbiol. Methods, 78:79-85 (2009).

In some embodiments the expression vector can include one or more genes whose presence and/or expression allow for the tolerance of a host cell to economically relevant ethanol concentrations. For example, genes such as omrA, lmrA, and lmrCD may be included in the expression vector. OmrA from wine lactic acid bacteria *Oenococcus oeni* and its homolog LmrA from *Lactococcus lactis* have been shown to increase the relative resistance of tolC(−) *E. coli* by 100 to 10,000 times (Bourdineaud et al., A bacterial gene homologous to ABC transporters protect *Oenococcus oeni* from ethanol and other stress factors in wine. Int. J. Food Microbiol. 2004 Apr. 1; 92(1):1-14). Therefore, it may be beneficial to incorporate omrA, lmrA, and other homologues to increase the ethanol tolerance of a host cell.

In some embodiments, the vectors provided herein can include one or more genomic nucleic acid segments for facilitating targeted integration into the host organism genome. A genomic nucleic acid segment for targeted integration can be from about ten nucleotides to about 20,000 nucleotides long. In some embodiments, a genomic nucleic acid segment for targeted integration can be about can be from about 1,000 to about 10,000 nucleotides long. In other embodiments, a genomic nucleic acid segment for targeted integration is between about 1 kb to about 2 kb long. In some embodiments, a "contiguous" piece of nuclear genomic nucleic acid can be split into two flanking pieces when the genes of interest are cloned into the non-coding region of the contiguous DNA. This allows for integration of the intervening nucleic acid region into the bacterial chromosome by a double crossover recombination. In other embodiments, the flanking pieces can comprise segments of nuclear nucleic acid sequence which are not contiguous with one another. In some embodiments, a first flanking genomic nucleic acid segment is located between about 0 to about 10,000 base pairs away from a second flanking genomic nucleic acid segment in the nuclear genome.

In some embodiments, genomic nucleic acid segments can be introduced into a vector to generate a backbone expression vector for targeted integration of any expression cassette disclosed herein into the nuclear genome of the host organism. Any of a variety of methods known in the art for introducing nucleic acid sequences can be used. For example, nucleic acid segments can be amplified from isolated nuclear genomic nucleic acid using appropriate primers and PCR. The amplified products can then be introduced into any of a variety of suitable cloning vectors by, for example, ligation. Some useful vectors include, for example without limitation, pGEM13z, pGEMT and pGEMTEasy (Promega, Madison, Wis.); pSTBlue1 (EMD Chemicals Inc. San Diego, Calif.); and pcDNA3.1, pCR4-TOPO, pCR-TOPO-II, pCRBlunt-II-TOPO (Invitrogen, Carlsbad, Calif.). In some embodiments, at least one nucleic acid segment from a nucleus is introduced into a vector. In other embodiments, two or more nucleic acid segments from a nucleus are introduced into a vector. In some embodiments, the two nucleic acid segments can be adjacent to one another in the vector. In some embodiments, the two nucleic acid segments introduced into a vector can be separated by, for example, between about one and thirty base pairs. In some embodiments, the sequences separating the two nucleic acid segments can contain at least one restriction endonuclease recognition site.

In various embodiments, regulatory sequences can be included in the vectors of the present invention. In some embodiments, the regulatory sequences comprise nucleic acid sequences for regulating expression of genes (e.g., a gene of interest) introduced into the nuclear genome. In various embodiments, the regulatory sequences can be introduced into a backbone expression vector. For example, various regulatory sequences can be identified from the host microorganism genome. The regulatory sequences can comprise, for example, a promoter, an enhancer, an intron, an exon, a 5' UTR, a 3' UTR, or any portions thereof of any of the foregoing, of a nuclear gene. Using standard molecular biology techniques, the regulatory sequences can be introduced the desired vector. In some embodiments, the vectors comprise a cloning vector or a vector comprising nucleic acid segments for targeted integration.

In some embodiments, nucleic acid sequences for regulating expression of genes introduced into the nuclear genome can be introduced into a vector by PCR amplification of a 5' UTR, 3' UTR, a promoter and/or an enhancer, or portion thereof, one or more nuclear genes. Using suitable PCR cycling conditions, primers flanking the sequences to be amplified are used to amplify the regulatory sequences. In some embodiments, the primers can include recognition sequences for any of a variety of restriction enzymes, thereby introducing those recognition sequences into the PCR amplification products. The PCR product can be digested with the appropriate restriction enzymes and introduced into the corresponding sites of a vector.

In other embodiments, one or more genes to be expressed can be integrated into the genome of the microorganism using commercially available systems or similar methods. The applicability of these methods to Clostridia has been demonstrated, including the integration and expression of a foreign gene in a *Clostridium* cell (see, e.g., Heap et al. (2007). J. Microbiol. Methods. 70:452-464; Chen et al. (2007). Plasmid. 58:182-189).

Microorganism Hosts

Some embodiments relate to microorganisms containing any of the polynucleotides, polynucleotide cassettes, expression cassettes, or expression vectors described herein. Host cells can include, but are not limited to, eukaryotic cells, such as animal cells, insect cells, fungal cells, and yeasts, and prokaryotic cells, such as bacteria. In some embodiments, the host is *C. phytofermentans*. In some embodiments, a potential host organism can comprise a recombinant organism.

In some embodiments, the recombinant microorganism can be a cellulolytic or saccharolytic microorganism. In certain embodiments, the microorganism can be *Clostridium cellulovorans, Clostridium cellulolyticum, Clostridium thermocellum, Clostridium josui, Clostridium papyrosolvens, Clostridium cellobioparum, Clostridium hungatei, Clostridium cellulosi, Clostridium stercorarium, Clostridium termitidis, Clostridium thermocopriae, Clostridium celerecrescens, Clostridium polysaccharolyticum, Clostridium populeti, Clostridium lentocellum, Clostridium chartatabidum, Clostridium aldrichii, Clostridium herbivorans, Acetivibrio cellulolyticus, Bacteroides cellulosolvens, Caldicellulosiruptor saccharolyticum, Ruminococcus albus, Ruminococcus flavefaciens, Fibrobacter succinogenes, Eubacterium cellulosolvens, Butyrivibrio fibrisolvens, Anaerocellum thermophilum, Halocella cellulolytica, Thermoanaerobacterium thermosaccharolyticum* or *Thermoanaerobacterium saccharolyticum*.

In some embodiments, a host microorganism can be selected, for example, from the broader categories of Gram-negative bacteria, such as *Xanthomonas* species, and Gram-positive bacteria, including members of the genera *Bacillus*, such as *B. pumilus, B. subtilis* and *B. coagulans; Clostridium*, for example, *C. acetobutylicum, C. aerotolerans, C. thermocellum, C. thermohydrosulfuricum* and *C. thermosaccharolyticum; Cellulomonas* species like *Cellulomonas uda*; and *Butyrivibrio fibrisolvens*. In addition to *E. coli*, for example, other enteric bacteria of the genera *Erwinia*, like *E. chrysanthemi*, and *Klebsiella*, like *K. planticola* and *K. oxytoca*, can be used. In some embodiments, the host microorganism can be *Zymomonas mobilis*. Similarly acceptable host organisms are various yeasts, exemplified by species of *Cryptococcus* like *Cr. albidus*, species of *Monilia, Pichia stipitis* and *Pullularia pullulans*, and *Saccharomyces cerevisiae*; and other oligosaccharide-metabolizing bacteria, including but not limited to *Bacteroides succinogenes, Thermoanaerobacter* species like *T. ethanolicus, Thermoanaerobium* species such as *T. brockii, Thermobacteroides* species like *T. acetoethylicus*, and species of the genera *Ruminococcus* (for example, *R. flavefaciens*), *Thermonospora* (such as *T. fusca*) and *Acetivibrio* (for example, *A. cellulolyticus*). In some embodiments, a host organism can be selected, for example, from an algae such as, for example, *Amphora, Anabaena, Anikstrodesmis, Botryococcus, Chaetoceros, Chlorella, Chlorococcum, Cyclotella, Cylindrotheca, Dunaliella, Euglena, Hematococcus, Isochrysis, Monoraphidium, Nannochloris, Nannnochloropsis, Navicula, Nephrochloris, Nephroselmis, Nitzschia, Nodularia, Nostoc, Oochromonas, Oocystis, Oscillartoria, Pavlova, Phaeodactylum, Playtmonas, Pleurochrysis, Porhyra, Pseudoanabaena, Pyramimonas, Stichococcus, Synechococcus, Tetraselmis, Thalassiosira, Trichodesmium*. The literature relating to microorganisms which meet the subject criteria is reflected, for example, in Biely, *Trends in Biotech.* 3: 286-90 (1985), in Robsen et al., *Enzyme Microb. Technol.* 11: 626-44 (1989), and in Beguin *Ann. Rev. Microbiol.* 44: 219-48 (1990), each of which is herein incorporated by reference in its entirety. Appropriate transformation methodology is available for each of these different types of hosts and is described in detail below. See also, e.g., Brat et al. Appl. Env. Microbiol. 29; 75:2304-2311, disclosing expression of xylose isomerase in *Saccharomyces cerevisiae*.

In some embodiments, a host microorganism can be selected by, for example, its ability to produce the proteins necessary to transport an oligosaccharide into the cell and its intracellular levels of enzymes which metabolize those oligosaccharides. Examples of such microorganisms include enteric bacteria like *E. chysanthemi* and other *Erwinia*, and *Klebsiella* species such as *K. oxytoca*, which naturally produces a β-xylosidase, and *K. planticola*. Certain *E. coli* are attractive hosts because they transport and metabolize cellobiose, maltose and/or maltotriose. See, for example, Hall et al., J. Bacteriol. 169: 2713-17 (1987).

In some embodiments, a host microorganism can be selected by screening to determine whether the tested microorganism transports and metabolizes oligosaccharides. Such screening can be accomplished in various ways. For example, microorganisms can be screened to determine which grow on suitable oligosaccharide substrates, the screen being designed to select for those microorganisms that do not transport only monomers into the cell. See, for example, Hall et al. (1987), supra. Alternatively, microorganisms can be assayed for appropriate intracellular enzyme activity, e.g., β-xylosidase activity. Growth of potential host microorganisms can be further screened for ethanol tolerance, salt tolerance, and temperature tolerance. See Alterhum et al., *Appl. Environ. Microbiol.* 55: 1943-48 (1989); Beall et al., *Biotechnol. & Bioeng.* 38: 296-303 (1991).

In some embodiments, a host microorganism can exhibit one or more of the following characteristics: the ability to grow in ethanol concentrations above 1% ethanol, the ability to tolerate salt levels of, for example, 0.3 molar, the ability to tolerate acetate levels of, for example, 0.2 molar, and the ability to tolerate temperatures of, for example, 40° C., and the ability to produce high levels of enzymes useful for cellulose, hemicellulose and pectin depolymerization with minimal protease activity. In some embodiments a host microorganism may also contain native xylanases or cellulases. In some embodiments, after introduction of expression vectors for fuel production, a host can produce ethanol from various saccharides tested with greater than, for examples, 90% of theoretical yield while retaining one or more useful traits above.

Transformation of Host Cells

Some embodiments relate to methods for introducing any of the polynucleotides, polynucleotide cassettes, expression cassettes, and expression vectors described herein into a cell of a host microorganism. Such embodiments thereby producing a recombinant microorganism that is capable of producing a fuel when cultured under a variety of fermentation conditions. Methods of transforming cells are well known in the art, and can include, for example, electroporation, lipofection, transfection, conjugation, chemical transformation, injection, particle infloe gun bombardment, and magnetophoresis. Magnetophoresis uses magnetophoresis and nanotechnology fabrication of micro-sized linear magnets to introduce nucleic acids into cells (Kuehnle et al., U.S. Pat. No. 6,706,394; 2004; Kuehnle et al., U.S. Pat. No. 5,516,670; 1996). In some embodiments, electrotransformation of methylated plasmids into *C. phytofermentans* can be carried out according to a protocol developed by Mermelstein (Mermelstein, et al. Bio/Technology 10: 190-195 (1992)). More methods can include transformation by conjugation. In other embodiments, positive transformants can be isolated on agar-solidified CGM supplemented with the appropriate antibiotic.

In various embodiments, the transformation methods can be coupled with one or more methods for visualization or quantification of nucleic acid introduction to one or more microorganisms. Further, it is taught that this can be coupled with identification of any line showing a statistical difference in, for example, growth, fluorescence, carbon metabolism, isoprenoid flux, or fatty acid content from the unaltered phenotype. The transformation methods can also be coupled with visualization or quantification of a product resulting from expression of the introduced nucleic acid.

Typically, prior to transformation into *C. phytofermentans*, vectors comprising plasmid DNA can be methylated to prevent restriction by Clostridial endonucleases. (Mermelstein and Papoutsakis. Appl. Environ. Microbiol. 59: 1077-1081 (1993)). In some embodiments, methylation can be accomplished by the phi3TI methyltransferase. In further embodiments, plasmid DNA can be transformed into DH10β. *E. coli* harboring vector pDHKM (Zhao, et al. Appl. Environ. Microbiol. 69: 2831-41 (2003)) carrying an active copy of the phi3TI methyltransferase gene.

Generally, *C. phytofermentans* strains can be grown anaerobically in Clostridial Growth Medium (CGM) at 37° C. supplemented with an appropriate antibiotic, such as 40 μg/ml erythromycin/chloramphenicol or 25 μg/ml thiamphenicol (Hartmanis and Gatenbeck. Appl. Environ. Microbiol. 47: 1277-83 (1984)). In addition, *C. phytofermentans* strains can be cultured in closed-cap batch fermentations of 100 ml CGM supplemented with the appropriate antibiotic 37° C. in a FORMA SCIENTIFIC™ anaerobic chamber (THERMO FORMA™, Marietta, Ohio).

In other embodiments, *C. phytofermentans* can be cultured according to the techniques of Hungate (Hungate, R. E. (1969). A roll tube method for cultivation of strict anaerobes. Methods Microbiol 3B, 117-132.). Medium GS-2C can be used for enrichment, isolation and routine cultivation of strains of *C. phytofermentans*, and can be derived from GS-2 of Johnson et al (Johnson, E. A., Madia, A. & Demain, A. L. (1981). Chemically defined minimal medium for growth of the anaerobic cellulolytic thermophile *Clostridium thermocellum*. Appl Environ Microbiol 41, 1060-1062). GS-2C can contain the following: 6.0 g/l ball-milled cellulose (Leschine, S. B. & Canale-Parola, E. (1983). Mesophilic cellulolytic clostridia from freshwater environments. Appl Environ Microbiol 46, 728-737.); 6.0 g/l yeast extract; 2.1 g/l urea; 2.9 g/l $K_2HPO_4$; 1.5 g/l $KH_2PO_4$; 10.0 g/l MOPS; 3.0 g/l trisodium citrate dihydrate; 2.0 g/l cysteine hydrochloride; 0.001 g/l resazurin; with the pH adjusted to 7.0. Broth cultures can be incubated in an atmosphere of $O_2$-free $N_2$ at 30° C. Cultures on plates of agar media can be incubated at room temperature in an atmosphere of $N_2/CO_2/H_2$ (83:10:7) in an anaerobic chamber (Coy Laboratory Products).

Growth, Expression, and Fuel Production

Some embodiments relate to the production of fuel utilizing any recombinant microorganism described herein. In some embodiments, one or more different recombinant microorganism can be used in combination to produce fuel. Such combinations can include more than one different type of recombinant microorganism in a single fermentation reaction. Other combinations can include one or more different type of recombinant microorganism used in sequential steps of a process to produce fuel from biomass. In some embodiments, a single recombinant microorganism can be used to produce fuel from biomass. In some embodiments, a recombinant microorganism can be used to catalyse the production of products such as saccharides and polysaccharides from lignocellulose and other substrates.

In some embodiments, a recombinant microorganism can be cultured under conditions suitable for expression of genes from expression cassettes contained therein and for the production of fuel. In certain embodiments, incubation conditions can vary depending on the host microorganism used. In some embodiments, incubation conditions can vary according to the type of regulatory element that may be associated with expression cassettes. For example, recombinant organism containing an expression cassette comprising an inducible promoter linked to a nucleic acid may require the addition of a particular agent to the culture medium for expression of the nucleic acid.

In other embodiments, the recombinant microorganism can be a strain of *C. phytofermentans* utilized to ferment a broad spectrum of materials into fuels with high efficiency as described in co-pending U.S. Patent Application No. 2007/0178569 and U.S. Provisional Patent Application No. 61/032, 048, filed Feb. 28, 2008; both references hereby incorporated expressly in their entireties. In some embodiments, the *C. phytofermentans* strain can be American Type Culture Collection 700394$^T$.

In some embodiments, the process utilized to ferment a substrate (e.g., lignocellulosic feedstock) can include: (1) providing a pretreated biomass-derived material comprising a plant polysaccharide (wherein pretreatment can be cutting, chopping, grinding, or the like); (2) inoculating the pretreated biomass-derived material with a first culture comprising a cellulolytic anaerobic microorganism (e.g., a microorganism disclosed herein) in the presence of oxygen to generate an aerobic broth, wherein the anaerobic microorganism is capable of at least partially hydrolyzing the plant polysaccharide; and (3) fermenting the inoculated anaerobic broth until a portion of the plant polysaccharide has been converted into ethanol. In other embodiments, the process utilized to ferment a substrate can include: (1) providing a pretreated biomass-derived material comprising a plant polysaccharide (wherein pretreatment can be cutting, chopping, grinding, or the like); (2) inoculating the pretreated biomass-derived material with a first culture comprising a cellulolytic aerobic microorganism (e.g., a microorganism disclosed herein) in the presence of oxygen to generate an aerobic broth, wherein the aerobic microorganism is capable of at least partially hydrolyzing the plant polysaccharide; (3) incubating the aerobic broth until the cellulolytic aerobic microorganism consumes at least a portion of the oxygen and hydrolyzes at least a portion of the plant polysaccharide, thereby converting the aerobic broth into an anaerobic broth comprising a hydrolysate comprising fermentable sugars; (4) inoculating the anaerobic broth with a second culture comprising an anaerobic microorganism (e.g., a microorganism disclosed herein) capable of converting the fermentable sugars into ethanol; and (5) fermenting the inoculated anaerobic broth until a portion of the fermentable sugars have been converted into ethanol.

Efficiency of a fermentation can be measured in a variety of ways, for example changes in efficiency can be measured in comparison to a wild type organism. Also, changes in efficiency can be measured as the ratio of production of a fuel from a substrate, such as cellulose, per unit of time between a recombinant organism and a wildtype organism. In some embodiments, changes in efficiency between a recombinant organism and a wild type organism can be more than 1%, more than 5%, more than 10%, more than 15%, more than 20%, more than 25%, more than 30%, more than 35%, more than 40%, more than 45%, more than 50%, more than 55%, more than 60%, more than 65%, more than 70%, more than 75%, more than 80%, more than 85%, more than 90%, more than 95%, more than 100%, and more than 200%.

Various media for growing a variety of microorganisms are known in the art. Growth medium may be minimal and/or defined, or complete and/or complex. Fermentable carbon sources can include pretreated or non-pretreated feedstock containing cellulosic, hemicellulosic, and/or lignocellulosic material such as, saw dust, wood flour, wood pulp, paper pulp, paper pulp waste steams, grasses, such as, switchgrass, biomass plants and crops, such as, crambe, algae, rice hulls, bagasse, jute, leaves, grass clippings, corn stover, corn cobs, corn grain, corn grind, distillers grains, and pectin.

Additional nutrients can be present in a fermentation reaction, including nitrogen-containing compounds such as amino acids, proteins, hydrolyzed proteins, ammonia, urea, nitrate, nitrite, soy, soy derivatives, casein, casein derivatives, milk powder, milk derivatives, whey, yeast extract, hydrolyze yeast, autolyzed yeast, corn steep liquor, corn steep solids, monosodium glutamate, and/or other fermentation nitrogen sources, vitamins, and/or mineral supplements. In some embodiments, one or more additional lower molecular weight carbon sources can be added or be present such as glucose, sucrose, maltose, corn syrup, lactic acid, etc. In some embodiments, one possible form of growth media can be modified Luria-Bertani (LB) broth (with 10 g Difco tryptone, 5 g Difco yeast extract, and 5 g sodium chloride per liter) as described by Miller J. H. (1992).

Enhanced production of fuel can be observed after host cells competent to produce fuel are transformed with the expression vectors described herein and the recombinant microorganisms are grown under suitable conditions. Enhanced production of fuel may be observed by standard methods known to those skilled in the art.

In some embodiments, growth and production of the recombinant microorganisms disclosed herein can be performed in normal batch fermentations, fed-batch fermentations or continuous fermentations. In certain embodiments, it is desirable to perform fermentations under reduced oxygen or anaerobic conditions for certain hosts. In other embodiments, fuel production can be performed with levels of oxygen sufficient to allow growth of aerobic organisms; and, optionally with the use of air-lift or equivalent fermentors. In some embodiments, the recombinant microorganisms are grown using batch cultures. In some embodiments, the recombinant microorganisms are grown using bioreactor fermentation. In some embodiments, the growth medium in which the recombinant microorganisms are grown is changed, thereby allowing increased levels of fuel production. The number of medium changes may vary.

The pH of the fermentation can be sufficiently high to allow growth and fuel production by the host. Adjusting the pH of the fermentation broth may be performed using neutralizing agents such as calcium carbonate or hydroxides. The selection and incorporation of any of the above fermentative methods is highly dependent on the host strain and the downstream process utilized.

In some embodiments, organic solvents can be purified from biomass fermented with C. phytofermentans by a variety of means. In certain embodiments, organic solvents are purified by distillation. In exemplary embodiments, about 96% ethanol can be distilled from the fermented mixture. In further embodiments, fuel grade ethanol, namely about 99-100% ethanol, can be obtained by azeotropic distillation of about 96% ethanol. Azeotrophic distillation can be accomplished by the addition of benzene to about 96% ethanol and then re-distilling the mixture. Alternatively, about 96% ethanol can be passed through a molecular sieve to remove water.

In some embodiments, methods of producing fuel can include culturing any microorganism described herein and supplying a protein expressed by a polynucleotide, polynucleotide cassette, expression cassette, expression vector comprising any nucleic acid encoding a predicted gene identified in C. phytofermentans described herein to the culture medium. In particular embodiments, the nucleic acid can encode a hydrolase. In certain embodiments, isolated proteins can be supplied to a culture medium.

The following examples are by way of illustration and not by way of limitation.

EXAMPLES

Example 1

Identification of DNA Sequences in C. Phytofermentans

Construction, isolation and sequencing of insert libraries. Genomic DNA was sequenced using a conventional whole genome shotgun strategy. Briefly, random 2-3 kb DNA fragments were isolated after mechanical shearing. These gel-extracted fragments were concentrated, end-repaired and cloned into pUC18. Double-ended plasmid sequencing reactions were carried out using PE BigDye™ Terminator chemistry (Perkin Elmer) and sequencing ladders were resolved on PE 3700 Automated DNA Sequencers. One round (x reads) of small-insert library sequencing was done, generating x-fold redundancy.

Sequence assembly and gap closure. Sequence traces were processed with Phred43, 44 for base calling and assessment of data quality before assembly with Phrap (P. Green, University of Washington, Seattle, Wash., USA) and visualization with Consed45.

Sequence analysis and annotation. Gene modeling was done using the Critica47, Glimmer48 and Generation (compbio.ornl.gov/generation/index.shtml) modeling packages, the results were combined and a basic local alignment search tool for proteins (BLASTP) search of the translations versus GenBank's nonredundant database (NR) was conducted. The alignment of the N terminus of each gene model versus the best NR match was used to pick a gene model. If no BLAST match was returned, the Critica model was retained. Gene models that overlapped by greater than 10% of their length were flagged, giving preference to genes with a BLAST match. The revised gene/protein set was searched against the KEGG GENES, InterPro (incorporating Pfam, TIGRFams, SmartHMM, PROSITE, PRINTS and ProDom) and Clusters of Orthologous Groups of proteins (COGs) databases, in addition to BLASTP versus NR. From these results, categorizations were developed using the KEGG and COGs hierarchies. Initial criteria for automated functional assignment required a minimum 50% residue identity over 80% of the length of the match for BLASTP alignments, plus concurring evidence from pattern or profile methods. Putative assignments were made for identities down to 30%, over 80% of the length.

Using BLASTP, each C. phytofermentans genes were searched against all genes from sequenced genomes, the first blast of each predicted protein was extracted. Analysis of the theoretical subcellular localization and signal peptide cleavage sites were carried out using PSORT (psort.hgcjp/form.html). CAZy domains were annotated by CAzy ((carbohydrate-active enzymes, www.cazy.org)). Transporters were annotated using TransportDB (www.membranetransport.org). The complete sequence of *C. phytofermentans* was made available in August 2007 (accession number NC_010001).

Example 2

Expression Analysis of DNA Sequences in *C. Phytofermentans*

Microarray design. The *C. phytofermentans* custom Affymetrix microarray design (FIG. 3) enables the measurement of the expression level of all identified open reading frames (ORFs), estimation of the 5' and 3' untranslated regions of mRNA, operon determination, tRNA discovery, and discriminating between alternative gene models (primarily differing in the selection of the start codon).

Putative protein coding sequences were identified using GeneMark™ (Besemer, J., and M. Borodovsky. 2005. GeneMark: web software for gene finding in prokaryotes, eukaryotes and viruses. Nucleic Acids Res 33:W451-4) and Glimmer (Delcher, A. L., K. A. Bratke, E. C. Powers, and S. L. Salzberg. 2007. Identifying bacterial genes and endosymbiont DNA with Glimmer. Bioinformatics 23:673-9) prediction programs. The union of these two predictions was used as the expression set. If two proteins differed in their N-terminal region, the smaller of the two proteins was used for transcript analysis, but the extended region was represented by probes in order to define the actual N-terminus. This array design resulted in the inclusion of all proteins represented in the GenBank record and included additional ORFs not found in the GenBank record. Standard Affymetrix array design protocols were followed to ensure each probe was unique in order to minimize cross hybridization. The array design was implemented on a 49-5241 format Affymetrix GeneChip™ array with 11µ features.

Cell culture growth and RNA isolation. *C. phytofermentans* was cultured in tubes or 500 ml Erlenmeyer flasks at 30° C. under 100% $N_2$ in GS2 medium supplemented with 0.3% (wt/vol) with one of fourteen specific carbon sources (glucose; xylan; cellobiose; cellulose; D-arabinose; L-arabinose; fucose; galactose; laminarin; mannose; pectin; rhamnose; xylose; or yeast extract). Growth was determined spectrophotometrically by monitoring changes in optical density at 660 nm.

RNA was purified from mid-exponential phase cultures ($OD_{660}$=0.5). Samples of 1 ml were flash-frozen by immersion in liquid nitrogen. Cells were collected by centrifugation for 5 minute at 8,000 rpm at 4° C., and the total RNA isolated using Qiagen RNeasy™ Mini Kit and treatment with RNAse-free DNase I. RNA concentration was determined by absorbance at 260/280 nm using a Nanodrop™ spectrophotometer.

Microarray processing. cDNA synthesis, array hybridization and imaging were performed at the Genomic Core Facility at the University of Massachusetts Medical Center. 10 µg total RNA from each sample was used as template to synthesize labeled cDNAs using Affymetrix GeneChip™ DNA Labeling Reagent Kits. The labeled cDNA samples were hybridized with the Affymetrix GeneChip™ Arrays according to Affymetrix guidelines. The hybridized arrays were scanned with a GeneChip™ Scanner 3000. The resulting raw spot image data files were processed into pivot, quality report, and normalized probe intensity files using Microarray Suite version 5.0 (MAS 5.0). Expression values were calculated using a custom software package implementing the GCRMA method.

The quality of the microarray data were analyzed using probe-level modeling procedures provided by the affyPLM package (Bolstad, B. M., F. Collin, J. Brettschneider, K. Simpson, L. Cope, R. Irizarray, and T. P. Speed. 2005. Quality Assessment of Affymetrix GeneChip Data, p. 33-47. In R. Gentleman, V. Carey, W. Huber, and S. Dutoit (ed.), Bioinformatics and Computational Biology Solutions Using R and Bioconductor. Springer, Heidelberg.) in BioConductor (Gentleman, R. C., V. J. Carey, D. M. Bates, B. Bolstad, M. Dettling, S. Dudoit, B. Ellis, L. Gautier, Y. Ge, J. Gentry, K. Hornik, T. Hothorn, W. Huber, S. Iacus, R. Irizarry, F. Leisch, C. Li, M. Maechler, A. J. Rossini, G. Sawitzki, C. Smith, G. Smyth, L. Tierney, J. Y. Yang, and J. Zhang. 2004. Bioconductor: open software development for computational biology and bioinformatics. Genome Biol 5:R80). No image artifacts due to array manufacturing or processing were observed. Microarray background values of 34 (glucose), 32 (cellobiose), 30 (xylose) and 34 (cellulose) were within the typical 20-100 average background values for Affymetrix arrays. Quality control checks for procedures adapted for use in *C. phytofermentans*, namely, RNA purification, cDNA synthesis, labeling and hybridization, indicated a high quality of data.

Estimation of mRNA transcript boundaries. To identify putative promoter sequences the length of mRNA transcripts was estimated with an error of +/−24 bases. Expression levels of intergenic regions adjacent to the ORF and regions within the ORF were compared using specific probes (FIG. 4). Readings above 1000 A.U. indicated that a specific probe represented part of an expressed region. Conversely, readings below 250 A.U. indicated no specific hybridization between probe and an expressed region. Probes indicating a putative expressed region had a reading greater than:

Mean(gene1)−stdev(gene1) or mean(gene2)−stdev(gene2).

To avoid errors from a single probe, readings from at least two consecutive probes were used to indicate an expressed region. However, because some probes may have properties that make them unresponsive, single probes with readings below the threshold were included in mapping expressed regions where consecutive probes upstream and downstream of the unresponsive probe met the criteria. This allowed for better quantification of transcript boundaries of low expression level genes and consolidated adjacent expressed intergenic region calls.

BLAST was used to identify potential sources of cross-hybridization, by running BLAST for every detected probe against the *C. phytofermentans* genome. For any matches with E-values lower than 0.01, the intensities were measured for probes on the array corresponding to the BLAST match. If any of the matches exhibited an expression value higher than the probe in question, the probe was tagged as a possible source for cross-hybridization. For each putative expressed region, the number of positive probes and the number of these positive probes considered to be possible cross-hybridizations was reported. Transcript boundaries for every predicted Glycoside hydrolase-related protein and putative alcohol dehydrogenase were reported.

Genes corresponding to transcripts observed to be differentially expressed more than 4-fold during growth on D-arabinose as compared to growth on glucose are presented in Table 10.

TABLE 10

Expression on D-arabinose

| Differential Expression (log$_2$) | JGI No. | COG Description |
|---|---|---|
| 5.1 | Cphy1174 | pyruvate formate-lyase |
| 5.0 | Cphy1175 | glycyl-radical enzyme activating protein family |
| 4.9 | Cphy1176 | microcompartments protein |
| 6.1 | Cphy1177 | class II aldolase/adducin family protein |
| 5.9 | Cphy1178 | Aldehyde Dehydrogenase |
| 5.3 | Cphy1179 | Alcohol dehydrogenase zinc-binding domain protein |
| 5.6 | Cphy1180 | microcompartments protein |
| 5.7 | Cphy1181 | microcompartments protein |
| 5.0 | Cphy1182 | microcompartments protein |
| 4.5 | Cphy1183 | Propanediol utilization protein |
| 3.9 | Cphy1184 | Ethanolamine utilization protein EutN/carboxysome structural protein Ccml |
| 3.4 | Cphy1185 | Respiratory-chain NADH dehydrogenase domain 51 kDa subunit |
| 3.9 | Cphy3153 | RbsD or FucU transport |
| 4.4 | Cphy3154 | carbohydrate kinase FGGY |
| 4.4 | Cphy3155 | L-fucose isomerase |
| 2.6 | Cphy3367 | Cellulose 1,4-beta-cellobiosidase |
| 2.8 | Cphy3368 | Cellulose 1,4-beta-cellobiosidase |

Genes corresponding to transcripts observed to be differentially expressed more than 4-fold during growth on L-arabinose as compared to growth on glucose are presented in Table 11.

TABLE 11

Expression on L-arabinose

| Differential Expression (log$_2$) | JGI No. | COG Description |
|---|---|---|
| 2.1 | Cphy0580 | ABC transporter related |
| 2.1 | Cphy0581 | Monosaccharide-transporting ATPase |
| 2.7 | Cphy0582 | Monosaccharide-transporting ATPase |
| 2.3 | Cphy0583 | putative sugar ABC transporter, substrate-binding protein |
| 4.3 | Cphy1071 | glycoside hydrolase family 26 |
| 2.0 | Cphy1169 | Alpha-N-arabinofuranosidase |
| 3.9 | Cphy1219 | xylose isomerase |
| 6.9 | Cphy1799 | Glycoside hydrolase, family 18: Carbohydrate-binding family V/XII precursor |
| 6.3 | Cphy1800 | Chitinase precursor |
| 3.2 | Cphy2105 | Endo-1,4-beta-xylanase |
| 2.5 | Cphy2128 | Mannan endo-1,4-beta-mannosidase, Cellulose 1,4-beta-cellobiosidase |
| 2.3 | Cphy2569 | extracellular solute-binding protein family 1 |
| 3.7 | Cphy2570 | binding-protein-dependent transport systems inner membrane component |
| 3.6 | Cphy2571 | binding-protein-dependent transport systems inner membrane component |
| 2.2 | Cphy2919 | protein of unknown function DUF1565 |
| 2.0 | Cphy3202 | Cellulase |
| 4.9 | Cphy3367 | Cellulose 1,4-beta-cellobiosidase |
| 5.7 | Cphy3368 | Cellulose 1,4-beta-cellobiosidase |
| 2.7 | Cphy3419 | xylulokinase |
| 3.0 | Cphy3854 | glycosyltransferase 36 |
| 3.5 | Cphy3855 | Phosphomannomutase |
| 2.5 | Cphy3858 | extracellular solute-binding protein family 1 |
| 3.9 | Cphy3859 | binding-protein-dependent transport systems inner membrane component |
| 3.9 | Cphy3860 | binding-protein-dependent transport systems inner membrane component |
| 3.1 | Cphy3861 | two component transcriptional regulator, AraC family |
| 2.3 | Cphy3862 | Endo-1,4-beta-xylanase |

Genes corresponding to transcripts observed to be differentially expressed more than 4-fold during growth on cellobiose as compared to growth on glucose are presented in Table 12.

TABLE 12

Expression on Cellobiose

| Differential Expression (log$_2$) | JGI No. | COG Description |
|---|---|---|
| 3.5 | Cphy0430 | glycosyltransferase 36 |
| 2.1 | Cphy1586 | ABC transporter related |
| 2.3 | Cphy1587 | Monosaccharide-transporting ATPase |
| 2.0 | Cphy2264 | glycosidase PH1107-related |
| 1.9 | Cphy2265 | extracellular solute-binding protein family 1 |
| 2.0 | Cphy2266 | hypothetical protein |
| 2.2 | Cphy2267 | binding-protein-dependent transport systems inner membrane component |
| 2.3 | Cphy2268 | binding-protein-dependent transport systems inner membrane component |
| 2.3 | Cphy2269 | hypothetical protein |
| 2.3 | Cphy2270 | — |
| 2.0 | Cphy2271 | — |
| 2.1 | Cphy2272 | binding-protein-dependent transport systems inner membrane component |
| 2.2 | Cphy2273 | binding-protein-dependent transport systems inner membrane component |
| 4.3 | Cphy2464 | binding-protein-dependent transport systems inner membrane component |
| 3.8 | Cphy2465 | binding-protein-dependent transport systems inner membrane component |
| 2.7 | Cphy2466 | extracellular solute-binding protein family 1 |
| 3.4 | Cphy2467 | transcriptional regulator, LacI family |

Genes corresponding to transcripts observed to be differentially expressed more than 4-fold during growth on cellulose as compared to growth on glucose are presented in Table 13.

TABLE 13

Expression on Cellulose

| Differential Expression (log$_2$) | JGI No. | COG Description |
|---|---|---|
| 3.4 | Cphy0430 | glycosyltransferase 36 |
| 3.1 | Cphy1071 | glycoside hydrolase family 26 |
| 3.0 | Cphy1163 | Cellulase |
| 4.1 | Cphy1529 | extracellular solute-binding protein family 1 |
| 3.2 | Cphy1530 | binding-protein-dependent transport systems inner membrane component |

TABLE 13-continued

Expression on Cellulose

| Differential Expression (log$_2$) | JGI No. | COG Description |
|---|---|---|
| 3.6 | Cphy1531 | binding-protein-dependent transport systems inner membrane component |
| 2.1 | Cphy1586 | ABC transporter related |
| 2.3 | Cphy1587 | Monosaccharide-transporting ATPase |
| 6.2 | Cphy1799 | glycoside hydrolase family 18 |
| 6.2 | Cphy1800 | glycoside hydrolase family 18 |
| 2.0 | Cphy1929 | glycosyltransferase 36 |
| 3.2 | Cphy2105 | Endo-1,4-beta-xylanase |
| 2.6 | Cphy2263 | hypothetical protein |
| 2.0 | Cphy2264 | glycosidase PH1107-related |
| 2.9 | Cphy2265 | extracellular solute-binding protein family 1 |
| 2.0 | Cphy2266 | hypothetical protein |
| 2.2 | Cphy2267 | binding-protein-dependent transport systems inner membrane component |
| 2.3 | Cphy2268 | binding-protein-dependent transport systems inner membrane component |
| 2.3 | Cphy2269 | hypothetical protein |
| 3.0 | Cphy2270 | — |
| 2.7 | Cphy2271 | — |
| 2.1 | Cphy2272 | binding-protein-dependent transport systems inner membrane component |
| 2.2 | Cphy2273 | binding-protein-dependent transport systems inner membrane component |
| 2.3 | Cphy2274 | extracellular solute-binding protein family 1 |
| 4.0 | Cphy2464 | binding-protein-dependent transport systems inner membrane component |
| 3.5 | Cphy2465 | binding-protein-dependent transport systems inner membrane component |
| 2.5 | Cphy2466 | extracellular solute-binding protein family 1 |
| 3.0 | Cphy2467 | transcriptional regulator, LacI family |
| 2.9 | Cphy2569 | extracellular solute-binding protein family 1 |
| 3.9 | Cphy2570 | binding-protein-dependent transport systems inner membrane component |
| 3.9 | Cphy2571 | binding-protein-dependent transport systems inner membrane component |
| 2.0 | Cphy3209 | binding-protein-dependent transport systems inner membrane component |
| 2.0 | Cphy3210 | putative multiple sugar transport system substrate-binding protein |
| 4.8 | Cphy3367 | Cellulose 1,4-beta-cellobiosidase |
| 5.5 | Cphy3368 | Cellulose 1,4-beta-cellobiosidase |
| 2.5 | Cphy3854 | glycosyltransferase 36 |
| 3.1 | Cphy3855 | Phosphomannomutase |
| 2.5 | Cphy3858 | extracellular solute-binding protein family 1 |
| 3.8 | Cphy3859 | binding-protein-dependent transport systems inner membrane component |
| 3.7 | Cphy3860 | binding-protein-dependent transport systems inner membrane component |
| 2.9 | Cphy3861 | two component transcriptional regulator, AraC family |
| 2.3 | Cphy3862 | Endo-1,4-beta-xylanase |

Genes corresponding to transcripts observed to be differentially expressed at or more than 4-fold during growth on fucose as compared to growth on glucose are presented in Table 14.

TABLE 14

Expression on Fucose

| Differential Expression (log$_2$) | JGI No. | COG Description |
|---|---|---|
| 2.7 | Cphy0580 | ABC transporter related |
| 2.6 | Cphy0581 | Monosaccharide-transporting ATPase |
| 2.8 | Cphy0582 | Monosaccharide-transporting ATPase |
| 2.2 | Cphy0583 | putative sugar ABC transporter, substrate-binding protein |
| 2.2 | Cphy0584 | L-arabinose isomerase |

TABLE 14-continued

Expression on Fucose

| Differential Expression (log$_2$) | JGI No. | COG Description |
|---|---|---|
| 2.8 | Cphy1071 | glycoside hydrolase family 26 |
| 2.8 | Cphy1163 | Cellulase |
| 5.6 | Cphy1174 | pyruvate formate-lyase |
| 6.2 | Cphy1175 | glycyl-radical enzyme activating protein family |
| 5.8 | Cphy1176 | microcompartments protein |
| 6.5 | Cphy1177 | class II aldolase/adducin family protein |
| 6.4 | Cphy1178 | Aldehyde Dehydrogenase_ |
| 6.3 | Cphy1179 | Alcohol dehydrogenase zinc-binding domain protein |
| 6.4 | Cphy1180 | microcompartments protein |
| 6.4 | Cphy1181 | microcompartments protein |
| 6.0 | Cphy1182 | microcompartments protein |
| 5.9 | Cphy1183 | Propanediol utilization protein |
| 5.4 | Cphy1184 | Ethanolamine utilization protein EutN/carboxysome structural protein CcmI |
| 5.2 | Cphy1185 | Respiratory-chain NADH dehydrogenase domain 51 kDa subunit |
| 4.7 | Cphy1186 | microcompartments protein |
| 4.9 | Cphy1799 | glycoside hydrolase family 18 |
| 5.2 | Cphy1800 | glycoside hydrolase family 18 |
| 6.1 | Cphy2010 | ABC transporter related |
| 6.6 | Cphy2011 | Monosaccharide-transporting ATPase |
| 5.9 | Cphy2012 | periplasmic binding protein/LacI transcriptional regulator |
| 2.0 | Cphy2105 | Endo-1,4-beta-xylanase |
| 2.4 | Cphy2569 | extracellular solute-binding protein family 1 |
| 3.3 | Cphy2570 | binding-protein-dependent transport systems inner membrane component |
| 3.0 | Cphy2571 | binding-protein-dependent transport systems inner membrane component |
| 2.5 | Cphy2919 | protein of unknown function DUF1565 |
| 4.9 | Cphy3153 | RbsD or FucU transport |
| 5.3 | Cphy3154 | carbohydrate kinase FGGY |
| 5.3 | Cphy3155 | L-fucose isomerase |
| 2.3 | Cphy3308 | hypothetical protein |
| 4.2 | Cphy3367 | Cellulose 1,4-beta-cellobiosidase |
| 4.7 | Cphy3368 | Cellulose 1,4-beta-cellobiosidase |
| 2.1 | Cphy3854 | glycosyltransferase 36 |
| 2.3 | Cphy3855 | Phosphomannomutase |
| 2.3 | Cphy3858 | extracellular solute-binding protein family 1 |
| 3.3 | Cphy3859 | binding-protein-dependent transport systems inner membrane component |
| 3.2 | Cphy3860 | binding-protein-dependent transport systems inner membrane component |
| 2.3 | Cphy3861 | two component transcriptional regulator, AraC family |

Genes corresponding to transcripts observed to be differentially expressed at or more than 4-fold during growth on galactose as compared to growth on glucose are presented in Table 15.

TABLE 15

Expression on Galactose

| Differential Expression (log$_2$) | JGI No. | COG Description |
|---|---|---|
| 2.1 | Cphy3367 | Cellulose 1,4-beta-cellobiosidase |
| 2.0 | Cphy3368 | Cellulose 1,4-beta-cellobiosidase |

Genes corresponding to transcripts observed to be differentially expressed more than 4-fold during growth on laminarin as compared to growth on glucose are presented in Table 16.

TABLE 16

Expression on Laminarin

| Differential Expression (log$_2$) | JGI No. | COG Description |
|---|---|---|
| 5.4 | Cphy0857 | Cellobiose phosphorylase-like protein |
| 5.1 | Cphy0858 | glycoside hydrolase family 30 |
| 4.9 | Cphy0859 | hypothetical protein |
| 5.7 | Cphy0860 | binding-protein-dependent transport systems inner membrane component |
| 5.8 | Cphy0861 | binding-protein-dependent transport systems inner membrane component |
| 3.9 | Cphy0862 | extracellular solute-binding protein family 1 |
| 3.8 | Cphy0863 | histidine kinase internal region |
| 3.8 | Cphy0864 | two component transcriptional regulator, AraC family |
| 4.0 | Cphy0865 | hypothetical protein |
| 2.2 | Cphy1448 | phosphonate ABC transporter, periplasmic phosphonate-binding protein |
| 1.8 | Cphy1449 | phosphonate ABC transporter, ATPase subunit |

TABLE 16-continued

Expression on Laminarin

| Differential Expression (log$_2$) | JGI No. | COG Description |
|---|---|---|
| 1.9 | Cphy1450 | phosphonate ABC transporter, inner membrane subunit |
| 2.0 | Cphy1451 | phosphonate ABC transporter, inner membrane subunit |
| 2.0 | Cphy1929 | glycosyltransferase 36 |
| 4.9 | Cphy3388 | Glucan endo-1,3-beta-D-glucosidase |

Genes corresponding to transcripts observed to be differentially expressed more than 4-fold during growth on mannose as compared to growth on glucose are presented in Table 17.

TABLE 17

Expression on Mannose

| Differential Expression (log$_2$) | JGI No. | COG Description |
|---|---|---|
| 2.6 | Cphy1071 | glycoside hydrolase family 26 |
| 2.5 | Cphy1585 | putative solute-binding component of ABC transporter |
| 2.5 | Cphy1586 | ABC transporter related |
| 2.9 | Cphy1587 | Monosaccharide-transporting ATPase |
| 3.9 | Cphy1799 | glycoside hydrolase family 18 |
| 4.2 | Cphy1800 | glycoside hydrolase family 18 |
| 2.5 | Cphy2105 | Endo-1,4-beta-xylanase |
| 3.1 | Cphy2569 | extracellular solute-binding protein family 1 |
| 3.6 | Cphy2570 | binding-protein-dependent transport systems inner membrane component |
| 3.4 | Cphy2571 | binding-protein-dependent transport systems inner membrane component |
| 3.8 | Cphy3367 | Cellulose 1,4-beta-cellobiosidase |
| 4.1 | Cphy3368 | Cellulose 1,4-beta-cellobiosidase |
| 2.1 | Cphy3855 | Phosphomannomutase |
| 2.4 | Cphy3858 | extracellular solute-binding protein family 1 |
| 3.3 | Cphy3859 | binding-protein-dependent transport systems inner membrane component |
| 3.1 | Cphy3860 | binding-protein-dependent transport systems inner membrane component |
| 2.4 | Cphy3861 | two component transcriptional regulator, AraC family |

Genes corresponding to transcripts observed to be differentially expressed more than 4-fold during growth on pectin as compared to growth on glucose are presented in Table 18.

TABLE 18

Expression on Pectin

| Differential Expression (log$_2$) | JGI No. | COG Description |
|---|---|---|
| 2.7 | Cphy0218 | glycoside hydrolase family 31 |
| 2.2 | Cphy0219 | hypothetical protein |
| 2.5 | Cphy0220 | glycoside hydrolase family 3 domain protein |
| 3.5 | Cphy0430 | glycosyltransferase 36 |
| 2.2 | Cphy1071 | glycoside hydrolase family 26 |
| 2.3 | Cphy1174 | pyruvate formate-lyase |
| 2.4 | Cphy1175 | glycyl-radical enzyme activating protein family |
| 2.1 | Cphy1176 | microcompartments protein |
| 3.3 | Cphy1177 | class II aldolase/adducin family protein |
| 2.9 | Cphy1178 | Aldehyde Dehydrogenase_ |
| 2.3 | Cphy1179 | Alcohol dehydrogenase zinc-binding domain protein |
| 2.9 | Cphy1180 | microcompartments protein |
| 2.8 | Cphy1181 | microcompartments protein |
| 2.2 | Cphy1182 | microcompartments protein |
| 2.1 | Cphy1183 | Propanediol utilization protein |
| 2.0 | Cphy1219 | xylose isomerase |
| 3.2 | Cphy1612 | Pectate lyase/Amb allergen |
| 2.0 | Cphy1714 | glycoside hydrolase family 85 |
| 3.6 | Cphy1715 | binding-protein-dependent transport systems inner membrane component |
| 3.4 | Cphy1716 | binding-protein-dependent transport systems inner membrane component |
| 2.3 | Cphy1717 | extracellular solute-binding protein family 1 |
| 2.7 | Cphy1718 | glycosidase PH1107-related |
| 2.5 | Cphy1719 | hypothetical protein |
| 2.4 | Cphy1720 | glycoside hydrolase family 38 |
| 2.4 | Cphy1888 | hypothetical protein |
| 3.4 | Cphy1929 | glycosyltransferase 36 |
| 2.1 | Cphy2010 | ABC transporter related |
| 2.1 | Cphy2011 | Monosaccharide-transporting ATPase |
| 2.1 | Cphy2262 | N-acylglucosamine 2-epimerase |
| 3.1 | Cphy2263 | hypothetical protein |
| 3.3 | Cphy2264 | glycosidase PH1107-related |
| 3.1 | Cphy2265 | extracellular solute-binding protein family 1 |
| 3.1 | Cphy2266 | hypothetical protein |
| 4.0 | Cphy2267 | binding-protein-dependent transport systems inner membrane component |

TABLE 18-continued

Expression on Pectin

| Differential Expression (log$_2$) | JGI No. | COG Description |
|---|---|---|
| 3.8 | Cphy2268 | binding-protein-dependent transport systems inner membrane component |
| 3.9 | Cphy2269 | hypothetical protein |
| 3.6 | Cphy2270 | — |
| 3.6 | Cphy2271 | — |
| 4.0 | Cphy2272 | binding-protein-dependent transport systems inner membrane component |
| 4.0 | Cphy2273 | binding-protein-dependent transport systems inner membrane component |
| 3.2 | Cphy2274 | extracellular solute-binding protein family 1 |
| 2.4 | Cphy2275 | hypothetical protein |
| 2.1 | Cphy2276 | Mannan endo-1,4-beta-mannosidase |
| 3.9 | Cphy2464 | binding-protein-dependent transport systems inner membrane component |
| 3.5 | Cphy2465 | binding-protein-dependent transport systems inner membrane component |
| 2.4 | Cphy2466 | extracellular solute-binding protein family 1 |
| 2.9 | Cphy2467 | transcriptional regulator, LacI family |
| 2.9 | Cphy2919 | protein of unknown function DUF1565 |
| 2.4 | Cphy3153 | RbsD or FucU transport |
| 2.5 | Cphy3154 | carbohydrate kinase FGGY |
| 2.6 | Cphy3155 | L-fucose isomerase |
| 2.2 | Cphy3160 | glycoside hydrolase family 2 sugar binding |
| 3.4 | Cphy3367 | Cellulose 1,4-beta-cellobiosidase |
| 3.5 | Cphy3368 | Cellulose 1,4-beta-cellobiosidase |
| 4.2 | Cphy3585 | transcriptional regulator, LacI family |
| 6.5 | Cphy3586 | Arabinogalactan endo-1,4-beta-galactosidase |
| 6.8 | Cphy3587 | hypothetical protein |
| 6.5 | Cphy3588 | binding-protein-dependent transport systems inner membrane component |
| 6.1 | Cphy3589 | binding-protein-dependent transport systems inner membrane component |
| 6.7 | Cphy3590 | extracellular solute-binding protein family 1 |
| 2.2 | Cphy3859 | binding-protein-dependent transport systems inner membrane component |
| 2.0 | Cphy3860 | binding-protein-dependent transport systems inner membrane component |

Genes corresponding to transcripts observed to be differentially expressed more than 4-fold during growth on rhamnose as compared to growth on glucose are presented in Table 19.

TABLE 19

Expression on Rhamnose

| Differential Expression (log$_2$) | JGI No. | COG Description |
|---|---|---|
| 3.7 | Cphy1071 | glycoside hydrolase family 26 |
| 3.4 | Cphy1163 | Cellulase |
| 3.2 | Cphy1219 | xylose isomerase |
| 2.8 | Cphy1585 | putative solute-binding component of ABC transporter |
| 3.4 | Cphy1586 | ABC transporter related |
| 3.7 | Cphy1587 | Monosaccharide-transporting ATPase |
| 6.4 | Cphy1799 | glycoside hydrolase family 18 |
| 6.1 | Cphy1800 | glycoside hydrolase family 18 |
| 5.0 | Cphy2105 | Endo-1,4-beta-xylanase |
| 2.0 | Cphy2106 | protein of unknown function DUF323 |
| 2.1 | Cphy2128 | Mannan endo-1,4-beta-mannosidase, Cellulose 1,4-beta-cellobiosidase |
| 2.9 | Cphy2265 | extracellular solute-binding protein family 1 |
| 2.8 | Cphy2569 | extracellular solute-binding protein family 1 |
| 4.0 | Cphy2570 | binding-protein-dependent transport systems inner membrane component |
| 3.9 | Cphy2571 | binding-protein-dependent transport systems inner membrane component |
| 2.1 | Cphy2919 | protein of unknown function DUF1565 |
| 5.1 | Cphy3367 | Cellulose 1,4-beta-cellobiosidase |
| 5.9 | Cphy3368 | Cellulose 1,4-beta-cellobiosidase |
| 2.5 | Cphy3419 | xylulokinase |
| 2.4 | Cphy3854 | glycosyltransferase 36 |
| 2.7 | Cphy3855 | Phosphomannomutase |
| 2.3 | Cphy3858 | extracellular solute-binding protein family 1 |
| 3.8 | Cphy3859 | binding-protein-dependent transport systems inner membrane component |
| 3.8 | Cphy3860 | binding-protein-dependent transport systems inner membrane component |
| 2.9 | Cphy3861 | two component transcriptional regulator, AraC family |

Genes corresponding to transcripts observed to be differentially expressed more than 4-fold during growth on xylan as compared to growth on glucose are presented in Table 20.

TABLE 20

Expression on Xylan

| Differential Expression (log₂) | JGI No. | COG Description |
|---|---|---|
| 2.4 | Cphy1132 | putative solute-binding component of ABC transporter |
| 2.7 | Cphy1133 | Monosaccharide-transporting ATPase |
| 2.6 | Cphy1134 | ABC transporter related |
| 2.2 | Cphy1177 | class II aldolase/adducin family protein |
| 2.1 | Cphy1178 | Aldehyde Dehydrogenase |
| 2.0 | Cphy1181 | microcompartments protein |
| 3.6 | Cphy1219 | xylose isomerase |
| 2.7 | Cphy1448 | phosphonate ABC transporter, periplasmic phosphonate-binding protein |
| 2.3 | Cphy1449 | phosphonate ABC transporter, ATPase subunit |
| 2.5 | Cphy1450 | phosphonate ABC transporter, inner membrane subunit |
| 2.6 | Cphy1451 | phosphonate ABC transporter, inner membrane subunit |
| 2.8 | Cphy1528 | transcriptional regulator, AraC family |
| 6.7 | Cphy1529 | extracellular solute-binding protein family 1 |
| 6.8 | Cphy1530 | binding-protein-dependent transport systems inner membrane component |
| 6.7 | Cphy1531 | binding-protein-dependent transport systems inner membrane component |
| 5.3 | Cphy1532 | Domain of unknown function DUF1801 |
| 4.5 | Cphy2105 | Endo-1,4-beta-xylanase |
| 4.6 | Cphy2106 | protein of unknown function DUF323 |
| 4.8 | Cphy2108 | Endo-1,4-beta-xylanase |
| 2.4 | Cphy2632 | glycoside hydrolase family 43 |
| 2.4 | Cphy2654 | sugar ABC transporter substrate-binding protein |
| 4.2 | Cphy2655 | binding-protein-dependent transport systems inner membrane component |
| 4.3 | Cphy2656 | binding-protein-dependent transport systems inner membrane component |
| 4.3 | Cphy3009 | glycoside hydrolase family 3 domain protein |
| 4.1 | Cphy3010 | Endo-1,4-beta-xylanase |
| 4.6 | Cphy3158 | Alpha-glucuronidase |
| 4.3 | Cphy3206 | methyl-accepting chemotaxis sensory transducer |
| 4.5 | Cphy3207 | glycoside hydrolase family 8 |
| 4.4 | Cphy3208 | binding-protein-dependent transport systems inner membrane component |
| 4.3 | Cphy3209 | binding-protein-dependent transport systems inner membrane component |
| 4.6 | Cphy3210 | putative multiple sugar transport system substrate-binding protein |
| 3.3 | Cphy3211 | two component transcriptional regulator, AraC family |
| 3.0 | Cphy3212 | histidine kinase internal region |
| 3.4 | Cphy3419 | xylulokinase |

Genes corresponding to transcripts observed to be differentially expressed more than 4-fold during growth on xylose as compared to growth on glucose are presented in Table 21.

TABLE 21

Expression on Xylose

| Differential Expression (log₂) | JGI No. | COG Description |
|---|---|---|
| 3.4 | Cphy1071 | glycoside hydrolase family 26 |
| 3.2 | Cphy1219 | xylose isomerase |
| 2.8 | Cphy1585 | putative solute-binding component of ABC transporter |
| 3.4 | Cphy1586 | ABC transporter related |
| 3.7 | Cphy1587 | Monosaccharide-transporting ATPase |
| 4.6 | Cphy1799 | glycoside hydrolase family 18 |
| 4.8 | Cphy1800 | glycoside hydrolase family 18 |
| 5.0 | Cphy2105 | Endo-1,4-beta-xylanase |
| 2.0 | Cphy2106 | protein of unknown function DUF323 |
| 2.2 | Cphy2128 | Mannan endo-1,4-beta-mannosidase, Cellulose 1,4-beta-cellobiosidases |
| 2.8 | Cphy2569 | extracellular solute-binding protein family 1 |
| 3.7 | Cphy2570 | binding-protein-dependent transport systems inner membrane component |
| 3.5 | Cphy2571 | binding-protein-dependent transport systems inner membrane component |
| 2.1 | Cphy2919 | protein of unknown function DUF1565 |
| 4.4 | Cphy3367 | Cellulose 1,4-beta-cellobiosidase |
| 4.9 | Cphy3368 | Cellulose 1,4-beta-cellobiosidase |
| 2.5 | Cphy3419 | xylulokinase |
| 2.1 | Cphy3854 | glycosyltransferase 36 |
| 2.4 | Cphy3855 | Phosphomannomutase |
| 2.4 | Cphy3858 | extracellular solute-binding protein family 1 |
| 3.4 | Cphy3859 | binding-protein-dependent transport systems inner membrane component |
| 3.4 | Cphy3860 | binding-protein-dependent transport systems inner membrane component |
| 2.6 | Cphy3861 | two component transcriptional regulator, AraC family |

Genes corresponding to transcripts observed to be differentially expressed more than 4-fold during growth yeast extract as compared to growth on glucose are presented in Table 22.

TABLE 22

Expression on Yeast Extract

| Differential Expression (log$_2$) | JGI No. | COG Description |
|---|---|---|
| 2.4 | Cphy0857 | Cellobiose phosphorylase-like protein |
| 2.2 | Cphy0858 | glycoside hydrolase family 30 |
| 3.2 | Cphy0860 | binding-protein-dependent transport systems inner membrane component |
| 3.6 | Cphy0861 | binding-protein-dependent transport systems inner membrane component |
| 3.0 | Cphy1448 | phosphonate ABC transporter |
| 2.0 | Cphy1449 | phosphonate ABC transporter |
| 2.1 | Cphy1450 | phosphonate ABC transporter |
| 2.0 | Cphy1451 | phosphonate ABC transporter |

Example 3

Genomic Dissection of the C. Phytofermentans Genome

Figure 5:
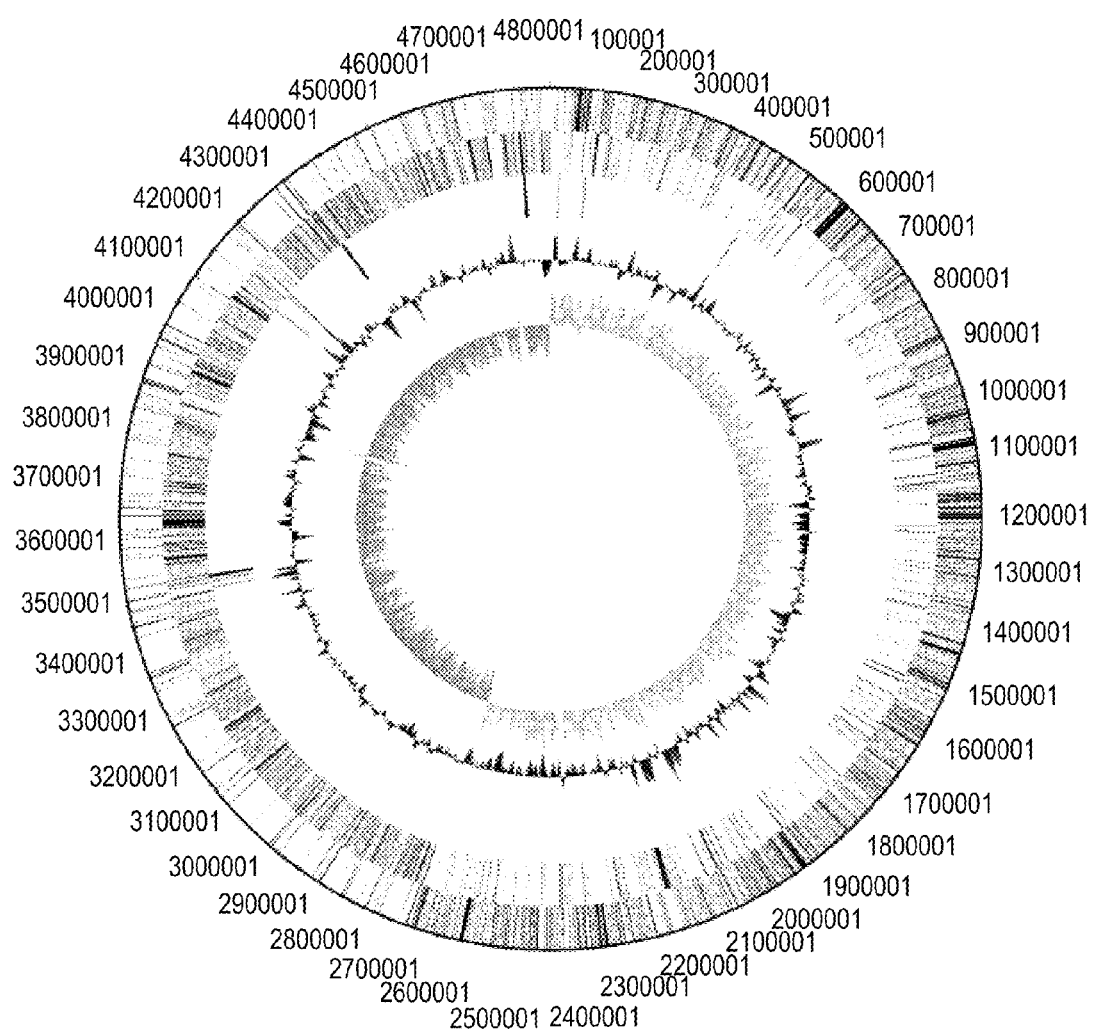
FIG. 5 is a representation of the C. phytofermentans chromosome.

Genome organization. *C. phytofermentans* ISDg ATCC 700394 has a single circular 4,847,594 bp chromosome and harbors no plasmids. The replication origin of the chromosome was defined using the position of the transition point of GC skew and the presence of the characteristic replication protein dnaA (FIG. 5). The G+C content is 35.3%. Plotting the G+C content of 1 kb windows as a function of position in the genome (FIG. 6) reveals several isolated, genomic islands with much higher G+C content. The location of 6 specific islands were defined as 1 kb regions with a mean G+C content >50%, shown in FIG. 6. Genes were identified either in or surrounding each of these genomic islands (Table 23).

TABLE 23

General Features of the Genome of C. phytofermentans

| Parameter | Value |
|---|---|
| Size (bp) | 4,847,594 |
| G + C content (%) | 35.3 |
| Protein coding genes | |
| No. (%) similar to known proteins | 2,870 (73.1) |
| No. (%) similar to proteins of unknown function[a] | 170 (4.3) |
| No. (%) of conserved hypotheticals[b] | 265 (6.7) |
| No. (%) of hypotheticals[c] | 621 (15.8) |
| Total | 3,926 |
| Average ORF size (bp) | 1,009 |
| Coding (%) | 81 |
| No. of rRNA clusters | 8 |
| No. of tRNA genes | 61 |

[a]Unknown function, significant sequence similarity to a named protein to which no specific function is currently attributed.
[b]Conserved hypothetical protein with sequence similarity to a translation of an open reading frame (ORF) in another organism; however no experimental evidence for protein expression exists.
[c]Hypothetical proteins with no significant similarity to any other sequenced gene.

Figure 6:
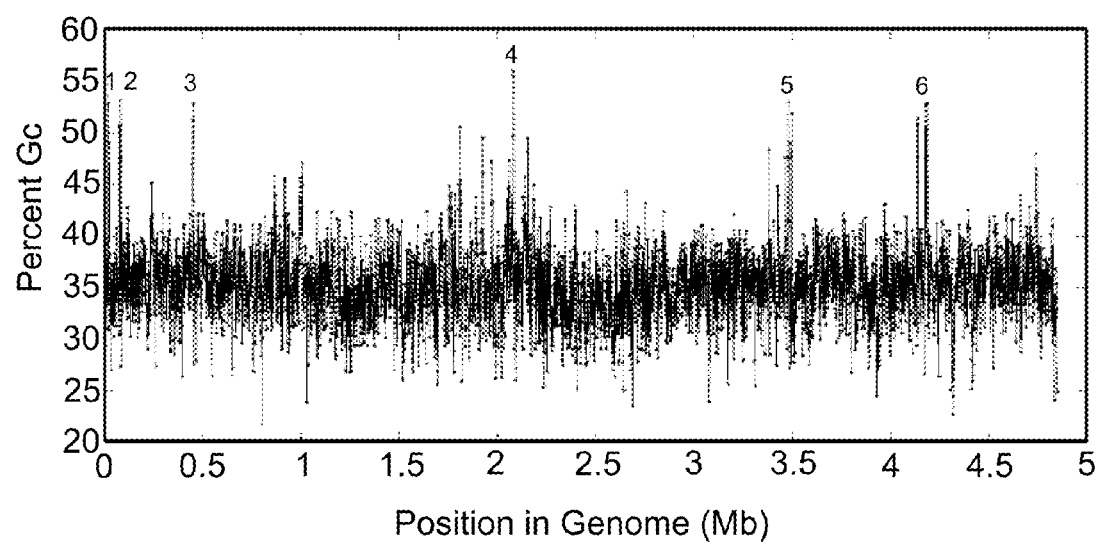
FIG. 6 is a chart showing the GC content of 1 kb genome segments as a function of distance along the C. phytofermentans genome. Six genomic islands with GC contents >50% are numbered. These six regions consist of a total of sixteen 1 kb regions.

Overall, these high G+C islands appear to have low gene density. Of the sixteen 1 Kb regions with a G+C content >50% that compose the 6 genomic islands, 12 of the regions contain no genes. The only genes that are found within the high G+C islands are a two components system (histidine kinase and response regulator) and a protein with a putative collagen triple helix repeat. Most of the genes that surround these high G+C regions are of unknown function. One of the genes adjacent to Region V encodes a phage protein (FIG. 6). The genome encodes 3,926 predicted coding sequences (CDS) (Table 23).

Clostridial genomes typically exhibit strong coding bias, however in *C. phytofermentans* the CDS are encoded equally on the leading (52%) and lagging (48%) strand (Seedorf, H. et al. The genome of *Clostridium* kluyveri, a strict anaerobe with unique metabolic features. *Proc. Natl. Acad. Sci. U.S.A.* 105, 2128-2133 (2008)). Seventy-three percent of the CDS were assigned putative functions, while 11% possessed similarity to genes of unknown function, and 16% were unique to *C. phytofermentans*.

Sixty-one tRNA genes are predicted in the genome covering 20 amino acids (Table 23, Table 24).

TABLE 24 tRNA Genes of C. phytofermentans

| tRNA | Locus | | | | |
|---|---|---|---|---|---|
| Cys | CphyR0019 | | | | 1 |
| His | CphyR0041 | | | | 1 |
| Phe | CphyR0010 | | | | 1 |
| Trp | CphyR0094 | | | | 1 |
| Asn | CphyR0018 | CphyR0030 | | | 2 |
| Asp | CphyR0005 | CphyR0034 | | | 2 |
| Gln | CphyR0042 | CphyR0098 | | | 2 |
| Ile | CphyR0015 | CphyR0069 | | | 2 |
| Tyr | CphyR0008 | CphyR0021 | | | 2 |
| Xaa | CphyR0055 | CphyR0074 | | | 2 |
| Ala | CphyR0016 | CphyR0028 | CphyR0068 | | 3 |
| Pro | CphyR0038 | CphyR0045 | CphyR0083 | | 3 |
| Val | CphyR0006 | CphyR0035 | CphyR0049 | | 3 |
| Arg | CphyR0037 | CphyR0040 | CphyR0073 | CphyR0109 | 4 |
| Glu | CphyR0031 | CphyR0059 | CphyR0060 | CphyR0063 | 4 |
| Lys | CphyR0011 | CphyR0043 | CphyR0107 | CphyR0108 | 4 |
| Met | CphyR0009 | CphyR0020 | CphyR0033 | CphyR0050 | 4 |
| Ser | CphyR0001 | CphyR0024 | CphyR0025 | CphyR0056 | 4 |
| Thr | CphyR0007 | CphyR0032 | CphyR0080 | CphyR0082 | 4 |
| Gly | CphyR0023 | CphyR0039 | CphyR0075 | CphyR0078 | 6 |
| Leu | CphyR0022 | CphyR0036 | CphyR0044 | CphyR0062 | 6 |
| Total | | | | | 61 |

The eight ribosomal operons, of which three are oriented on the leading strand and five on the lagging stand, are clustered in general proximity to the origin of replication (Table 23). The abundance of rRNA operons in *C. phytofermentans* may be an evolutionary adaptation and an advantage to organisms that experience fluctuating growth conditions as suggested by the enhanced capacity for a rapid response to favorable growth conditions for bacteria with higher number of operons (Schmidt, T. M. in *Bacterial genomes: physical structure and analysis*. 221 (Chapman and Hall Co., New York, N.Y., 1997); Klappenbach, J. A., Dunbar, J. M. & Schmidt, T. M. rRNA operon copy number reflects ecological strategies of bacteria. *Appl. Environ. Microbiol.* 66, 1328-1333 (2000); Condon, C., Liveris, D., Squires, C., Schwartz, I. & Squires, C. L. rRNA operon multiplicity in *Escherichia coli* and the physiological implications of rrn inactivation. *J. Bacteriol.* 177, 4152-4156 (1995)).

There appears to be a putative prophage in the genome revealed by the clustered presence of phage-related genes. The phage-cluster spans approximately 39 kb and includes 40 genes (Cphy2953-2993). Fifteen genes, responsible for head and tail structural components and assembly, are homologous to genes in *Clostridium difficile* phage ΦC2 (Goh, S., Ong, P. F., Song, K. P., Riley, T. V. & Chang, B. J. The complete genome sequence of *Clostridium difficile* phage phiC2 and comparisons to phiCD119 and inducible prophages of CD630. *Microbiology* 153, 676-685 (2007)). It is unclear whether the functional equivalent genes necessary for the phage to complete its life cycle, i.e. DNA packaging, tail assembly, cell lysis, lysogeny control and DNA replication, recombination, and modification are present in the genome (Id.). Twenty-seven insertion sequence-related genes (transposases) are present which is lower than in closely related genomes (Table 25).

TABLE 25

| Comparison of Clostridia genomes | | | | | | | |
|---|---|---|---|---|---|---|---|
| | C. phytofermentans | C. bolteae | R. gnavus | R. obeum | C. beijerinckii | C. botulinum | C. perfringens |
| Clostridial cluster | XIVa | XIVa | XIVa | XIVa | I | I | I |
| General chromosome features | | | | | | | |
| Chromosome size, bp | 4,847,594 | 6,556,988 | #### ## | 3,624,708 | 6,000,632 | 3,995,387 | 2,897,393 |
| GC content, % | 35 | 49 | 42 | 41 | 29 | 28 | 28 |
| Coding, % | 81 | 91 | 92 | 90 | 79 | 81 | 80 |
| Protein coding genes | 3,926 | 7,284 | 3,913 | 4,175 | 5,020 | 3,572 | 3,635 |
| Transposases (COG0675, pfam01548, pfam02371) | 27 | 77 | 61 | 50 | 42 | 1 | 93 |
| Glycoside hydrolases[a] | 109 | na | na | na | 75 | 23 | 38 |
| Glycoside hydrolase families[a] | 39 | na | na | na | 25 | 10 | 21 |
| Solute binding proteins (pfam01547) | 21 | 30 | 9 | 8 | 11 | 4 | 7 |
| Polysaccharide ABC transporters (Lplb COG4209) | 20 | 0 | 2 | 0 | 1 | 0 | 1 |
| Xylose ABC transporters (xylF PRK10355) | 9 | 32 | 8 | 13 | 35 | 3 | 3 |
| PurR (COG1609) | 23 | 42 | 18 | 15 | 20 | 6 | 15 |
| AraC (pfam00165) | 70 | 66 | 33 | 28 | 48 | 21 | 10 |
| AraC + CheY (COG4753) | 18 | 34 | 11 | 11 | 8 | 1 | 2 |

| | C. cellulolyticum | C. thermocellum | Caldicellulosiruptor saccharolyticus | Thermoanaerobacter ethanolicus |
|---|---|---|---|---|
| Clostridial cluster | III | III | X | V |
| General chromosome features | | | | |
| Chromosome size, bp | 3,958,683 | 3,843,301 | 2,970,275 | 2,362,816 |
| GC content, % | 37 | 38 | 35 | 34 |
| Coding, % | 86 | 83 | 86 | 86 |
| Protein coding genes | 3,283 | 3,189 | 2,679 | 2,243 |
| Transposases (COG0675, pfam01548, pfam02371) | 100 | 139 | 106 | 56 |
| Glycoside hydrolases[a] | na | 70 | 61 | 15 |
| Glycoside hydrolase families[a] | na | 23 | 31 | 26 |
| Solute binding proteins (pfam01547) | 11 | 5 | 18 | 8 |
| Polysaccharide ABC transporters (Lplb COG4209) | 6 | 0 | 7 | 0 |
| Xylose ABC transporters (xylF PRK10355) | 6 | 2 | 3 | 3 |
| PurR (COG1609) | 11 | 8 | 11 | 12 |
| AraC (pfam00165) | 35 | 9 | 19 | 1 |
| AraC + CheY (COG4753) | 12 | 2 | 13 | 0 |

[a]www.CAZy.org

Figure 7:
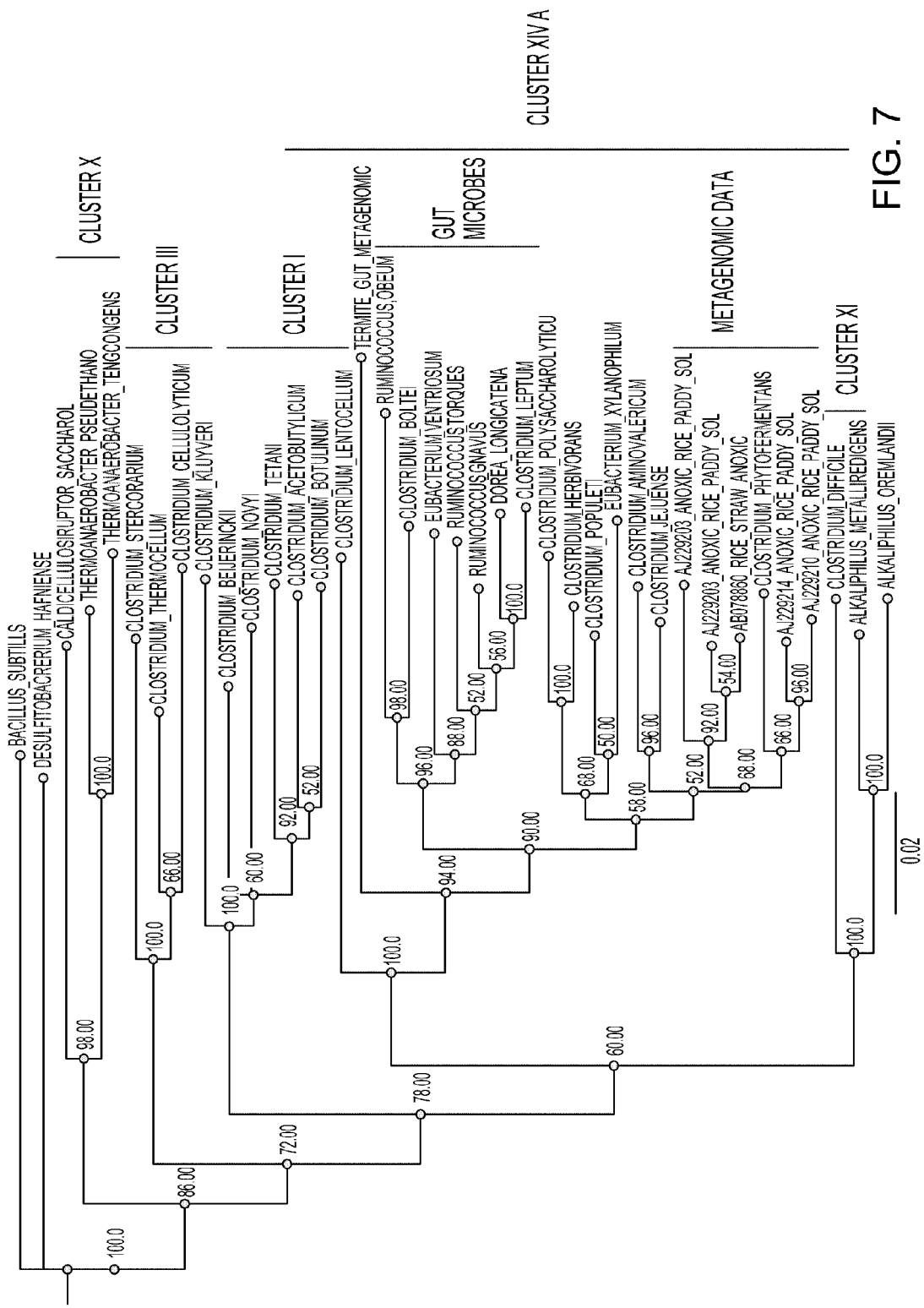
FIG. 7 is a neighbor-joining tree of strain C. phytofermentans and related taxa within the class Clostridia based on 16S rRNA gene sequences. Cluster I comprises disease causing Clostridia, cluster III comprises cellulolytic Clostridia and cluster XIVa comprises gut microbes and metagenomic sequences are in the genus Clostridium. Numbers at nodes are levels of bootstrap support (percentages) based on neighbour-joining analyses of 1000 resampled datasets. Bacillus subtilis was used as an outgroup. Bar, 4 nucleotide substitutions per position

*C. phytofermentans* is evolutionarily related to plant litter-associated soil microbes. To elucidate the phylogenetic relationship between *C. phytofermentans* and other members of the class Clostridia including non-sequenced genomes, 16S rRNA gene sequences (1,611 bp) of the isolate and most closely-related members were used for neighbor-joining analysis. The phylogeny confirmed that strain ISDg is a member of cluster XIVa composed of a majority of the human/rat/chicken gut microbes, and only distantly related to cluster I, containing many pathogens and the solventogenic *Clostridium acetobutylicum*, and cluster III, containing cellulolytic bacteria such as *Clostridium cellulolyticum* and *Clostridium thermocellum* (FIG. 7) (Warnick, T. A., Methe, B. A. & Leschine, S. B. *Clostridium phytofermentans* sp. nov., a cellulolytic mesophile from forest soil. *Int. J. Syst. Evol. Microbiol.* 52, 1155-1160 (2002); Collins, M. D. et al. The phylogeny of the genus *Clostridium*: proposal of five new genera and eleven new species combinations. *Int. J. Syst. Bacteriol.* 44, 812-826 (1994)). Within Cluster XIVa, *C. phytofermentans* is part of a clade containing uncultured bacteria derived from metagenomic analyses from anoxic rice paddy soil, methanogenic landfill leachate bioreactor (93.7-93.8% similarity) (Burrell, P. C., O'Sullivan, C., Song, H., Clarke, W. P. & Blackall, L. L. Identification, detection, and spatial resolution of *Clostridium* populations responsible for cellulose degradation in a methanogenic landfill leachate bioreactor. *Appl. Environ. Microbiol.* 70, 2414-2419 (2004); Hengstmann, U., Chin, K. J., Janssen, P. H. & Liesack, W. Comparative phylogenetic assignment of environmental sequences of genes encoding 16S rRNA and numerically abundant culturable bacteria from an anoxic rice paddy soil. Appl. Environ. Microbiol. 65, 5050-5058 (1999)), the species *Clostridium aminovalericum* (92.4% similarity) and *Clostridium jejuense* (92.2% similarity), divergent from the gut microbes clade (89.7% similarity) (FIG. 7).

Figure 8:
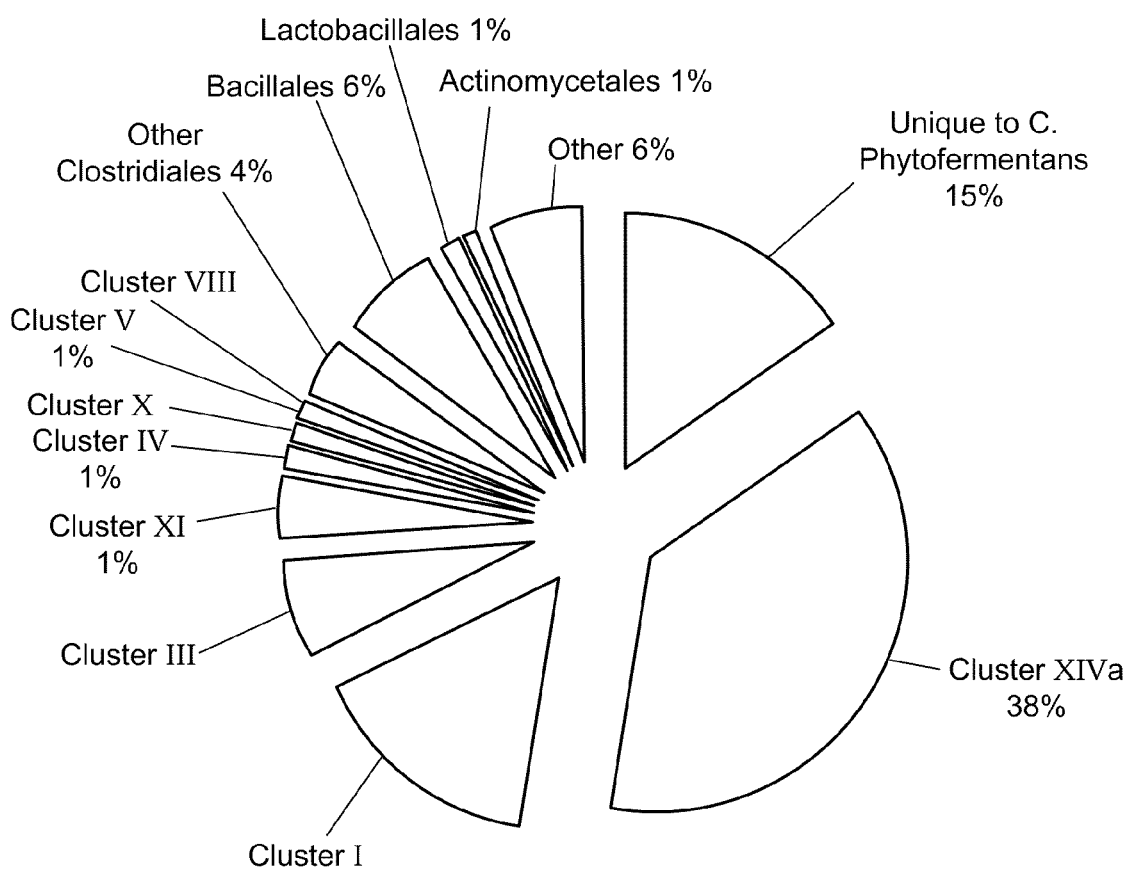
FIG. 8 is a circle graph showing the number of best matches (e-value cutoff of 0.01) of Clostridium phytofermentans ISDg CDSs in other sequenced bacterial genomes in the class Clostridia.

The grouping of *C. phytofermentans* within the class Clostridia based on rRNA analysis is consistent with the overall distribution of CDS *C. phytofermentans* genes according to their similarity to genes in other completely sequenced genomes using BLASTP. Thirty-eight percent of CDS were most similar to cluster XIVa, followed by 10% in cluster 1 and 7% in cluster III (FIG. 8). A significant proportion of the CDS (14%), however had no obvious homology in the class Clostridia and exhibited the highest level of similarity to CDS in phylogenetically distant strains. This suggests that the *C. phytofermentans* genome may contain many genes acquired by horizontal gene transfer. These scattered origins in genes underline the heterogeneity of the genus *Clostridium* and the uniqueness of *C. phytofermentans* among sequenced genomes.

Assembly of a unique set of GH from diverse origins. The simultaneous presence of glycoside hydrolases (GHs) with such a vast array of functions in a single genome such as *C. phytofermentans* is remarkable. Despite the organizational diversity of microbial systems for polysaccharide utilization, the basic building blocks show considerable uniformity. The catalytic domains that are found in polysaccharide-degrading enzymes can be organized into families by their primary sequences and folding topologies. Representative of these families can be found among many diverse bacteria and eukaryotic microorganisms. By quantifying the similarities or differences in the GH catalytic domains of other bacteria as well as their organization from gene to genome level, we seek to better understand their function or gage the uniqueness of *C. phytofermentans*.

Figure 9A:
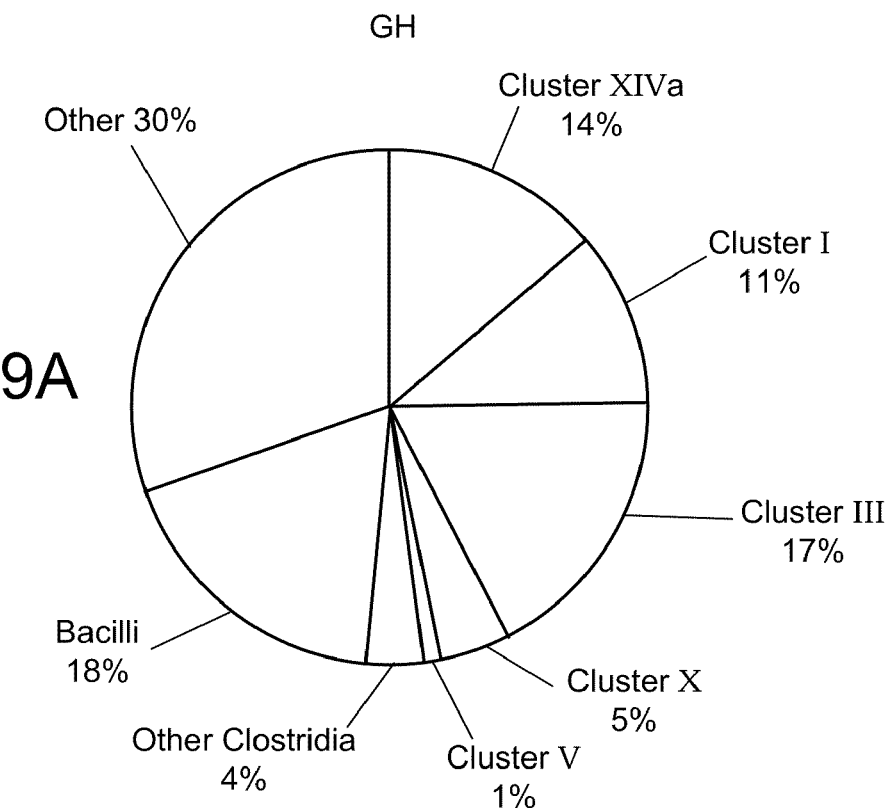
FIGS. 9A and 9B are circle graphs showing a comparison of Glycoside Hydrolase (GH) encoding genes (9A) and all genes in different organisms (9B) using BLASTP.
Figure 9B:
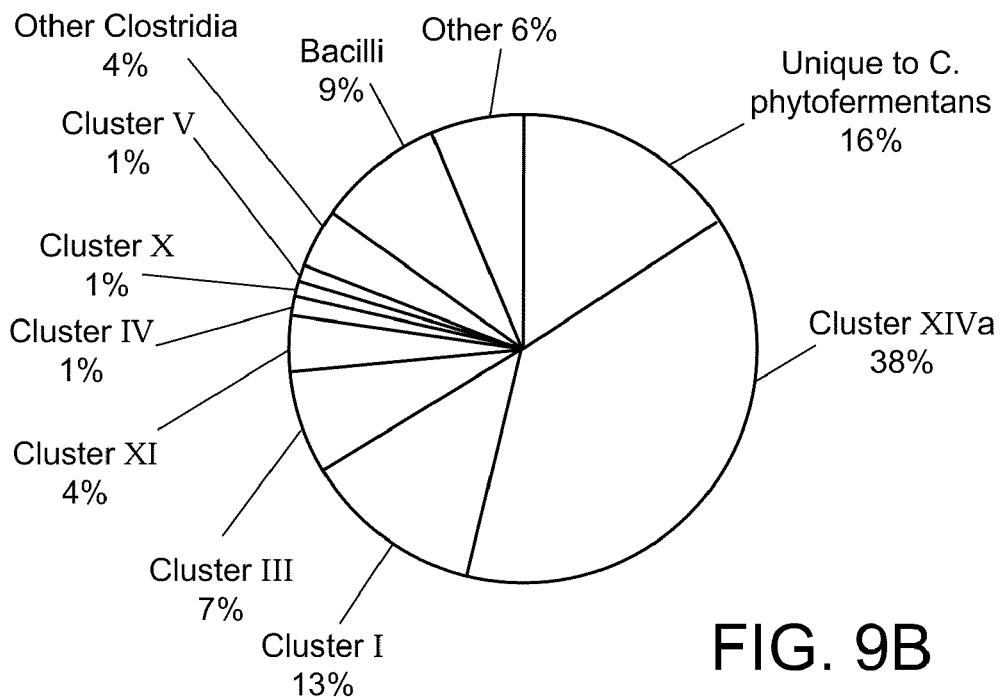

When compared to enzymes in other sequenced bacteria using BLASTP, GH of *C. phytofermentans* are similar to a broad diversity of bacteria representing six phyla and 46 species. There are more GH genes similar to distantly related bacteria than expected from the distribution of all the genes in *C. phytofermentans*, (chi square test, P=0.0004998) (FIG. 9). About 50% of the GH compared to the expected 14%, are more similar to species outside the class Clostridia (FIG. 9). About 18% of the GH were more similar to Bacilli, followed by 17% more similar to cluster III of cellulolytic bacteria (FIG. 9). This suggests that horizontal gene transfer played a key role in the evolution of plant degradative abilities in *C. phytofermentans* and the assembly of a unique set of GH from very different origins.

With the exception of starch-degradation genes clustered on the genome (Cphy2304-2352), overall, there is very little co-localization of hemicellulase or cellulase genes. This supports the hypothesis that the latter where acquired through independent horizontal gene transfer. However an example of tandem of genes with related function is a xylan-degrading cluster with a beta-glucosidase Cphy3009 (GH3), an endo-xylanase Cphy3010 (GH10) and an arabinofuranosidase Cphy3011 (GH43). This tandem appears to be unique to *C. phytofermentans*. Furthermore, the genes encoding the two main cellulases, Cphy3367 (GH9) and Cphy3368 (GH48) are contiguous on the genome. This is consistent with the high synergism observed between bacterial cellulases GH48 and GH9, present in all cellulase enzyme systems known so far in bacteria (Riedel, K., Ritter, J. & Bronnenmeier, K. Synergistic interaction of the *Clostridium stercorarium* cellulases Avicelase I (CelZ) and Avicelase II (CelY) in the degradation of microcrystalline cellulose. *FEMS Microbiol. Lett.* 147, 239 (1997)).

In the molecular phylogeny, the catalytic domain GH9 and GH48 of *C. phytofermentans* (see FIGS. 10 and 11) are most similar to the endoglucanase Z precursor (Avicelase I) (Jauris, S. et al. Sequence analysis of the *Clostridium stercorarium* celZ gene encoding a thermoactive cellulase (Avicelase I): identification of catalytic and cellulose-binding domains. *Mol. Gen. Genet.* 223, 258-267 (1990)) and cellodextrinohydrolase (Avicelase II) respectively (Bronnenmeier, K., Rucknagel, K. P. & Staudenbauer, W. L. Purification and properties of a novel type of exo-1,4-beta-glucanase (avicelase II) from the cellulolytic thermophile *Clostridium stercorarium*. *Eur. J. Biochem.* 200, 379-385 (1991)) from the thermophilic cellulolytic and xynalolytic *Clostridium stercorarium*. In *C. stercorarium*, GH9 and GH48 are also adjacent (Schwarz, W. H., Zverlov, V. V. & Bahl, H. Extracellular glycosyl hydrolases from clostridia. *Adv. Appl. Microbiol.* 56, 215-261 (2004)). This is even more extreme in the thermophilic *C. saccharolyticus*, where GH9 and GH48 are highly similar to those of *C. phytofermentans* and *C. stercorarium*, and are fused into a single protein. These observations suggest a common origin and synergistic functioning of these key enzymes in these three bacteria.

Figure 11A:
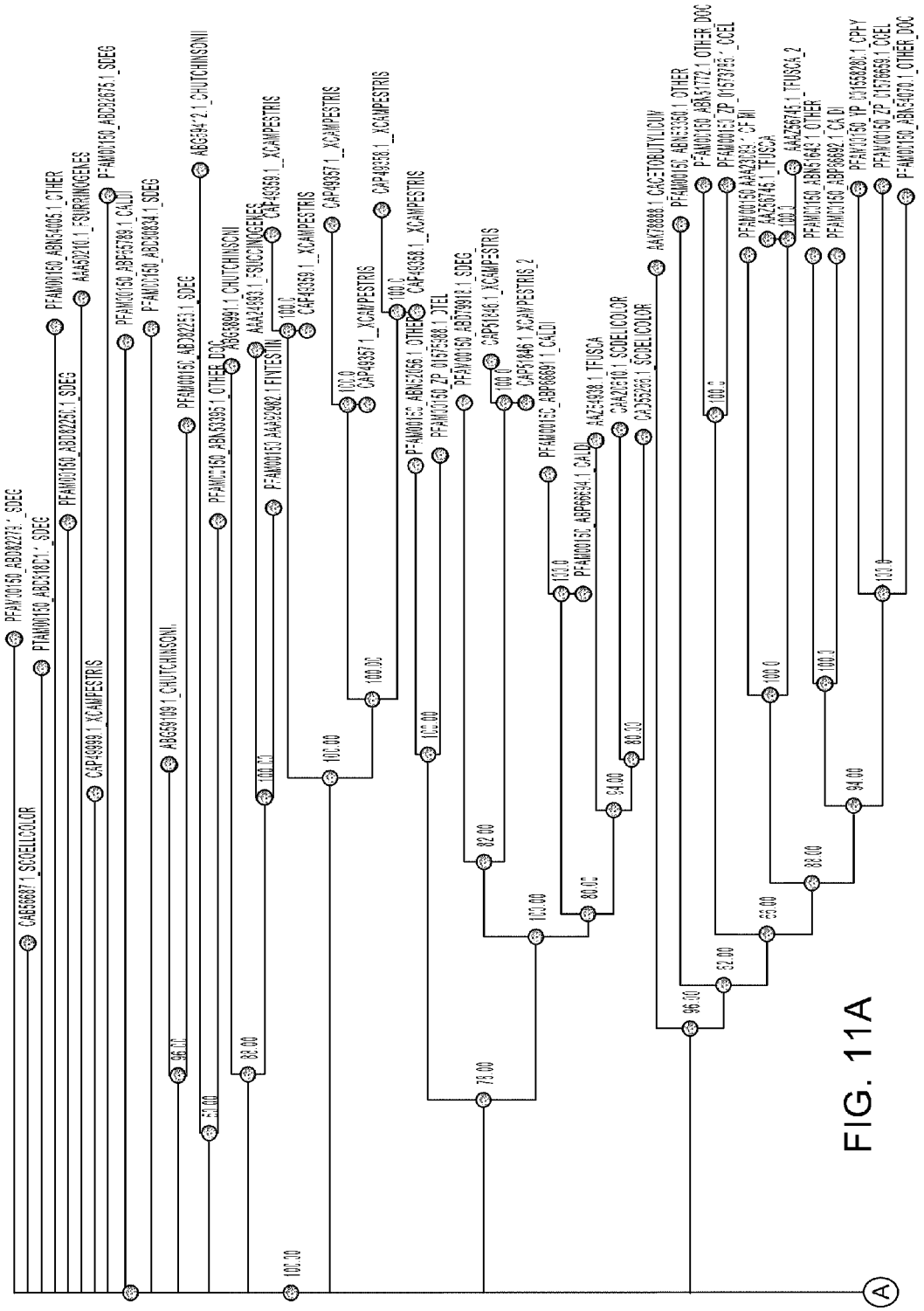
FIG. 11 is a neighbor-joining tree showing molecular phylogeny of glycoside hydrolase family GH5 domains.
Figure 11B:
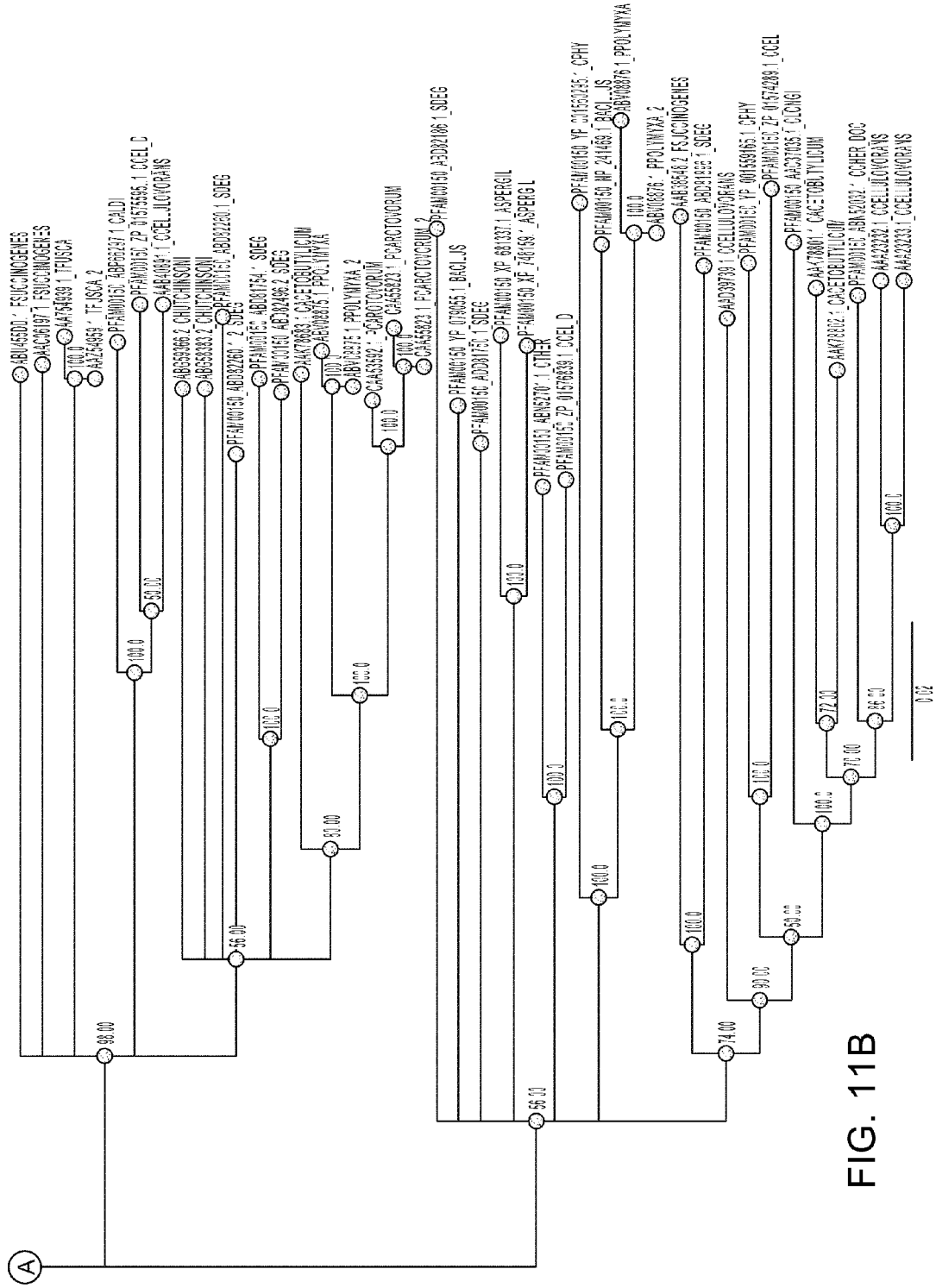

Since a given GH family contains enzymes with a very broad range of known activities, one might ask whether redundancy in a family reflects redundancy in function or a lack of specificity of the catalytic domain. More detailed molecular studies of GH families of interest for plant cell wall degradation show that there is often variation in the sequences of these related but not identical genes. It should be mentioned that compared to the cellulosic specialist *C. thermocellum* with an outstanding number of GH9 (16), GH48 (2), GH5 (11) cellulases reflecting its specialization in degrading cellulose, *C. phytofermentans* overall has less redundancy per family but a broader range of GH families which reflect its more generalist ecology (FIG. 9). Nevertheless some GH families in *C. phytofermentans* still contain a significant number of genes. This is the case of the GH3 glucosidases, GH5 cellulases, and GH10, GH26, GH43 xylan-degrading enzymes. The molecular phylogeny of the GH5 cellulases (pfam00150) from *C. phytofermentans* revealed that they are diverse, separated into 2 subclusters (FIG. 11). Cluster B contains fungal cellulases. This example reinforces how lateral gene transfer has impacted the evolution of GH. More particularly, it emphasizes the importance of gene transfer between microorganims that belong to different kingdoms which conjectures an even more important role of gene transfer within kingdoms. The phylogeny of the 6 GH10 domains of *C. phytofermentans* suggest a wide range of variability and probably function in *C. phytofermentans*. Cphy2108 (GH10) is very similar to the multimodular xylanase of *C. stercorarium* Xyn10C, a thermostable cell-bound and cellulose and xylan-binding protein, thus binding the cell to the substrate (Ali, M. K., Kimura, T., Sakka, K. & Ohmiya, K. The multidomain xylanase Xyn10B as a cellulose-binding protein in *Clostridium stercorarium. FEMS Microbiol. Lett.* 198, 79-83 (2001)). Two unique but closely related GH10 domains are found on a single enzyme merged to a CE domain suggesting a duplication event followed by fusion and divergence. This specific arrangement of catalytic function on a single protein is unique to *C. phytofermentans*.

Duplications, followed by fusions and rearrangement, and sequence divergence generated an enormous array of multimodular enzymes in *C. phytofermentans* that vary in their substrate specificities and kinetic properties. But overall, the striking feature of *C. phytofermentans* is the importance of horizontal gene transfer that allowed the acquisition of such a complex array of genes, and gene clusters, from other members of the niche community.

Plant cell wall degradation without a cellulosome. *C. phytofermentans* shares a similar ecology with cellulosome-producing bacteria. However, there is neither biochemical nor genetic evidence (no dockerin, cohesin, or anchorin domains) for the production of cellulosomes in this bacterium. Cellulosome complexes are believed to be involved for plant cell wall breakdown as they provide a bacterial cell-surface mechanism for the withholding of a high concentration of proteins that represent the array of substrate specificities that are necessary for cleaving various linkages in plant cell wall polysacchacharides; they potentially maximize the stoichiometry and the synergy between different enzyme catalytic and binding specificities; and they might help to limit the diffusion of breakdown products away from the cell by providing a special environment between the cell membrane and the substrate (Flint, H. J., Bayer, E. A., Rincon, M. T., Lamed, R. & White, B. A. Polysaccharide utilization by gut bacteria: potential for new insights from genomic analysis. *Nat. Rev. Microbiol.* 6, 121-131 (2008)). The strategy that *C. phytofermentans* employs for an efficient breakdown of plant cell wall and uptake of product without a cellulosome is unclear.

Figure 10:
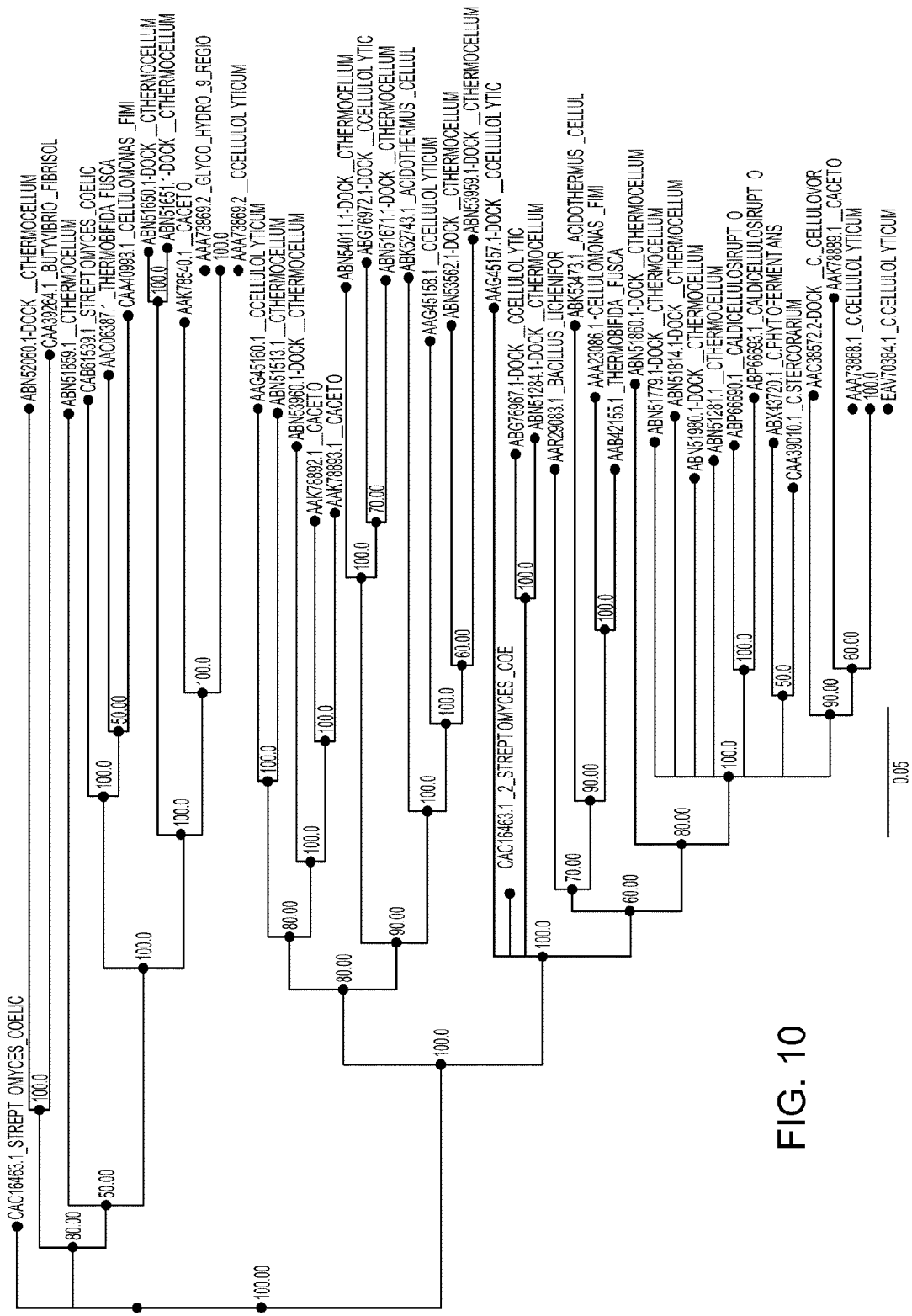
FIG. 10 is a neighbor-joining tree showing molecular phylogeny of glycoside hydrolase family GH9 domains.

First, it is surprising that for all cellulases GH5, GH9 and GH48, there is no grouping in the phylogenetic trees according to the affiliation of the protein to a cellulosome. This suggests that either the dockerin domain anchoring the protein in the complex was lost or was acquired many times independently (FIGS. 10 and 11). The striking multimodular feature of cellulosomal proteins where multiple domains from diverse families of GH, CE, PL and carbohydrate-binding module (CBM) are merged on a single protein is preserved in *C. phytofermentans*. *C. phytofermentans* has 19 modular GH proteins, representing about 17% of all GH. In non-cellulolytic bacteria, the corresponding GH are found mainly on single-domain polypeptides (Flint, H. J., Bayer, E. A., Rincon, M. T., Lamed, R. & White, B. A. Polysaccharide utilization by gut bacteria: potential for new insights from genomic analysis. *Nat. Rev. Microbiol.* 6, 121-131 (2008)). This might reflect the different cellular location of the gene products, and the fact that they act on smaller, soluble carbohydrate substrates (Id.). According to this hypothesis, the multi-modular organization that seems to be characteristic of enzymes from cellulolytic species might be preserved primarily for the extracellular processing of heterogeneous insoluble substrates, such as plant cell walls (Id.).

In the absence of a cellulosome, CBM could fix the enzymes firmly to the plant cell wall and thus keep them in the vicinity of their substrate. Thirty-five putative CBM representing 15 CAZy families were identified (Table 5). CBM2, CBM3, CBM4, CBM6 and CBM46 have been shown to bind cellulose (Table 5). CBM2, CBM4, CBM6, CBM13, CBM22, CBM35, and CBM36 have been demonstrated to bind xylan (Table 5). The presence of various combinations of CBM domains with specificity that does not match the specificity of the catalytic domain might give an advantage for an action on different topologies of the plant cell wall where multiple polysaccharide types are cross-linked. The xylanases with cellulose-binding CBM might help *C. phytofermentans* to attach to cellulose fibers while degrading the cross-linked xylan. The presence of CBMs independent of catalytic domains might also be explained by their thermostabilizing action that has been shown in some cases. Another type of domain, X2, can be found between the catalytic and CBM domains or between the CBM domains in one mannanase and three cellulases in *C. phytofermentans* (Table 6). Very little information is available on the function of X2 in extracellular enzymes of bacteria. It can be postulated that they serve as spacers or linkers allowing optimal interaction between the catalytic and substrate-binding modules, for protein-protein interaction or as a potential carbohydrate-binding domain.

In addition to binding to polysaccharide, some enzymes seem to be cell-bound allowing the cell to stay close to its substrate. Among the 31 GH enzymes that are predicted to be secreted (predicted to have a signal peptide and/or extracellular), the recurrent prediction of transmembrane helices, TonB box (COG0810 and PS00430), SORT domain and/or cell-wall binding suggest that these enzymes might associate with the membrane or the cell wall (Table 6). Among these proteins, 8 GH enzymes are predicted to have both CBM and cell attaching ability to potentially achieve physical proximity of the cell to their degraded substrate. Finally, the peculiar gene Cphy1775 (SLH-GH*-CBM32-CBM32) was matched to a predicted SLH domain (pfam00395) for anchoring it to the cell wall and also two immunoglobulin-like fold (CBM32) and may behave like a CBM domain, which bind the cell to its substrate. Other GH enzymes might still be anchored to the cell surface by other unknown mechanisms. Cells might adhere together through different domains such as pfam07705 (CARDB, cell adhesion domain in bacteria) and pfam01391 (Collagen, Collagen triple helix repeat). Biofilm formation might also play a role in the orchestration of the degradation of the plant cell wall polysaccharides.

Degradation coupled with uptake and phosphorylation by a wide range of inducible ABC-transporters. Although one phosphoenolpyruvate (PEP)-dependent phosphotransferase system was found in the genome, preliminary expression profile data suggests it may not be expressed when cells are grown on any of the main components of plant cell walls such as xylan, cellulose, cellobiose, or glucose. Rather, the remarkable number (137) of proteins with ABC_tran (pfam00005) domain in the genome is consistent with carbohydrate uptake via ATP-binding cassette (ABC)-transporters.

Consistently, compared to its relatives within the class Clostridia (Table 25), *C. phytofermentans* has an unusually high number (21) of solute-binding domains (SBP_bac_1, pfam01547), typically associated with uptake ABC-transporters and allowing the specific binding of different solutes. This suggests a necessity for affinity to various types of solutes, which is consistent with the hypothesis that *C. phytofermentans* can uptake various oligosaccharides. Finally, polysaccharides ABC-transporters Lplb (COG4209) domain, a subcomponent permease type of some ABC-transporters are overrepresented (20) in *C. phytofermentans* compared to other bacteria in the class Clostridia (Table 25).

The number and variety of this domain might allow the uptake of a wide range of oligosaccharides (Table 25). That *C. phytofermentans* has 0.5% of its genes dedicated to this function, while *C. saccharolyticus*, which is also a generalist, has only 0.2% suggesting that *C. saccharolyticus* uptakes more uniform types of saccharides. Another striking features is the presence of GH (53 out of 109) adjacent to 41 ABC-type transporters, together with regulators which suggests coupled uptake and degradation as well as specific regulation (Table 7). The outstanding number and variety of GH94 (cellobiose phosphorylase/cellodextrin phosphorylase) and GH65 (maltose phosphorylase) (Table 25) is consistent with the hypothesis that a wide range of oligosaccharide types enter the cell. The presence of 4 out of 5 cellobiose/cellodextrin phosphorylases GH94 membrane-bound proteins next to an ABC transporter are consistent with cellobiose and cellodextrin transport via an ABC protein which is also the case for *C. cellulolyticum* (Desvaux, M., Guedon, E. & Petitdemange, H. Cellulose catabolism by *Clostridium cellulolyticum* growing in batch culture on defined medium. *Appl. Environ. Microbiol.* 66, 2461-2470 (2000)).

There is also a high number of beta-glucosidases (8 GH3) that can have activity against cellobiose or xylobiose. *C. phytofermentans* might feed the oligosaccharides into its catabolism by energetically favorable phosphorylation through the cellobiose/cellodextrin phosphorylase or by energy-wasting hydrolytic beta-glucosidase action. It is likely that the concentration of cellodextrins and the availability of other growth substrates (e.g., cellulose or cellobiose) are involved in determining the destiny of cellodextrins as well as the relative importance of phosphorolytic and hydrolytic cleavage. Given the widespread occurrence of phosphorolytic and hydrolytic routes for cellodextrin metabolism in cellulolytic microorganisms, it is possible that this apparent redundancy is of selective value. Regulating the relative flux via these two pathways may allow the microbe to adjust the rate of ATP in response to environmental factors (e.g., availability of substrate). *C. phytofermentans* is also able to uptake monosaccharides such as xylose, witnessed by the presence of 9 XylF, predicted to take up xylose (Table 25).

Finely tuned regulation of carbohydrate metabolism. Compared to relatives in Clostridia, *C. phytofermentans* has an abundance of AraC (70) and PurR (23) transcriptional regulators (Table 25). Prokaryotic transcriptional regulators are classified in families on the basis of sequence similarity and structural and functional criteria. AraC regulators typically activate transcription of genes involved in carbon metabolism, stress response and pathogenesis (Ramos, J. L. et al., "The TetR family of transcriptional repressors," *Microbiol. Mol. Biol. Rev.* 69, 326-356 (2005)). PurR belongs to the lactose repressor family (lac) and the gene product usually acts as a repressor, where physiological concentrations of ligand cause dissociation of the PurR-DNA complex (Id.). The abundance of these regulators is consistent with a wide variety of substrate utilization and a complex network of regulation.

Of the 23 genes that have significant similarity to PurR, 8 are adjacent to ABC transporters clustered with GH enzymes. Among the 70 genes that have significant similarity to AraC, 20 are found close to ABC transporters clustered to GH enzymes. Among the 41 ABC-transporters found clustered with GH enzymes, 20 are adjacent to one AraC and 8 are close to PurR. Based on these observations, we hypothesize that they regulate the expression of the respective genomic regions (Table 7).

Example 4

Testing Hydrolase Activity

A variety of methods to test the biological activity of a predicted hydrolase can be utilized. In one example, a predicted gene identified in *C. phytofermentans* encoding a hydrolase is isolated and cloned into an expression vector. The expression vector is transformed into a microorganism, for example, *E. coli*. Activity of the expressed gene is measured by supplying the transformed microorganism with the substrate of the predicted hydrolase and measuring depletion of the substrate and increase in products of hydrolyis, and comparing the level of this activity to the activity in an untransformed control microorganism. In some experiments, the expression vector is designed for the extracellular expression of the predicted hydrolase. An increase in hydrolysis of the substrate can indicate that the predicted hydrolase is in fact a hydrolase.

Example 5

Testing ABC-Transporter Activity

A variety of methods to test the biological activity of a predicted ABC-transporter can be utilized. In one example, a predicted gene or genes identified in *C. phytofermentans* encoding an ABC-transporter is isolated and cloned into an expression vector. The expression vector is transformed into a microorganism, for example, *E. coli*. Activity of the expressed gene is measured by supplying the transformed microorganism with the substrate of the predicted ABC-transporter and measuring transport of the substrate into the cell, and comparing the level of this uptake to the uptake in an untransformed control microorganism. An increase in uptake can indicate that the predicted ABC-transporter is an ABC-transporter.

Example 6

Testing Transcriptional Regulator Activity

A variety of methods to test the biological activity of a predicted transcriptional regulator can be utilized. In one example, a predicted gene identified in *C. phytofermentans* encoding a transcriptional regulator is isolated and cloned into an expression vector. The expression vector is transformed into a microorganism, for example, *E. coli*. Activity of the expressed gene is measured by co-transfecting the transformed organism with a plasmid containing a target nucleotide sequence for the transcriptional regulator and a reporter gene. The activity of the reporter gene is measured and compared to the level of activity of the same reporter gene in a control microorganism. An increase in reporter gene activity indicates that the predicted transcriptional regulator may be a transcriptional regulator.

Example 7

Engineering of Cellobiose Utilization in *E. coli*

Most lab strains and natural isolates of *E. coli* do not express functional genes for cellobiose utilization, although they do typically contain cryptic cellobiose utilization genes on their chromosomes (Hall et al., J. Bacteriol., 1987 June; 169: 2713-2717). *E. coli* are engineered to utilize cellobiose by expression of Cphy2464-2466, encoding an ABC transporter and Cphy0430, encoding a cellobiose phsophorylase that converts cellobiose into glucose and glucose-1-phosphate. The Cphy2464-2466 and Cphy0430 genes are expressed from a constitutive promoter on a plasmid. The signal sequence of Cphy2466 is replaced with the signal sequence of an endogenous *E. coli* ABC transporter periplasmic binding protein to direct expression of the protein in the periplasm. The engineered *E. coli* are able to grow using cellobiose as a sole carbon source.

Example 8

Engineering of Improved Pectin Breakdown in *S. cerevisiae*

Cphy1714, Cphy1720, and Cphy3586 are cloned an *E. coli*—*S. cerevisiae* shuttle vector and expressed heterologously from the plasmid in *S. cerevisiae*. To enable secretion of the gene products, signal sequences are replaced by signal sequences from *S. cerevisiae* proteins. The engineered yeast display improved pectinolysis.

Example 9

Microorganism Modification pIMPCphy

Figure 18:
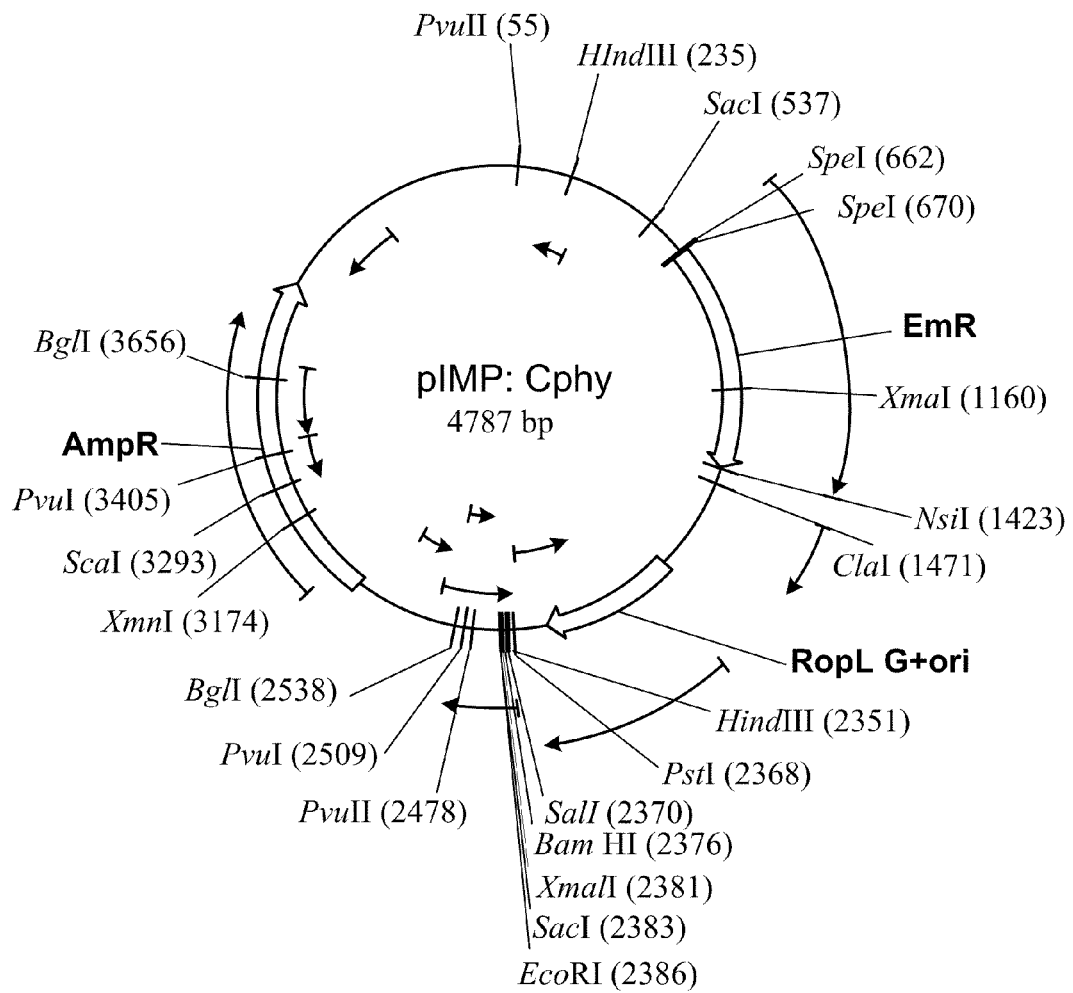
FIG. 18 is a depiction of a plasmid map for pIMP-Cphy.

The vector pIMPCphy was constructed as a shuttle vector for *C. phytofermentans*. It has an Ampicillin resistance cassette and an Origin of Replication (ori) for selection and replication in *E. coli*. It contains a Gram-positive origin of replication that allows the replication of the plasmid in *C. phytofermentans*. To select for the presence of the plasmid, the pIMPCphy vector carries a gene for erythromycin resistance under the control of the *C. phytofermentans* promoter of the gene Cphy1029. This plasmid is transferred to *C. phytofermentans* by electroporation or by transconjugation with an *E. coli* strain that has a mobilizing plasmid, for example pRK2030. A plasmid map of pIMPCphy is depicted in FIG. 18.

Constitutive Promoter

In a first step, several promoters from *C. phytofermentans* were chosen that show high expression of their corresponding genes in all growth stages as well as on different substrates. A promoter element can be selected by selecting key genes that would necessarily be involved in constitutive pathways (e.g., ribosomal genes, or for ethanol production, alcohol dehydrogenase genes). Examples of promoters from such genes include, but are not limited to:

Cphy__1029: iron-containing alcohol dehydrogenase
Cphy__3510: Ig domain-containing protein
Cphy__3925: bifunctional acetaldehyde-CoA/alcohol dehydrogenase Cloning of Promoter The different promoters in the upstream regions of the genes were amplified by PCR. The primers for this PCR reaction were chosen in a way that they include the promoter region, but do not include the ribosome binding sites of the downstream gene. The primers were designed to introduce restriction sites at the end of the promoter fragments that are present in the multiple cloning site of pIMPCphy, but are otherwise not present in the promoter region itself, for example SalI, BamHI, XmaI, SmaI, EcoRI.

The PCR reaction was performed with a commercially available PCR Kit, GoTaq™ Green Master Mix (Promega), according to the manufacturer's conditions. The reaction was run in a thermal cycler, Gene Amp System 24 (Perkin Elmer). The PCR products were purified with the GenElute™ PCR Clean-Up Kit (Sigma). Both the purified PCR products as well as the plasmid pIMPCphy were then digested with the corresponding enzymes with the appropriate amounts according to the manufacturer's conditions (restriction enzymes from New England Biolabs and Promega). The PCR products and the plasmid were then analyzed and gel-purified on a Recovery FlashGel™ (Lonza). The PCR products were subsequently ligated to the plasmid with the Quick Ligation Kit (New England Biolabs) and competent cells of *E. coli* (DH5α) are transformed with the ligation mixtures and plated on LB plates with 1 µg/ml ampicillin. The plates are incubated overnight at 37° C.

Ampicillin resistant *E. coli* colonies were picked from the plates and restreaked on new selective plates. After growth at 37° C., liquid LB medium with 1 µg/ml ampicillin was inoculated with a single colony and grown overnight at 37° C. Plasmids were isolated from the liquid culture with the Gene Elute Plasmid isolation kit.

Miniprep Kit

Plasmids were checked for the right insert by PCR reaction and restriction digest with the appropriate primers and by restriction enzymes respectively. To ensure the sequence integrity, the insert is sequenced at this step.

Cloning of Cellulase Genes

Figure 19:
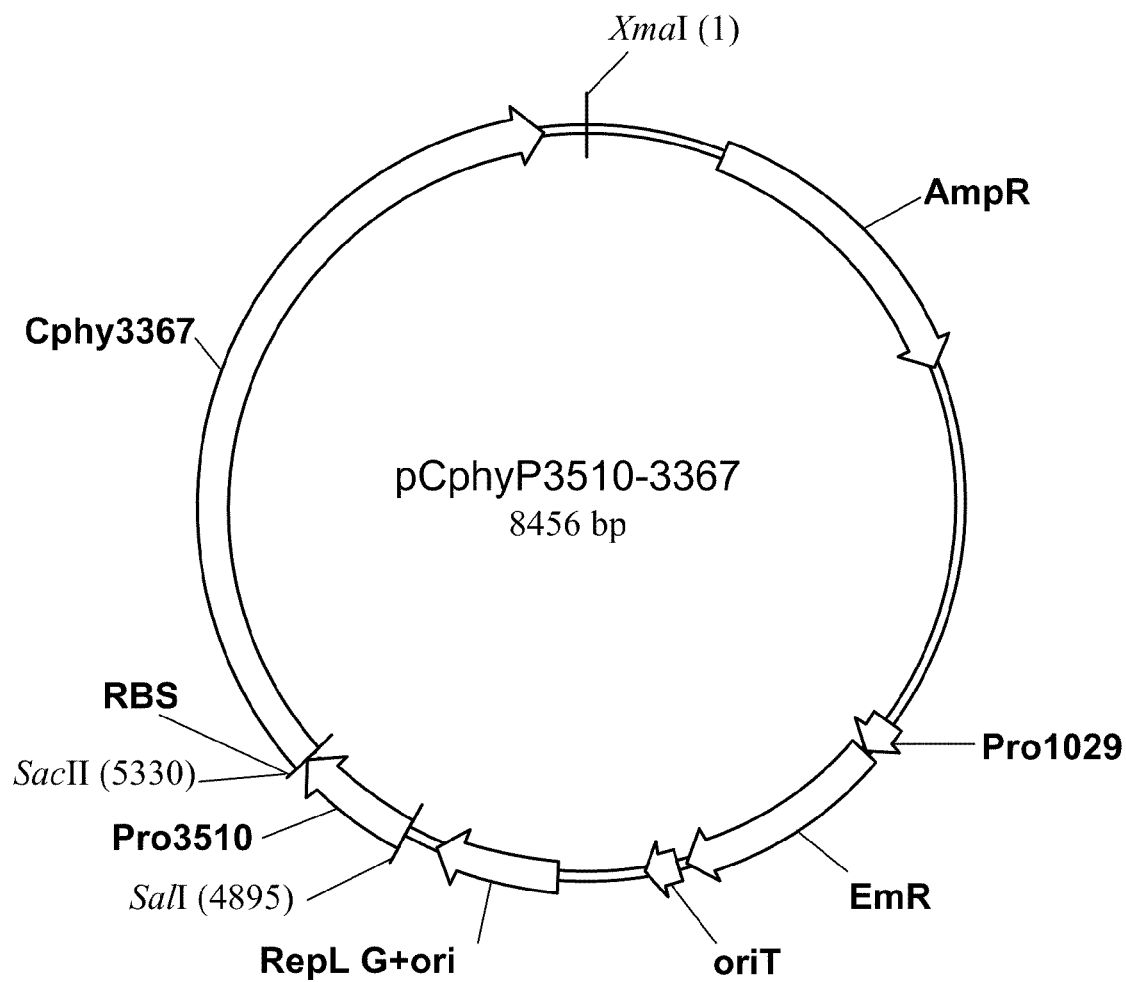
FIG. 19 is a depiction of a plasmid map for pCphyP3510-3367.

One or more cellulase genes may include each gene's own ribosome binding sites, are amplified via PCR, and subsequently digested with the appropriate enzymes as described previously under Cloning of Promoter. Resulting plasmids are also treated with the corresponding restriction enzymes and the amplified genes are mobilized into plasmids through standard ligation. The pCphyP3510-3367 plasmid (FIG. 19; SEQ ID NO: 1) is created by ligating the Cphy__3367 downstream of the Cphy__3510 promoter. *E. coli* is transformed with the plasmids and correct inserts are verified from transformants selected on selection plates.

Transconjugation

*E. coli* DH5α along with the helper plasmid pRK2030, are transformed with the different plasmids discussed above. *E. coli* colonies with both of the foregoing plasmids are selected on LB plates with 1 µg/ml ampicillin and 50 µg/ml kanamycin after growing overnight at 37° C. Single colonies are obtained after re-streaking on selective plates at 37° C. Growth media for *E. coli* (e.g. LB or LB supplemented with 1% glucose and 1% cellobiose) is inoculated with a single colony and either grown aerobically at 37° C. or anaerobically at 35° C. overnight. Fresh growth media is inoculated 1:1 with the overnight culture and grown until mid log phase. A *C. phytofermentans* strain is also grown in the same media until mid log.

The two different cultures, *C. phytofermentans* and *E. coli* with pRK2030 and one of the plasmids, are then mixed in different ratios, e.g. 1:10, 1:1, 1:10, 1:1, 10:1, 1:1, 10:1. The mating is performed in either liquid media, on plates or on mm Nucleopore™ Track-Etch Membrane (Whatman) at 35° C. The time is varied between 2 and 24 hours, and the mating media is the same growth media in which the culture are grown prior to the mating. After the mating procedure, the bacteria mixture is either spread directly onto plates or first grown on liquid media for 6 hours to 18 hours and then plated. The plates contain 10 µg/ml erythromycin as selective agent for *C. phytofermentans* and 10 µg/ml Trimethoprim, 150 µg/ml Cyclosporin, and 1 µg/ml Nalidixic acid as counter selectable media for *E. coli*.

After 3 to 5 days incubation at 35° C., erythromycin resistant colonies are picked from the plates and re-streaked on fresh selective plates. Single colonies are picked and the presence of the plasmid is confirmed by PCR reaction.

Cellulase Gene Expression

The expression of the cellulase genes on the different plasmids is then tested under conditions where there is little to no expression of the corresponding genes from the chromosomal locus. Positive candidates show constitutive expression of the cloned cellulases.

```
Plasmid-pCphyP3510-3367
                                                          SEQ ID NO: 1
   1 ccgggaattc actggccgtc gttttacaac gtcgtgactg ggaaaaccct ggcgttaccc
  61 aacttaatcg ccttgcagca catcccctt tcgccagctg gcgtaatagc gaagaggccc
 121 gcaccgatcg cccttcccaa cagttgcgca gcctgaatgg cgaatggcgc ctgatgcggt
 181 attttctcct tacgcatctg tgcggtattt cacaccgcat atggtgcact ctcagtacaa
 241 tctgctctga tgccgcatag ttaagccagc cccgacaccc gccaacaccc gctgacgcgc
 301 cctgacgggc ttgtctgctc ccggcatccg cttacagaca agctgtgacc gtctccggga
 361 gctgcatgtg tcagaggttt tcaccgtcat caccgaaacg cgcgagacga aagggcctcg
 421 tgatacgcct attttatag gttaatgtca tgataataat ggtttcttag acgtcaggtg
 481 gcacttttcg gggaaatgtg cgcggaaccc ctatttgttt attttctaa atacattcaa
 541 atatgtatcc gctcatgaga caataaccct gataaatgct tcaataatat tgaaaagga
 601 agagtatgag tattcaacat ttccgtgtcg cccttattcc cttttttgcg gcattttgcc
 661 ttcctgtttt tgctcaccca gaaacgctgg tgaaagtaaa agatgctgaa gatcagttgg
 721 gtgcacgagt gggttacatc gaactggatc tcaacagcgg taagatcctt gagagttttc
 781 gccccgaaga acgttttcca atgatgagca cttttaaagt tctgctatgt ggcgcggtat
 841 tatcccgtat tgacgccggg caagagcaac tcggtcgccg catacactat tctcagaatg
 901 acttggttga gtactcacca gtcacagaaa agcatcttac ggatggcatg acagtaagag
 961 aattatgcag tgctgccata accatgagtg ataacactgc ggccaactta cttctgacaa
1021 cgatcggagg accgaaggag ctaaccgctt ttttgcacaa catgggggat catgtaactc
1081 gccttgatcg ttgggaaccg gagctgaatg aagccatacc aaacgacgag cgtgacacca
1141 cgatgcctgt agcaatggca acaacgttgc gcaaactatt aactggcgaa ctacttactc
1201 tagcttcccg gcaacaatta atagactgga tggaggcgga taaagttgca ggaccacttc
1261 tgcgctcggc ccttccggct ggctggttta ttgctgataa atctggagcc ggtgagcgtg
1321 ggtctcgcgg tatcattgca gcactggggc cagatggtaa gccctcccgt atcgtagtta
1381 tctacacgac ggggagtcag gcaactatgg atgaacgaaa tagacagatc gctgagatag
1441 gtgcctcact gattaagcat tggtaactgt cagaccaagt ttactcatat atactttaga
1501 ttgatttaaa acttcatttt taatttaaaa ggatctaggt gaagatcctt tttgataatc
1561 tcatgaccaa aatcccttaa cgtgagtttt cgttccactg agcgtcagac cccgtagaaa
1621 agatcaaagg atcttcttga gatcctttt tctgcgcgt aatctgctgc ttgcaaacaa
1681 aaaaaccacc gctaccagcg gtggtttgtt tgccggatca agagctacca actcttttc
1741 cgaaggtaac tggcttcagc agagcgcaga taccaaatac tgtccttcta gtgtagccgt
1801 agttaggcca ccacttcaag aactctgtag caccgcctac atacctcgct ctgctaatcc
1861 tgttaccagt ggctgctgcc agtggcgata agtcgtgtct taccgggttg gactcaagac
1921 gatagttacc ggataaggcg cagcggtcgg gctgaacggg gggttcgtgc acacagccca
```

-continued

```
1981 gcttggagcg aacgacctac accgaactga gatacctaca gcgtgagcta tgagaaagcg
2041 ccacgcttcc cgaagggaga aaggcggaca ggtatccggt aagcggcagg gtcggaacag
2101 gagagcgcac gagggagctt ccaggggaaa acgcctggta tctttatagt cctgtcgggt
2161 ttcgccacct ctgacttgag cgtcgatttt tgtgatgctc gtcagggggg cggagcctat
2221 ggaaaaacgc cagcaacgcg gccttttttac ggttcctggc cttttgctgg ccttttgctc
2281 acatgttctt tcctgcgtta tcccctgatt ctgtggataa ccgtattacc gcctttgagt
2341 gagctgatac cgctcgccgc agccgaacga ccgagcgcag cgagtcagtg agcgaggaag
2401 cggaagagcg cccaatacgc aaaccgcctc tccccgcgcg ttggccgatt cattaatgca
2461 gctggcacga caggtttccc gactggaaag cgggcagtga gcgcaacgca attaatgtga
2521 gttagctcac tcattaggca ccccaggctt tacactttat gcttccggct cgtatgttgt
2581 gtggaattgt gagcggataa caatttcaca caggaaacag ctatgaccat gattacgcca
2641 aagctttggc taacacacac gccattccaa ccaatagttt tctcggcata aagccatgct
2701 ctgacgctta aatgcactaa tgccttaaaa aaacattaaa gtctaacaca ctagacttat
2761 ttacttcgta attaagtcgt taaaccgtgt gctctacgac caaaagtata aaacctttaa
2821 gaactttctt ttttcttgta aaaaagaaa ctagataaat ctctcatatc ttttattcaa
2881 taatcgcatc agattgcagt ataaatttaa cgatcactca tcatgttcat atttatcaga
2941 gctccttata ttttatttcg atttatttgt tatttattta acattttctc attgacctca
3001 tcttttctat gtgttattct tttgttaatt gtttacaaat aatctacgat acatagaagg
3061 aggaaaaact agtatactag tatgaacgag aaaaatataa aacacagtca aactttatt
3121 acttcaaaac ataatataga taaaataatg acaaatataa gattaaatga acatgataat
3181 atctttgaaa tcggctcagg aaaagggcat tttaccctg aattagtaca gaggtgtaat
3241 ttcgtaactg ccattgaaat agaccataaa ttatgcaaaa ctacagaaaa taaacttgtt
3301 gatcacgata atttccaagt tttaaacaag gatatattgc agtttaaatt tcctaaaaac
3361 caatcctata aaatatttgg taatataccct tataacataa gtacggatat aatacgcaaa
3421 attgtttttg atagtatagc tgatgagatt tatttaatcg tggaatacgg gtttgctaaa
3481 agattattaa atacaaaacg ctcattggca ttatttttaa tggcagaagt tgatatttct
3541 atattaagta tggttccaag agaatatttt catcctaaac ctaaagtgaa tagctcactt
3601 atcagattaa atagaaaaaa atcaagaata tcacacaaag ataaacagaa gtataattat
3661 ttcgttatga aatgggttaa caaagaatac aagaaaatat ttacaaaaaa tcaatttaac
3721 aattccttaa aacatgcagg aattgacgat ttaaacaata ttagctttga acaattctta
3781 tctcttttca atagctataa attattttaat aagtaagtta agggatgcat aaactgcatc
3841 ccttaacttg ttttcgtgt acctattttt tgtgaatcga tccggccagc ctcgcagagc
3901 aggattcccg ttgagcaccg ccaggtgcga taagggaca gtgaagaagg aacacccgct
3961 cgcgggtggg cctacttcac ctatcctgcc cggatcgatt atgtcttttg cgcattcact
4021 tcttttctat ataaatatga gcgaagcgaa taagcgtcgg aaaagcagca aaagtttcc
4081 tttttgctgt tggagcatgg gggttcaggg ggtgcagtat ctgacgtcaa tgccgagcga
4141 aagcgagccg aagggtagca tttacgttag ataaccccct gatatgctcc gacgctttat
4201 atagaaaaga agattcaact aggtaaaatc ttaatatagg ttgagatgat aaggtttata
4261 aggaatttgt tgttctaat ttttcactca ttttgttcta atttctttta acaaatgttc
4321 ttttttttt agaacagtta tgatatagtt agaatagttt aaaataagga gtgagaaaaa
4381 gatgaaagaa agatatggaa cagtctataa aggctctcag aggctcatag acgaagaaag
```

-continued

```
4441 tggagaagtc atagaggtag acaagttata ccgtaaacaa acgtctggta acttcgtaaa 4501 ggcatatata gtgcaattaa taagtatgtt agatatgatt ggcggaaaaa aacttaaaat 4561 cgttaactat atcctagata atgtccactt aagtaacaat acaatgatag ctacaacaag 4621 agaaatagca aaagctacag gaacaagtct acaaacagta ataacaacac ttaaaatctt 4681 agaagaagga aatattataa aaagaaaaac tggagtatta atgttaaacc ctgaactact 4741 aatgagaggc gacgaccaaa aacaaaaata cctcttactc gaatttggga actttgagca 4801 agaggcaaat gaaatagatt gacctcccaa taacaccacg tagttattgg gaggtcaatc 4861 tatgaaatgc gattaagctt agcttggctg caggtcgaca gacagcataa gtcacatcca 4921 gacaaatgtc ctataggatg ttagtagggg tttggagaat gcccgtaag gcaggttatt 4981 tggctagata taatcaatcc agttacagga tagtaggatt gcaacccagt cgttttgacc 5041 agtttgtaca agaattttaa tttgtcgaaa tattgtggca aatcaaatga agttctttga 5101 tgaaatgttt agaaacatga cttagaatgg ggtacaaaaa gtgaatttgt aagcaaaaag 5161 acttgacctt tcctacgata gttgttataa tcatcttgtt attggaacga ttatatttac 5221 ttatgcacat tttagagttt ttcgaattgt taatacatca ttaacaattt aattatactc 5281 gttatgtgac gtaagtcaat ataatacaaa accatatatt ttaagccgcg ggcagaaagg 5341 atgagagata tgaaaaagat aataagtctt ttattagtga taacacttct gatatccatg 5401 gcaccatcga aagctgacgc agcggaaacc aattataatt acggagaagc tcttcaaaaa 5461 tcaatcatgt tttatgagtt tcaacgttct ggtaaactgc caagtaccat tcggaataat 5521 tggagaggtg actctggttt aaccgatgga gcagatgttg gtttggatct aactggtggc 5581 tggtatgatg ctggtgatca tgtaaaattt aatcttcctt tggcttatac tgtaacaatg 5641 ttagcatggg cagtatatga agaagaggct actctttcaa aggcaggcca attaagttat 5701 ttattagatg aaattaagtg gtctagtgat tacctaatta aatgtcatcc acaagcaaat 5761 gtattttatt atcaggttgg taatggaaat acagatcact cttggtgggg acctgctgaa 5821 gttatgcaga tggctagacc gtcctataag gttgatttaa ataacccagg ttctactgta 5881 gtaggagaag cagcagcagc tcttgcagca acagcactta tatataagac aaaagaccct 5941 acttattcag caacttgcct tcgtcatgca aaagagcttt ttaattttgc agatacaaca 6001 aaaagcgatg ctggatatac agcagcaagt gggttctata cttcctatag tggattttat 6061 gatgaattat cctgggcagc tacatggatt taccttgcaa gtggagaagc gacctatttg 6121 gataaggcag aatcttatgt agccaaatgg ggaacagaac ctcaatcttc cacattaagt 6181 tataagtggg cacaaaactg ggatgatgtt cactatggtg cagctttatt attagcaaga 6241 attacaaata aagcaatttta taagaacaat attgaaatgc atcttgacta ttggactaca 6301 gggtataatg gtagtcgtat tacttataca ccaaaaggac ttgcttggtt agattcctgg 6361 ggtgcattaa gatatgcgac gacaacagca tttctagcaa gtgtttatgc tgattggagc 6421 ggatgtagtg ctggaaaagt tagtacttac aatgcatttg cgaaacagca ggtagattat 6481 gcattaggaa gtaccggaag aagttttgtg gttggatatg gtgtaaattc tccaacaaga 6541 cctcatcata gaactgctca tagttcatgg gcagacagtc agacggagcc aaattaccat 6601 agacacacca tttatggtgc tttagtaggt ggacctggta ataatgatag ttatgaggat 6661 aacattaata attatgtaaa caatgaaatc gcttgtgact ataatgcagg ttttgttggc 6721 gcattggcta agtttataa aacatatggc ggaacaccaa ttgcaaactt taaggcaatc 6781 gaaacagtaa caaacgatga gttatttatt caagctggta ttaatgcctc tggtccatct 6841 tttatcgaag taaaggcatt ggttttcaat gagacaggtt ggccagctcg tgttaccgat
```

```
-continued
6901 aaattatcct ttaagtattt tattgatatc tcggaatatg tagcaaaggg atatacaaag 6961 aatgatttta cggtatcgac aaattataac aatggagcaa ccacatcggc attgcttcct 7021 tgggatgctg cgaataatat ctattatgtg aatgtagact tctctggaac taagatttat 7081 cctggtggac agtctgcata taagaaagaa gtacaattta gaattgctgg tccacaaaac 7141 gttaatatat gggacaattc caatgactac tcctttacac aaattgctaa tgttagttca 7201 ggaaataccg taaagaccac atatatacca ttgtatgata atggtaaatt agtatttggt 7261 aatgagccaa agacgggtgt tccttctgca agtcttgata agactacagc aaactttgac 7321 aaaaacccag ctgtatccgc agatatacca gtaaccatta actataatgg taatacatta 7381 acagcggtta agaatggaac aacggtttta acgaaaggta ctgattatac tgtatctggt 7441 aatgtagtaa cgttatctaa gaattatttc ttagcacaga gcgctagtac ggttacttta 7501 acatttgtat ttagtggcgg taacgatgca acattaaaag tgactttagt agatacttct 7561 ccaagtgcat ccattaatcc aaattctgct gtctttgata aggctagcgg aaaacaggaa 7621 aatatagtta ttacgcttac accaaatggc aataccttag ctggacttaa gaatgggtct 7681 aagagcctgg taactggaac tgattatacc gtttccggaa caacagtgac gattctatct 7741 tcttatttaa gtcaatttgc agtaggaagt caatctattg tatttgaaat gaataaaggg 7801 acaaatccag tcttagcagt taccattaag gattcttctg ttgttactcc aacaggaaat 7861 attaaacttc aaatgtttaa tggaaattct tctgcaacaa cgaatggcat tgcaccaaga 7921 attaaattaa ttaacaccgg aactactgca atcaacttat ccgatgttaa gattcgctat 7981 tattatacaa tcaatggcga aaaggatcag gcattctggt gtgattattc gacgattggt 8041 agttccaatg taaatggtac tttcgtaaag atgagtacac caaaaacaaa tgcagattac 8101 tatctagaat tttcatttaa gtccgctgcc ggaactttaa acgcagggca aagtattgaa 8161 gttcaaggaa gattttctaa ggtagactgg acaaactata cacaaacaga tgattattcg 8221 tttggtgata gtaactcaag ttatgctgat tggaataaga caacagtata tatctctgat 8281 gttttggttt ggggagtcga accataatag gagaaaaaat gtaataattt ttagaggggt 8341 cataacttag tatacatgtc tgtatatgag gtccgacacg tgccacacgg catgtgtcgg 8401 gcctcatttt tatacagcgt gtatgtgacc ttattcatga caagggatcg tccgcc
```

Other Embodiments

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. An isolated polynucleotide cassette comprising:
   a. a nucleic acid sequence encoding at least one transcriptional regulator from *C. phytofermentans*; and
   b. a nucleic acid sequence encoding
      i. at least one hydrolase from *C. phytofermentans*, wherein said nucleic acid is selected from Table 6; or
      ii. at least one ABC-transporter from *C. phytofermentans*, wherein said nucleic acid is selected from ABC-transporter genes in Table 7.

2. The cassette of claim 1, wherein said at least one hydrolase is selected from the group consisting of Cphy407, Cphy408, Cphy0430, Cphy3854, Cphy0857, Cphy0694, and Cphy1929.

3. The cassette of claim 1, wherein said at least one ABC-transporter is selected from the group consisting of Cphy3854, Cphy3855, Cphy3857, Cphy3858, Cphy3859, Cphy3860, Cphy3861, and Cphy3862.

4. The cassette of claim 1, wherein said at least one transcriptional regulator from *C. phytofermentans* is selected from Table 8.

5. The cassette of claim 1, further comprising a regulatory sequence.

6. The cassette of claim 5, wherein said regulatory sequence is operably linked to said at least one hydrolase, said at least one ABC-transporter, or said at least one transcriptional regulator.

7. The cassette of claim 1, wherein said isolated polynucleotide cassette is inserted into an expression vector.

8. The vector of claim 7, wherein at least one of said nucleic acid sequences is methylated.

9. The vector of claim 8, wherein said methylation prevents restriction of said said nucleic acid sequences by a *Clostridium* endonuclease.

10. The isolated polynucleotide cassette of claim 1, wherein said at least one transcriptional regulator is Cphy1187.

11. The isolated polynucleotide cassette of claim 1, wherein said at least one hydrolase is Cphy3207.

12. The isolated polynucleotide cassette of claim 1, wherein said at least one transcriptional regulator is Cphy1187 and the hydrolase is Cphy3207.

13. A recombinant microorganism comprising:
   a. an isolated nucleic acid sequence encoding at least one transcriptional regulator from *C. phytofermentans*; and
   b. an isolated nucleic acid sequence encoding
      i. at least one hydrolase from *C. phytofermentans*, wherein said isolated nucleic acid is selected from Table 6; or
      ii. at least one ABC-transporter from *C. phytofermentans*, wherein said isolated nucleic acid is selected from ABC-transporter genes in Table 7,
   wherein at least one of said isolated nucleic acid sequence encoding at least one transcription regulator and said isolated nucleic acid sequence encoding at least one hydrolase or at least one ABC-transporter from C. phytofermentans is heterologous to the microorganism or is an additional copy of an endogenous nucleic acid sequence.

14. The recombinant microorganism of claim 13, wherein said microorganism is selected from the group consisting of *Clostridium cellulovorans*, *Clostridium cellulolyticum*, *Clostridium thermocellum*, *Clostridium josui*, *Clostridium papyrosolvens*, *Clostridium cellobioparum*, *Clostridium hungatei*, *Clostridium cellulosi*, *Clostridium stercorarium*, *Clostridium termitidis*, *Clostridium thermocopriae*, *Clostridium celerecrescens*, *Clostridium polysaccharolyti-* cum, *Clostridium populeti, Clostridium lentocellum, Clostridium chartatabidum, Clostridium aldrichii, Clostridium herbivorans, Acetivibrio cellulolyticus, Bacteroides cellulosolvens, Caldicellulosiruptor saccharolyticum, Ruminococcus albus, Ruminococcus flavefaciens, Fibrobacter succinogenes, Eubacterium cellulosolvens, Butyrivibrio fibrisolvens, Anaerocellum thermophilum, Halocella cellulolytica, Thermoanaerobacterium thermosaccharolyticum* and *Thermoanaerobacterium saccharolyticum*.

15. The recombinant microorganism of claim 13, wherein said at least one hydrolase is selected from the group consisting of Cphy407, Cphy408, Cphy0430, Cphy3854, Cphy0857, Cphy0694, and Cphy1929.

16. The recombinant microorganism of claim 13, wherein said at least one ABC-transporter is selected from the group consisting of Cphy3854, Cphy3855, Cphy3857, Cphy3858, Cphy3859, Cphy3860, Cphy3861, and Cphy3862.

17. The recombinant microorganism of claim 13, wherein said hydrolase is selected from the group consisting of Cphy407, Cphy408, Cphy0430, Cphy3854, Cphy0857, Cphy0694, and Cphy1929; and wherein said ABC-transporter is selected from the group consisting of Cphy3854, Cphy3855, Cphy3857, Cphy3858, Cphy3859, Cphy3860, Cphy3861, and Cphy3862.

18. The recombinant microorganism of claim 13, wherein said hydrolase is Cphy3207.

19. The recombinant microorganism of claim 13, wherein said transcriptional regulator is Cphy1187 and said hydrolase is Cphy3207.

20. The recombinant microorganism of claim 13, wherein said Cphy1187 modulates the expression of Cphy3207.

21. The recombinant microorganism of claim 13, wherein said recombinant microorganism is a *Clostridium* microorganism.

22. The recombinant microorganism of claim 13, wherein said recombinant microorganism is a *Clostridium phytofermentans* microorganism.

23. The recombinant microorganism of claim 13, wherein said recombinant microorganism is a *Clostridium thermocellum* microorganism.

24. The recombinant microorganism of claim 13, wherein at least one of said isolated nucleic acid sequence encoding at least one transcription regulator and said isolated nucleic acid sequence encoding at least one hydrolase or at least one ABC-transporter from *C. phytofermentans* is heterologous to the microorganism.

25. The recombinant microorganism of claim 13, wherein at least one of said isolated nucleic acid sequence encoding at least one transcription regulator and said isolated nucleic acid sequence encoding at least one hydrolase or at least one ABC-transporter from *C. phytofermentans* is an additional copy of an endogenous nucleic acid sequence.

* * * * *

SEQUENCE LISTING

```
<160> NUMBER OF SEQ ID NOS: 1

<210> SEQ ID NO 1
<211> LENGTH: 8456
<212> TYPE: DNA
<213> ORGANISM: Artificial Sequence
<220> FEATURE:
<223> OTHER INFORMATION: Plasmid

<400> SEQUENCE: 1
ccgggaattc actggccgtc gttttacaac gtcgtgactg ggaaaaccct ggcgttaccc      60
aacttaatcg ccttgcagca catcccccctt tcgccagctg gcgtaatagc gaagaggccc     120
```

```
gcaccgatcg cccttcccaa cagttgcgca gcctgaatgg cgaatggcgc ctgatgcggt      180
attttctcct tacgcatctg tgcggtattt cacaccgcat atggtgcact ctcagtacaa      240
tctgctctga tgccgcatag ttaagccagc cccgacaccc gccaacaccc gctgacgcgc      300
cctgacgggc ttgtctgctc ccggcatccg cttacagaca agctgtgacc gtctccggga      360
gctgcatgtg tcagaggttt tcaccgtcat caccgaaacg cgcgagacga aagggcctcg      420
tgatacgcct atttttatag gttaatgtca tgataataat ggtttcttag acgtcaggtg      480
gcacttttcg gggaaatgtg cgcggaaccc ctatttgttt attttctaa atacattcaa       540 atatgtatcc gctcatgaga caataaccct gataaatgct tcaataatat tgaaaaagga      600
agagtatgag tattcaacat ttccgtgtcg cccttattcc cttttttgcg cattttgcc       660 ttcctgtttt tgctcaccca gaaacgctgg tgaaagtaaa agatgctgaa gatcagttgg      720
gtgcacgagt gggttacatc gaactggatc tcaacagcgg taagatcctt gagagttttc      780
gccccgaaga acgttttcca atgatgagca cttttaaagt tctgctatgt ggcgcggtat      840
tatcccgtat tgacgccggg caagagcaac tcggtcgccg catacactat tctcagaatg      900
acttggttga gtactcacca gtcacagaaa agcatcttac ggatggcatg acagtaagag      960
aattatgcag tgctgccata accatgagtg ataacactgc ggccaactta cttctgacaa     1020
cgatcggagg accgaaggag ctaaccgctt ttttgcacaa catgggggat catgtaactc     1080
gccttgatcg ttgggaaccg gagctgaatg aagccatacc aaacgacgag cgtgacacca     1140
cgatgcctgt agcaatggca acaacgttgc gcaaactatt aactggcgaa ctacttactc     1200
tagcttcccg gcaacaatta atagactgga tggaggcgga taaagttgca ggaccacttc     1260
tgcgctcggc ccttccggct ggctggttta ttgctgataa atctggagcc ggtgagcgtg     1320
ggtctcgcgg tatcattgca gcactggggc cagatggtaa gccctcccgt atcgtagtta     1380
tctacacgac ggggagtcag gcaactatgg atgaacgaaa tagacagatc gctgagatag     1440
gtgcctcact gattaagcat tggtaactgt cagaccaagt ttactcatat atactttaga     1500
ttgatttaaa acttcatttt taatttaaaa ggatctaggt gaagatcctt tttgataatc     1560
tcatgaccaa aatcccttaa cgtgagtttt cgttccactg agcgtcagac cccgtagaaa     1620
agatcaaagg atcttcttga gatccttttt ttctgcgcgt aatctgctgc ttgcaaacaa     1680
aaaaaccacc gctaccagcg gtggtttgtt tgccggatca agagctacca actctttttc     1740
cgaaggtaac tggcttcagc agagcgcaga taccaaatac tgtccttcta gtgtagccgt     1800
agttaggcca ccacttcaag aactctgtag caccgcctac atacctcgct ctgctaatcc     1860
tgttaccagt ggctgctgcc agtggcgata agtcgtgtct taccgggttg gactcaagac     1920
gatagttacc ggataaggcg cagcggtcgg gctgaacggg gggttcgtgc acacagccca     1980
gcttggagcg aacgacctac accgaactga gatacctaca gcgtgagcta tgagaaagcg     2040
ccacgcttcc cgaagggaga aaggcggaca ggtatccggt aagcggcagg gtcggaacag     2100
gagagcgcac gagggagctt ccagggggaa acgcctggta tctttatagt cctgtcgggt     2160
ttcgccacct ctgacttgag cgtcgatttt tgtgatgctc gtcaggggggg cggagcctat     2220 ggaaaaacgc cagcaacgcg gcctttttac ggttcctggc cttttgctgg ccttttgctc     2280
acatgttctt cctgcgttta tcccctgatt ctgtggataa ccgtattacc gcctttgagt     2340
gagctgatac cgctcgccgc agccgaacga ccgagcgcag cgagtcagtg agcgaggaag     2400
cggaagagcg cccaatacgc aaaccgcctc tccccgcgcg ttggccgatt cattaatgca     2460
gctggcacga caggtttccc gactggaaag cgggcagtga gcgcaacgca attaatgtga     2520
```

```
gttagctcac tcattaggca ccccaggctt tacactttat gcttccggct cgtatgttgt    2580
gtggaattgt gagcggataa caatttcaca caggaaacag ctatgaccat gattacgcca    2640
aagctttggc taacacacac gccattccaa ccaatagttt tctcggcata aagccatgct    2700
ctgacgctta aatgcactaa tgccttaaaa aaacattaaa gtctaacaca ctagacttat    2760
ttacttcgta attaagtcgt taaaccgtgt gctctacgac caaaagtata aaacctttaa    2820
gaactttctt ttttcttgta aaaaagaaa ctagataaat ctctcatatc ttttattcaa     2880
taatcgcatc agattgcagt ataaatttaa cgatcactca tcatgttcat atttatcaga    2940
gctccttata ttttatttcg atttatttgt tatttattta acattttctt attgacctca    3000
tcttttctat gtgttattct tttgttaatt gtttacaaat aatctacgat acatagaagg    3060
aggaaaaact agtatactag tatgaacgag aaaatataa aacacagtca aaactttatt     3120
acttcaaaac ataatataga taaaataatg acaaatataa gattaaatga acatgataat    3180
atctttgaaa tcggctcagg aaagggcat tttacccttg aattagtaca gaggtgtaat     3240
ttcgtaactg ccattgaaat agaccataaa ttatgcaaaa ctacagaaaa taaacttgtt    3300
gatcacgata atttccaagt tttaaacaag gatatattgc agtttaaatt tcctaaaaac    3360
caatcctata aaatatttgg taatatacct tataacataa gtacggatat aatacgcaaa    3420
attgttttg atagtatagc tgatgagatt tatttaatcg tggaatacgg gtttgctaaa     3480
agattattaa atacaaaacg ctcattggca ttattttaa tggcagaagt tgatatttct     3540
atattaagta tggttccaag agaatatttt catcctaaac ctaaagtgaa tagctcactt    3600
atcagattaa atagaaaaaa atcaagaata tcacacaaag ataaacagaa gtataattat    3660
ttcgttatga aatgggttaa caaagaatac aagaaaatat ttacaaaaaa tcaatttaac    3720
aattccttaa aacatgcagg aattgacgat ttaaacaata ttagctttga acaattctta    3780
tctcttttca atagctataa attatttaat agtaagtta agggatgcat aaactgcatc     3840
ccttaacttg ttttcgtgt acctatttt tgtgaatcga tccggccagc ctcgcagagc      3900
aggattcccg ttgagcaccg ccaggtgcga ataagggaca gtgaagaagg aacacccgct    3960
cgcgggtggg cctacttcac ctatcctgcc cggatcgatt atgtcttttg cgcattcact    4020
tcttttctat ataaatatga gcgaagcgaa taagcgtcgg aaaagcagca aaagtttcc     4080
ttttgctgt tggagcatgg gggttcaggg ggtgcagtat ctgacgtcaa tgccgagcga     4140
aagcgagccg aagggtagca tttacgttag ataacccct gatatgctcc gacgctttat     4200
atagaaaaga agattcaact aggtaaaatc ttaatatagg ttgagatgat aaggtttata    4260
aggaatttgt ttgttctaat ttttcactca ttttgttcta atttcttta acaaatgttc     4320
ttttttttt agaacagtta tgatatagtt agaatagttt aaaataagga gtgagaaaa     4380
gatgaaagaa agatatggaa cagtctataa aggctctcag aggctcatag acgaagaaag    4440
tggagaagtc atagaggtag acaagttata ccgtaaacaa acgtctggta acttcgtaaa    4500
ggcatatata gtgcaattaa taagtatgtt agatatgatt ggcggaaaaa aacttaaaat    4560
cgttaactat atcctagata atgtccactt aagtaacaat acaatgatag ctacaacaag    4620
agaaatagca aaagctacag gaacaagtct acaaacagta ataacaacac ttaaaatctt    4680
agaagaagga aatattataa aagaaaaac tggagtatta atgttaaacc ctgaactact     4740
aatgagaggc gacgaccaaa aacaaaaata cctcttactc gaatttggga actttgagca    4800
agaggcaaat gaaatagatt gacctcccaa taacaccacg tagttattgg gaggtcaatc    4860
tatgaaatgc gattaagctt agcttggctg caggtcgaca gacagcataa gtcacatcca    4920
```

```
gacaaatgtc ctataggatg ttagtagggg tttggagaat tgcccgtaag gcaggttatt   4980
tggctagata taatcaatcc agttacagga tagtaggatt gcaacccagt cgttttgacc   5040
agtttgtaca agaattttaa tttgtcgaaa tattgtggca aatcaaatga agttctttga   5100
tgaaatgttt agaaacatga cttagaatgg ggtacaaaaa gtgaatttgt aagcaaaaag   5160
acttgacctt tcctacgata gttgttataa tcatcttgtt attggaacga ttatatttac   5220
ttatgcacat tttagagttt ttcgaattgt taatacatca ttaacaattt aattatactc   5280
gttatgtgac gtaagtcaat ataatacaaa accatatatt ttaagccgcg gcagaaagg    5340
atgagagata tgaaaaagat aataagtctt ttattagtga taacacttct gatatccatg   5400
gcaccatcga aagctgacgc agcggaaacc aattataatt acggagaagc tcttcaaaaa   5460
tcaatcatgt tttatgagtt tcaacgttct ggtaaactgc caagtaccat tcggaataat   5520
tggagaggtg actctggttt aaccgatgga gcagatgttg gtttggatct aactggtggc   5580
tggtatgatg ctggtgatca tgtaaaattt aatcttcctt tggcttatac tgtaacaatg   5640
ttagcatggg cagtatatga agaagaggct actctttcaa aggcaggcca attaagttat   5700
ttattagatg aaattaagtg gtctagtgat tacctaatta aatgtcatcc acaagcaaat   5760
gtattttatt atcaggttgg taatggaaat acagatcact cttggtgggg acctgctgaa   5820
gttatgcaga tggctagacc gtcctataag gttgatttaa ataacccagg ttctactgta   5880
gtaggagaag cagcagcagc tcttgcagca acagcactta tatataagac aaaagacccct  5940
acttattcag caacttgcct tcgtcatgca aaagagcttt ttaattttgc agatacaaca   6000
aaaagcgatg ctggatatac agcagcaagt gggttctata cttcctatag tggattttat   6060
gatgaattat cctgggcagc tacatggatt taccttgcaa gtggagaagc gacctatttg   6120
gataaggcag aatcttatgt agccaaatgg ggaacagaac ctcaatcttc cacattaagt   6180
tataagtggg cacaaaactg ggatgatgtt cactatggtg cagctttatt attagcaaga   6240
attacaaata aagcaattta taagaacaat attgaaatgc atcttgacta ttggactaca   6300
gggtataatg gtagtcgtat tacttataca ccaaaaggac ttgcttggtt agattcctgg   6360
ggtgcattaa gatatgcgac gacaacagca tttctagcaa gtgtttatgc tgattggagc   6420
ggatgtagtg ctggaaaagt tagtacttac aatgcatttg cgaaacagca ggtagattat   6480
gcattaggaa gtaccggaag aagttttgtg gttggatatg tgtaaattc ccaacaaga    6540
cctcatcata gaactgctca tagttcatgg gcagacagtc agacggagcc aaattaccat   6600
agacacacca tttatggtgc tttagtaggt ggacctggta taatgatag ttatgaggat    6660
aacattaata attatgtaaa caatgaaatc gcttgtgact ataatgcagg ttttgttggc   6720
gcattggcta aagtttataa acatatggc ggaacaccaa ttgcaaactt taaggcaatc    6780
gaaacagtaa caaacgatga gttatttatt caagctggta ttaatgcctc tggtccatct   6840
tttatcgaag taaaggcatt ggttttcaat gagacaggtt ggccagctcg tgttaccgat   6900
aaattatcct ttaagtattt tattgatatc tcggaatatg tagcaaaggg atatacaaag   6960
aatgatttta cggtatcgac aaattataac aatggagcaa ccacatcggc attgcttcct   7020
tgggatgctg cgaataatat ctattatgtg aatgtagact tctctggaac taagatttat   7080
cctggtggac agtctgcata taagaaagaa gtacaattta gaattgctgg tccacaaaac   7140
gttaatatat gggacaattc caatgactac tcctttacac aaattgctaa tgttagttca   7200
ggaaataccg taaagaccac atatatacca ttgtatgata atggtaaatt agtatttggt   7260
aatgagccaa agacgggtgt tccttctgca agtcttgata agactacagc aaactttgac   7320
```

-continued

```
aaaaacccag ctgtatccgc agatatacca gtaaccatta actataatgg taatacatta    7380
acagcggtta agaatggaac aacggtttta acgaaaggta ctgattatac tgtatctggt    7440
aatgtagtaa cgttatctaa gaattatttc ttagcacaga gcgctagtac ggttacttta    7500
acatttgtat ttagtggcgg taacgatgca acattaaaag tgactttagt agatacttct    7560
ccaagtgcat ccattaatcc aaattctgct gtctttgata aggctagcgg aaaacaggaa    7620
aatatagtta ttacgcttac accaaatggc aataccttag ctggacttaa gaatgggtct    7680
aagagcctgg taactggaac tgattatacc gtttccggaa caacagtgac gattctatct    7740
tcttatttaa gtcaatttgc agtaggaagt caatctattg tatttgaaat gaataaaggg    7800
acaaatccag tcttagcagt taccattaag gattcttctg ttgttactcc aacaggaaat    7860
attaaacttc aaatgtttaa tggaaattct tctgcaacaa cgaatggcat tgcaccaaga    7920
attaaattaa ttaacaccgg aactactgca atcaacttat ccgatgttaa gattcgctat    7980
tattatacaa tcaatggcga aaaggatcag gcattctggt gtgattattc gacgattggt    8040
agttccaatg taaatggtac tttcgtaaag atgagtacac caaaaacaaa tgcagattac    8100
tatctagaat tttcatttaa gtccgctgcc ggaactttaa acgcagggca aagtattgaa    8160
gttcaaggaa gattttctaa ggtagactgg acaaactata cacaaacaga tgattattcg    8220
tttggtgata gtaactcaag ttatgctgat tggaataaga caacagtata tatctctgat    8280
gttttggttt ggggagtcga accataatag gagaaaaaat gtaataattt ttagaggggt    8340
cataacttag tatacatgtc tgtatatgag gtccgacacg tgccacacgg catgtgtcgg    8400 gcctcattt  tatacagcgt gtatgtgacc ttattcatga caagggatcg tccgcc         8456
```